(12) United States Patent
Ruaño et al.

(10) Patent No.: US 7,747,392 B2
(45) Date of Patent: Jun. 29, 2010

(54) PHYSIOGENOMIC METHOD FOR PREDICTING CLINICAL OUTCOMES OF TREATMENTS IN PATIENTS

(75) Inventors: Gualberto Ruaño, Milford, CT (US); Andreas Windemuth, Woodbridge, CT (US)

(73) Assignee: Genomas, Inc., Hartford, CT (US)

( * ) Notice: Subject to any disclaimer, the term of this patent is extended or adjusted under 35 U.S.C. 154(b) by 0 days.

(21) Appl. No.: 11/371,511

(22) Filed: Mar. 8, 2006

(65) Prior Publication Data

US 2006/0234262 A1 Oct. 19, 2006

Related U.S. Application Data

(63) Continuation-in-part of application No. 11/010,716, filed on Dec. 14, 2004.

(51) Int. Cl.
*G01N 33/48* (2006.01)
*G06G 7/58* (2006.01)

(52) U.S. Cl. .............................. 702/19; 702/20; 703/11

(58) Field of Classification Search ........................ None
See application file for complete search history.

(56) References Cited

U.S. PATENT DOCUMENTS

| | | | |
|---|---|---|---|
| 6,081,786 A | 6/2000 | Barry et al. | |
| 2001/0034023 A1 | 10/2001 | Stanton, Jr. et al. | |
| 2003/0219760 A1 | 11/2003 | Gordon et al. | |
| 2004/0018491 A1 | 1/2004 | Gunderson et al. | |
| 2004/0166519 A1 | 8/2004 | Cargill et al. | |
| 2005/0079532 A1* | 4/2005 | Margus et al. | 435/6 |
| 2006/0223058 A1* | 10/2006 | Cox et al. | 435/5 |
| 2006/0278241 A1* | 12/2006 | Ruaño | 128/898 |
| 2007/0038386 A1* | 2/2007 | Schadt et al. | 702/20 |

OTHER PUBLICATIONS

Haga et al. J. Hum. Genet., vol. 47, pp. 605-610, 2002.*
Glannon; "Key Concepts Endophenotypes"; Philosophy, Psychiatry & Psychology; 10; pp. 277-284; (2003).
International Search Report and Written Opinion; International Application No. PCT/US 07/63501; International Filing Date Mar. 7, 2007; Applicant's File Reference 4835-4003PC1; 14 pages.
Blangero, et al.; "Robust LOD Scores for Variance Component-Based Linkage Analysis"; Genetic Epidemiology; 19 (Suppl. 1); pp. S8-S14; 2000.
Holford et al.; "Designing Physiogenomic Studies"; Pharmacogenomics; 7; pp. 157-158; (2006).
Manly, et al., "Overview of QTL Mapping Software and Introduction to Map Manager QT"; Mammalian Genome; 10; pp. 327-334; 1999.
Ruano et al., "Physiogenomic Analysis Links Serum Creatine Kinase Activities During Statin Therapy to Vascular Smooth Muscle Homeostasis"; Pharmacogenomics; 6; pp. 865-872; (2005).
Ruano, et al.;"Apolipoprotein A1 Genotype Affects the Change in High Density Lipoprotein Cholesterol Subfractions With Exercise Training"; Atherosclerosis; 185; pp. 65-59; 2006.
DiRienzo, et al; "Non-parametric Methods to Predict HIV Drug Susceptibility Phenotype from Genotype"; Statistics in Medicine; 22; pp. 2785-2798; (2003).
Hastie, et al; "Generalized Additive Models"; Department of Statistics and Division of Biostatistics; pp. 1-14; May 12, 1995.
U.S. Appl. No. 11/010,716, filed Dec. 12, 2004, Nonfinal Office Action dated Aug. 31, 2007; 16 pages.
U.S. Appl. No. 11/010,716, filed Dec. 14, 2004, Nonfinal Office Action dated Jul. 24, 2008, 15 pages.
Park, et al.; "Linking Gene Expression Data with Patient Survival Times Using Partial Least Squares"; Bioinformatics; 18; pp. S120-2127; (2002).
U.S. Appl. No. 11/010,716 Final Office Action dated Nov. 13, 2009; 31 pages.
Hoggart, et al.; "Control of Confounding of Genetic Associations in Stratified Populations"; Am. J. Hum. Genet.; 72; pp. 1492-1504; (2003).
Jonsson, et al.; "Automated Covariate Model Building Within NONMEM"; Pharmaceutical Research; 15; pp. 1463-1468; (1998).
Schaid, et al.; "General Score Tests for Associations of Genetic Markers with Disease Using Cases and Their Parents"; Genetic Epidemiology; 13; pp. 423-449; (1996).
Prentice, R. L.; "Logistic Disease Incidence Models and Case-Control Studies"; Biometrika; 66; pp. 403-411; (1979).

* cited by examiner

*Primary Examiner*—Shubo (Joe) Zhou
(74) *Attorney, Agent, or Firm*—Cantor Colburn LLP

(57) ABSTRACT

A physiogenomics method for predicting an individual's response to an environmental stimulus comprises producing and recording a physiogenomic model. The model is produced b a method including selecting a plurality of genetic markers, identifying significant covariates among demographic data to produce correlated markers for use as a covariate in an unadjusted association test; performing for the plurality each selected genetic markers an unadjusted association test; using permutation testing to select a plurality of model building markers; identifying one or more genes not associated with a particular outcome in the individual to serve as a physiogenomic control; and presenting a display of the individual's predicted physiological response. One can then compare the genetic markers of the individual to the physiogenomic database and convey to the individual an appropriate treatment intervention.

23 Claims, 5 Drawing Sheets

Multi-Gene SNP Ensemble places test individual C1 at 86th percentile risk rating

SEQUENCE LISTING

<160> NUMBER OF SEQ ID NOS: 384

<210> SEQ ID NO 1
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: M=A or C
<220> FEATURE:
<221> NAME/KEY: misc_feature
<222> LOCATION: (22)..(22)
<223> OTHER INFORMATION: m = a or c

<400> SEQUENCE: 1
actgctctct agttggaaag amgaaaggat aaggttggag ga          42

<210> SEQ ID NO 2
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 2
caagagaatg gccactggtc amctaccgtg ccaacctgcc aa          42

<210> SEQ ID NO 3
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 3
ctttacaaca ggcataaatt awttcttcag agaagttcaa tt          42

<210> SEQ ID NO 4
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 4
tcccctcctc aggtggacgg crtgctagaa aactggatct gg          42

```
<210> SEQ ID NO 5
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 5
gcagatgtct ttgtaaaact crtctcttta ttctggaaat ta                          42

<210> SEQ ID NO 6
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 6
agtttcatgt acattaaata traatttctt ttggctggaa at                          42

<210> SEQ ID NO 7
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 7
ccttactcag agtctctctg crcccagtgt gctagccttg tg                          42

<210> SEQ ID NO 8
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 8
cctaaatgcc aagtcggctt trttatcatt gtggttgctg ct                          42

<210> SEQ ID NO 9
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 9
agctttcaaa tgtcatgcat trtgtggcag gagtaggttt ta                          42

<210> SEQ ID NO 10
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g
```

```
<400> SEQUENCE: 10
aagagtccat tcaaaagggt trtacagaca gaaaaccagt gg                            42

<210> SEQ ID NO 11
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 11
tgctcagcct tcttcaatga crgtgttttg ctattgtctc ta                            42

<210> SEQ ID NO 12
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 12
ttgtttttca agttttgatt tmtctgctaa aattcagacc tg                            42

<210> SEQ ID NO 13
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 13
ctctccctcc tgtcctctcc crcaagtaga ctgagggcag ct                            42

<210> SEQ ID NO 14
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 14
agcgggcttc ctcttgaaca crgtcctcaa tgctcctctt cc                            42

<210> SEQ ID NO 15
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 15
gacagagaga ggacccaagc asgcaactag ttggaggact tg                            42

<210> SEQ ID NO 16
<211> LENGTH: 42
<212> TYPE: DNA
```

<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 16
tttcaactcc ttcctgcagt crttccaggt ggggcctgtg ac                              42

<210> SEQ ID NO 17
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 17
ctcccctctc agttcagggc tmtcttgggt ccctgccagc tg                              42

<210> SEQ ID NO 18
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 18
ccctcatctg aaacaagaac trgaggcctg ggctgctcct cc                              42

<210> SEQ ID NO 19
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 19
ttcaaggtca agttctttgg tragaaggtc ctagctgcat tg                              42

<210> SEQ ID NO 20
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 20
taaaaaacta agcccgcct gmgtcttgtt aatgaatgat ag                               42

<210> SEQ ID NO 21
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 21
gcataaagga agaaaccatc aratggttca gaattggtaa ga                              42

<210> SEQ ID NO 22
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 22
cagtgctgac caggtggcca crgtgatgtg ggactacttc ag        42

<210> SEQ ID NO 23
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 23
ccgtgctctt aaccatctgc craacttgca ctgccagtca tt        42

<210> SEQ ID NO 24
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 24
ttcacatact ggggagttca gmatagtaat gttttggaa aa        42

<210> SEQ ID NO 25
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 25
agcaaactga ggcacagaga trttacatca cctgtacaag gg        42

<210> SEQ ID NO 26
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 26
ccagccagcg ctgggatgtg crggaggacg gggacagcat tc        42

<210> SEQ ID NO 27
<211> LENGTH: 42
<212> TYPE: DNA
<213> ORGANISM: Homo Sapiens
<220> FEATURE:
<221> NAME/KEY: misc_feature
<222> LOCATION: (22)..(22)

<223> OTHER INFORMATION: s = c or g

<400> SEQUENCE: 27
tactggtgct gacgcctggc csgccggccg cgggactatc ca                              42

<210> SEQ ID NO 28
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 28
acccaataag gtgagtggat grtacatgga gaaggaggga gg                              42

<210> SEQ ID NO 29
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 29
tcctgtgaga gagttgagag crataatttt agggtggtta tt                              42

<210> SEQ ID NO 30
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 30
aagctgctgt aaatggaggc trcctagaga ggagagggcc tg                              42

<210> SEQ ID NO 31
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 31
ggagagagca gccccctcaaa crcagcccct gggcaaggag ac                             42

<210> SEQ ID NO 32
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 32
ctagcacatc tcttgcccga grgcctcagc gcttgctgtc gc                              42

<210> SEQ ID NO 33
<211> LENGTH: 42

<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 33
aaactaggaa ttacatggta arttgaaaga ggaagttagg gg                             42

<210> SEQ ID NO 34
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 34
aaagagctct tttgtctttc artatctctt ccctgtttgg ac                             42

<210> SEQ ID NO 35
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 35
tctcttgaag gtgggtgggc crctaccacc aagaatatct cc                             42

<210> SEQ ID NO 36
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 36
gccactgagg gagaaggcca crgacgtgat gccgcagatg at                             42

<210> SEQ ID NO 37
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 37
atcttttaga gtccgacctc trgaaatgtg tgtatgatgt ga                             42

<210> SEQ ID NO 38
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 38
cgaagcatat tacccatgaa crcatatatc cacatgtatg ac                         42

<210> SEQ ID NO 39
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 39
tgcaaagttc tgtgacaata crtactcggg ctagaggtga ct                        42

<210> SEQ ID NO 40
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 40
cggggctggc tctcattgct grccttcact gtgcactgtg ag                        42

<210> SEQ ID NO 41
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 41
ggtgttgggc ttcagcagga crttgatgcc ccccacgatg gc                        42

<210> SEQ ID NO 42
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 42
cactgtactt actgctaaag gracccaaac ggtccattcc ct                        42

<210> SEQ ID NO 43
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 43
atctttctgc cacaccacct crccctcctt tctcaaggtc tt                        42

<210> SEQ ID NO 44
<211> LENGTH: 42
<212> TYPE: DNA
<213> ORGANISM: Homo Sapiens
<220> FEATURE:
<221> NAME/KEY: misc_feature

```
<222> LOCATION: (22)..(22)
<223> OTHER INFORMATION: w = a or t

<400> SEQUENCE: 44
aaactgagtc ccagaaggat twagtcagtt acccaagttg tt                42

<210> SEQ ID NO 45
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 45
cacggagact tatgcaccag artgaaatgc tgagatgttc tt                42

<210> SEQ ID NO 46
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 46
gtcaagggta taacacctta grgtataatt tgttacagtg tt                42

<210> SEQ ID NO 47
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 47
tgcatgagtg tgtccgtgtc crtggggtg attgtgggta ag                 42

<210> SEQ ID NO 48
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 48
agaatttgta tctcacacca artaattttt aaaaaggtca tt                42

<210> SEQ ID NO 49
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 49
atgatgtgtg tggggagga araagcttat caaatcaaag cc                 42

<210> SEQ ID NO 50
```

<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 50
agtttgagac gtgggtgaaa crtaggtgga aaagtccagc aa					42

<210> SEQ ID NO 51
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 51
gagaaagaga gccaggacaa gwctctctcc ctccctgagc tg					42

<210> SEQ ID NO 52
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 52
ctctccagtg tggccaagat craagatgta cctggtgacc cc					42

<210> SEQ ID NO 53
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 53
ctatcctcaa atgctatata amccaactgg tggaaaaaaa tt					42

<210> SEQ ID NO 54
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 54
agtgaatgag atagcagaca amccagatgc ctaccgacag gt					42

<210> SEQ ID NO 55
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 55
ttgctgcctc cgccagcga argccccgag ccgctgtctc ag                42

<210> SEQ ID NO 56
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 56
gtgtgtgcct ctttgatgga traagtggcc aatcacctag gc                42

<210> SEQ ID NO 57
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 57
gcaggtctcc acacacctgc crtccaggta gaagttgcgg ca                42

<210> SEQ ID NO 58
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 58
tgaatggctg aattatgata trtacattcc tgatcttcct cg                42

<210> SEQ ID NO 59
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 59
aacaaagatt ctcctttcct crttcaccac tttcttgctg tt                42

<210> SEQ ID NO 60
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 60
atagtgtgga cattgaaaga tmccctgacc ttccctatgt tt                42

<210> SEQ ID NO 61
<211> LENGTH: 42
<212> TYPE: DNA
<213> ORGANISM: Homo Sapiens
<220> FEATURE:

<221> NAME/KEY: misc_feature
<222> LOCATION: (22)..(22)
<223> OTHER INFORMATION: r = a or g

<400> SEQUENCE: 61
aaaagtgttt cccagaaacc crccatccct ttatccttt at                          42

<210> SEQ ID NO 62
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 62
cagactctag agactgaaat tsaaggccca gttcttgctg tt                         42

<210> SEQ ID NO 63
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 63
tacctacgtt tgcaacactt crtgtttata agccatcagc tg                         42

<210> SEQ ID NO 64
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 64
ttcagtttca tctaacgtca craagaacgc tgctttctcc ac                         42

<210> SEQ ID NO 65
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 65
ttagggactt tcaaaaactc asactcttgg gttctgaccc tg                         42

<210> SEQ ID NO 66
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 66
tgggagttgg ccatgcagct csgggccgac ggagcagaac gc                         42

```
<210> SEQ ID NO 67
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 67
gccttcttgc tggcacccaa trgaagccat gcgccggacc ac                            42

<210> SEQ ID NO 68
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 68
ttgccaggag ctgaggtctg crggaggaga gttgtgagtg aa                            42

<210> SEQ ID NO 69
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 69
ccagcagggc cttgtagctg artacaccag agatgaggct gg                            42

<210> SEQ ID NO 70
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 70
agtgggaagc agcaacatag artggctttt caagaaataa ac                            42

<210> SEQ ID NO 71
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 71
cagcactccg aatgaaggct grcagtgaaa ctgaattact ta                            42

<210> SEQ ID NO 72
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g
```

<400> SEQUENCE: 72
atgccgggtg ctagagatac arcagtgaac atgacaaagt tc                              42

<210> SEQ ID NO 73
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 73
gagaactgag ggggtgggag grgaagagag tgccggcggc tc                              42

<210> SEQ ID NO 74
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 74
gattaaatgc attctgccac arttctcatt attttcatag tc                              42

<210> SEQ ID NO 75
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 75
cacccgccat caatcctgcc grctctggcc gctctgcctc at                              42

<210> SEQ ID NO 76
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 76
accagaagct agcataatgg artatcgccc ctcactttgt tc                              42

<210> SEQ ID NO 77
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 77
cgtcagaaat gtgtggtggg gmcatattag tggtgacagg tt                              42

<210> SEQ ID NO 78
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 78
ggctggttgg agcctctccc crggcagcag ccctggtgga ga                              42

<210> SEQ ID NO 79
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 79
ccttctctct tgggccaagg artttctgct ctattgcatg tt                              42

<210> SEQ ID NO 80
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 80
aacctcactt aacattttgg crtgggaatg gcaattatct gc                              42

<210> SEQ ID NO 81
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 81
gattttgccc agtggctctc craggtggct gtactgatgg ac                              42

<210> SEQ ID NO 82
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 82
gatgtggata ctgagcctcg crgcttatat gattgctcac ag                              42

<210> SEQ ID NO 83
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 83
ggtactgcac caggcggccg crcacgtcct ccatgtccgc gc                              42

<210> SEQ ID NO 84
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 84 tgggtcccccc cgcacagagc crtcctgctg ccggtagccc gc                42

<210> SEQ ID NO 85
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 85
ccggagtctc tcatgccgct crgggtccag gcccggggtg ga                42

<210> SEQ ID NO 86
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 86
caaacccttt ccactccatt awaagaacat gaatcctgat aa                42

<210> SEQ ID NO 87
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 87
ctgggagatt ctcctattga cscagaaagc gattccttca ct                42

<210> SEQ ID NO 88
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 88
ttttgtccag aaaagtgaac cwggtcaatg gattatttat ga                42

<210> SEQ ID NO 89
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

```
<400> SEQUENCE: 89
aggacccatc ctggatcatc cratgagcag ccgtggcgct cg                              42

<210> SEQ ID NO 90
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 90
ctccggacgg gcacagagag gmtttatagt ggttgagacc ca                              42

<210> SEQ ID NO 91
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 91
tcttcttgcc ctacatactt craaagccct tggagaaatc ct                              42

<210> SEQ ID NO 92
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 92
cggatggtgg atttcgctgg crtgaaggac aaggtgtgca tg                              42

<210> SEQ ID NO 93
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 93
gtcagcacct ggaagccccc artgaaggaa ccatggactg tg                              42

<210> SEQ ID NO 94
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 94
gttccagggt atatctcaga gmctggagaa cgtgtctggt ta                              42

<210> SEQ ID NO 95
<211> LENGTH: 42
<212> TYPE: DNA
```

```
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 95
gattttgtca aagatagatt crggagccat ccatttcaga gg                    42

<210> SEQ ID NO 96
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 96
aggaccctgg accccgaag gmaaggccgg cttcctctgg gt                     42

<210> SEQ ID NO 97
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 97
agcctcgtta tcccatgtgt craagaagat aggttctgaa at                    42

<210> SEQ ID NO 98
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 98
aaagaatctt gtccccaaca grttctgggt ataaccaacc ct                    42

<210> SEQ ID NO 99
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 99
acagccatag agacaagggc argagagagg cgatttaata ga                    42

<210> SEQ ID NO 100
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 100
acgctgggct gcacgctacc crccaggtcc cctgccactg cc                    42
```

<210> SEQ ID NO 101
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 101
tgtgtaactc gaccctgcac crgctcactc tgttcagcag tg                              42

<210> SEQ ID NO 102
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 102
gttagagact gaaagctttc aratgaacag aattgatact gg                              42

<210> SEQ ID NO 103
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 103
ggcaggtaat gatattgtga crtggagaat gtgcacttag aa                              42

<210> SEQ ID NO 104
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 104
ggctccacga caatgagtac arctgtggtc cgtggcttct tg                              42

<210> SEQ ID NO 105
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 105
aaggggactg tgagaaaaaa artgttcatg aggctcgagt cc                              42

<210> SEQ ID NO 106
<211> LENGTH: 42
<212> TYPE: DNA
<213> ORGANISM: Homo Sapiens
<220> FEATURE:
<221> NAME/KEY: misc_feature
<222> LOCATION: (22)..(22)

<223> OTHER INFORMATION: r = a or g

<400> SEQUENCE: 106
cagttcagtt ggttttagta trttcagagt tgtgcatcca tc    42

<210> SEQ ID NO 107
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 107
gttggctcta ctcatttcct crtcgtcatt ctcttgtagt ca    42

<210> SEQ ID NO 108
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 108
agaatggtgg tgtcttcttc arttgatgga gaagcgcagc cg    42

<210> SEQ ID NO 109
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 109
aattagattg gaatggatgt awccgtgtat attcataccc tt    42

<210> SEQ ID NO 110
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 110
attttcttga cccctactta cratcctggg agatgtattt gg    42

<210> SEQ ID NO 111
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 111
cttggtggcg tgcttcatgt arccctgcat gaagctgaga ag    42

<210> SEQ ID NO 112
<211> LENGTH: 42

```
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 112
cgccccttta cctttccatg grttagatga aggagcgtag gt                                 42

<210> SEQ ID NO 113
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 113
gctcttagaa ctagctacaa aratatttca tatgtttatg tc                                 42

<210> SEQ ID NO 114
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 114
acttgtaatt atgcgtggag twgttaactg tatttttac ac                                  42

<210> SEQ ID NO 115
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 115
tgctcaccct aggatggagg grgcagtggg ggctggttag ga                                 42

<210> SEQ ID NO 116
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 116
gcctgtacca atacatcctg cmgtggccac ggtgaatgtg ta                                 42

<210> SEQ ID NO 117
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 117
``` gcaagccta ttagacatat amttttccca actttcccct tt                    42

<210> SEQ ID NO 118
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 118
gggtaggaaa ttaagtgaat amttttgtg atccaagaaa ga                    42

<210> SEQ ID NO 119
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 119
cttttaagca acctacaggg gmagccctgg agattgcagg ac                   42

<210> SEQ ID NO 120
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 120
gaaatgagca agagatctga cwccaggagt ctttcctcat tt                   42

<210> SEQ ID NO 121
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 121
gcttccttat gtaaaatgta grtatttcta aagtaacgca at                   42

<210> SEQ ID NO 122
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 122
ctactggaag attagccacg trttgagttt tgtctttgca tt                   42

<210> SEQ ID NO 123
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g
<220> FEATURE:
<221> NAME/KEY: misc_feature
<222> LOCATION: (37)..(37)
<223> OTHER INFORMATION: n = a or c or t or g

<400> SEQUENCE: 123
actctgcacc ttcaggttca grcccttcaa gatctancag ga                                42

<210> SEQ ID NO 124
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 124
ttttccaaag atgatctctc crgagctatt gtttcttcat tc                                42

<210> SEQ ID NO 125
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 125
agattcctcc ctgtacgata gwgtcttact tttccacttt gc                                42

<210> SEQ ID NO 126
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 126
ccttctctat gctgcaacag crgatgattc ttcctcttcc ac                                42

<210> SEQ ID NO 127
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 127
cctagagaca tatctcagtt argttttagc ctcaccagta tt                                42

<210> SEQ ID NO 128
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 128

```
cagctgaaag aaagacaaat artagatacc cactgcatgg ct                               42
```

<210> SEQ ID NO 129
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 129

```
ttcttgagtc cgtctgtctg grtgggaacc cagtctttac ca                               42
```

<210> SEQ ID NO 130
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 130

```
accctgcatt ctgaggggtc trgagggaaa ctgacagctg tg                               42
```

<210> SEQ ID NO 131
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 131

```
taatggagat actatgaaaa asgagaaaaa tgtcacttta ct                               42
```

<210> SEQ ID NO 132
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 132

```
tagtttgact caccttccca gmaccttcta gttctttctt at                               42
```

<210> SEQ ID NO 133
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 133

```
cagagcacga ggctgatttt cmatcccagt gtgggccaca cc                               42
```

<210> SEQ ID NO 134
<211> LENGTH: 42
<212> TYPE: DNA
<213> ORGANISM: Homo Sapiens
<220> FEATURE:
<221> NAME/KEY: misc_feature

```
<222> LOCATION: (22)..(22)
<223> OTHER INFORMATION: s = c or g

<400> SEQUENCE: 134
attaacccat ggtccagaaa tsatgggttg ttaaatgacc aa                              42

<210> SEQ ID NO 135
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 135
tacgattctc accccatatt twcaagccta gtccaaggat ta                              42

<210> SEQ ID NO 136
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 136
ggctgctcag ggcctcgtcc amccccagcc tgacagagag ct                              42

<210> SEQ ID NO 137
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 137
ggcgccccct ggacttctgc trgaatttag atttaaatag at                              42

<210> SEQ ID NO 138
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 138
agtgcccgat atacattaag trcttaataa atgactgcta cc                              42

<210> SEQ ID NO 139
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 139
ctgaccccaa gagcgagggg arcccaactc tgtgctctca cc                              42

<210> SEQ ID NO 140
```

<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 140
gaccctgtaa ttttcagaaa crcacatagg agtgggtgtc tg                              42

<210> SEQ ID NO 141
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 141
tacctggacg ctggctgccc cmcggtcaga ggtctgggt cc                               42

<210> SEQ ID NO 142
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 142
caggctcagg gtctaaattc crtatccttt cttccatacc ct                              42

<210> SEQ ID NO 143
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 143
tgctccaaag tctatcacaa tratcctctt ttccataaag cc                              42

<210> SEQ ID NO 144
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 144
tttagacata tgcctctata tscttctata attattaata gt                              42

<210> SEQ ID NO 145
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 145
ctcagttcct ctgctgtctc crtccttgcc ccatcctcca gg    42

<210> SEQ ID NO 146
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 146
tttcctaatt ttgcagttga grtttaagag gttgggaact gg    42

<210> SEQ ID NO 147
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 147
atggggccct ggggagagag crtggcaagt tctcagcatt cg    42

<210> SEQ ID NO 148
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 148
cgggaagctt gcaagacgct crgcttccta ttgcaagacc gc    42

<210> SEQ ID NO 149
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 149
gcttgtcgat tgcttatcca gwgcctacag ctccaggaag cc    42

<210> SEQ ID NO 150
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 150
cacacactaa catgcagaaa crtactacct cacactcaaa tg    42

<210> SEQ ID NO 151
<211> LENGTH: 42
<212> TYPE: DNA
<213> ORGANISM: Homo Sapiens
<220> FEATURE:

```
<221> NAME/KEY: misc_feature
<222> LOCATION: (22)..(22)
<223> OTHER INFORMATION: r = a or g

<400> SEQUENCE: 151
acaatctggg ctatgagatc artaaagtca gagccaaaag aa                             42

<210> SEQ ID NO 152
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 152
ttcagcagga gctgggccct crggcccagt ggctgggctg ga                             42

<210> SEQ ID NO 153
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 153
gatatcgtga ctaccgtcca gscctcctat tctaagaaaa gc                             42

<210> SEQ ID NO 154
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 154
tagcttatca ggtttattgc tstccatctg tatcacctgc ct                             42

<210> SEQ ID NO 155
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 155
cctgttttat gagattttaa cmccttacct tgattcctag ga                             42

<210> SEQ ID NO 156
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 156
agccccagtc cttaccggaa crgtagaggc ttaacaaaca tt                             42
```

```
<210> SEQ ID NO 157
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 157
caagagctcc ctacccagga arcccaagcc tcacccagaa tg                              42

<210> SEQ ID NO 158
<211> LENGTH: 42
<212> TYPE: DNA
<213> ORGANISM: Homo Sapiens

<400> SEQUENCE: 158
cccttgggaa cgcggcccga arcccaggat ctgggtgatg gg                              42

<210> SEQ ID NO 159
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 159
ccttttaatg gccatcaata amacagcctg actagttcaa ca                              42

<210> SEQ ID NO 160
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 160
aaactgacct ccaacatgga tratggggac cgacttgtgg gg                              42

<210> SEQ ID NO 161
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 161
aaataaaaag aatgcagccc artgtggggt aagtaaaagg at                              42

<210> SEQ ID NO 162
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 162
gagaagctcc catctagctg trtatgatag ggggtttatc tg                              42
```

<210> SEQ ID NO 163
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 163
ggttagggag actagcaatt arttgagaag atgtagtttg ac        42

<210> SEQ ID NO 164
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 164
tgcctgattt tgtcactgaa cratgagcat gatttttcca gg        42

<210> SEQ ID NO 165
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 165
ctcataaaga gccagacaaa argaaaaaaa acccagaaat ta        42

<210> SEQ ID NO 166
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 166
ggaatctcac aggccttcac cmctctcccc tgccctttct ca        42

<210> SEQ ID NO 167
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 167
tgggacaggt gcgctcccag amgggatcct gtcgccagtt ct        42

<210> SEQ ID NO 168
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

```
<400> SEQUENCE: 168
gggtgtgccc tctagattta gscagagatc tatccagtgt at                42

<210> SEQ ID NO 169
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 169
tagtaaacta tttcttccca trggagaaga tggattcttt tc                42

<210> SEQ ID NO 170
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 170
gccccacatc tgtgccacag asacagaccc tgggatcctc ag                42

<210> SEQ ID NO 171
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 171
cttgttcatg atgagattat asctgatctg acgtgagaat gc                42

<210> SEQ ID NO 172
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 172
ggtgcctctg tacaaccatg tstctcttct ctgctgtctg ct                42

<210> SEQ ID NO 173
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 173
agcaacgtct tgctgttttt crgaggtaga gggctgcttt ct                42

<210> SEQ ID NO 174
<211> LENGTH: 42
<212> TYPE: DNA
```

```
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 174
gccccaccca ctctcctgac twtcgggagc aaaccagtag ag                42

<210> SEQ ID NO 175
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 175
aatgaccggt tatactcttc trtaaaggaa tcctggaggt gt                42

<210> SEQ ID NO 176
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 176
tagccatact ccagaaaaaa tmaataaatt cccttggccc ca                42

<210> SEQ ID NO 177
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 177
ttcaacaagc ctgcttactg crgttagttg tgaccattgt ct                42

<210> SEQ ID NO 178
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 178
atgatctcag aggctgtata cmcacccaga gttattttat gc                42

<210> SEQ ID NO 179
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 179
cacaacaagg gtttagctct arggagagca gaggcaggat ga                42
```

<210> SEQ ID NO 180
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 180
attgagtggc tggggcctgg crcagccaga aatgacagtg gc                                   42

<210> SEQ ID NO 181
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 181
gccaatgcag atttatcctc crcccttctc caacctgttc ta                                   42

<210> SEQ ID NO 182
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 182
tgctcactat atgccaatag crtcccacaa ccactgattg tg                                   42

<210> SEQ ID NO 183
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m= a or c

<400> SEQUENCE: 183
cagaaagatg tcatcatcca gmattgcgtc cacacagtca ac                                   42

<210> SEQ ID NO 184
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 184
gagcgagagg acgctattgc artgccacgt gaagtgaatt gt                                   42

<210> SEQ ID NO 185
<211> LENGTH: 42
<212> TYPE: DNA
<213> ORGANISM: Homo Sapiens
<220> FEATURE:
<221> NAME/KEY: misc_feature
<222> LOCATION: (22)..(22)

-continued

<223> OTHER INFORMATION: w = a or t

<400> SEQUENCE: 185
gcacctcctg tgaccagccc awgttgttgg gcatagagac cc                42

<210> SEQ ID NO 186
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 186
ctggttggga gccttcccga crtgaacaag atgctggata ag                42

<210> SEQ ID NO 187
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 187
cgaacaagga cgctttgaag argtggaatt actgtgcaag ga                42

<210> SEQ ID NO 188
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 188
cttcccagtt gcactaacag arcctttgat tcagttcagc aa                42

<210> SEQ ID NO 189
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 189
ctctctcgtt tgggaaaaat arcggaagaa ctagtgtatc ct                42

<210> SEQ ID NO 190
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 190
ggagggaaat taaaatgaag artcaatgag attgcacatg aa                42

<210> SEQ ID NO 191
<211> LENGTH: 42

```
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 191
ggattgcaat aaagggaagg awgaaggatg attttggctt ga                              42

<210> SEQ ID NO 192
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 192
taccacgtac ctgctcatgg gmcactgggc tctgggcacg ct                              42

<210> SEQ ID NO 193
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 193
atgtgaataa taaggataat artcaccaaa tacatagaca tg                              42

<210> SEQ ID NO 194
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 194
tctgcccctt tgggctgcag cmtcacaagc tgtgtggcgt tg                              42

<210> SEQ ID NO 195
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 195
cccattcaga tgcactggta cmgggccacc caccaggaag cc                              42

<210> SEQ ID NO 196
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 196
```
ctgcaggtgc acggtttcct gmttgccag gtgtctctga gc                               42

<210> SEQ ID NO 197
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 197
gaggacacct cgcccagtaa tmcagacacc ctcctccatt ct                              42

<210> SEQ ID NO 198
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 198
tctggttgaa taaaggttct traaaacctc ctgagtcagg ac                              42

<210> SEQ ID NO 199
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 199
tctgggaaat gcaaggcaca crgccaagtg tggtgggggt ag                              42

<210> SEQ ID NO 200
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 200
agtggtcagg cttcacccag trctacagag cagatctggg ac                              42

<210> SEQ ID NO 201
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 201
cggcaattag actggctaga gmcacctcag tcaggctctc cc                              42

<210> SEQ ID NO 202
<211> LENGTH: 42
<212> TYPE: DNA
<213> ORGANISM: Homo Sapiens
<220> FEATURE:
<221> NAME/KEY: misc_feature

```
<222> LOCATION: (22)..(22)
<223> OTHER INFORMATION: r = a or g

<400> SEQUENCE: 202
cctgaggatg aagggcgtc crtggccagg cagcagtgag aa                        42

<210> SEQ ID NO 203
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 203
ggaaggaacc tcgtacatcc trcggggcag tggggacagc gt                       42

<210> SEQ ID NO 204
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 204
attctctttc tccctttctt craaacaggc cctgaagtat ga                       42

<210> SEQ ID NO 205
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 205
ttcttgaaga ccaaagtaga artccttaga ataactcatt ct                       42

<210> SEQ ID NO 206
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 206
ggtgggggct gaccgcaagc crcgccttct gtgcacctgg tc                       42

<210> SEQ ID NO 207
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 207
ccagcaaaca ccaggctacc amggatccca aagatgccaa aa                       42

<210> SEQ ID NO 208
```

```
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 208
tggcttcagc ttgtaaagct trgaaacatt ctgaaacaac at        42

<210> SEQ ID NO 209
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 209
gcctgtggtc acagagctcc tragtggcag aactcaactt ga        42

<210> SEQ ID NO 210
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 210
ccatactgaa aatgctagtc crccaagcac actttgagat ca        42

<210> SEQ ID NO 211
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 211
tgaaatcctt ttccctgctt tmctccagca cttggggat gt         42

<210> SEQ ID NO 212
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 212
aattatatct tattattaaa astctaccaa ctcaaagctt cc        42

<210> SEQ ID NO 213
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 213
```

```
caaagggtga gctctgtggg cmcaggacgc atggtagatg ga                    42

<210> SEQ ID NO 214
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 214
ctcattggcg caagagcagc crccagttat ggctcactcc ct                    42

<210> SEQ ID NO 215
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 215
agctaccttg gccagcgagt graagactcg ctcagagaac ca                    42

<210> SEQ ID NO 216
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 216
tctagaaggc atccaggcct crcctctttc atgtgcagct tt                    42

<210> SEQ ID NO 217
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 217
caacttcttt gtcatctcct trgctgtgtc agatctcttg gt                    42

<210> SEQ ID NO 218
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 218
acatgtgtac acgtggtgta trttaaaaac ttcaggctct ct                    42

<210> SEQ ID NO 219
<211> LENGTH: 42
<212> TYPE: DNA
<213> ORGANISM: Homo Sapiens
<220> FEATURE:
```

```
<221> NAME/KEY: misc_feature
<222> LOCATION: (22)..(22)
<223> OTHER INFORMATION: r = a or g

<400> SEQUENCE: 219
tgcagaaaac ccttcacccc crtgtcaaaa ggagctgacg aa                              42

<210> SEQ ID NO 220
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 220
ggagagggaa aaataaagtt awtgcatgtc ccagtttcct ca                              42

<210> SEQ ID NO 221
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 221
tttccttcca atatattcta crtaagttcc cggaaagtcc cc                              42

<210> SEQ ID NO 222
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 222
ttctactccc tcttcccctt awtgaaggat gctgtgtgta ca                              42

<210> SEQ ID NO 223
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 223
gcaacccgga catggacact cscacagtgg tgaggaagag ac                              42

<210> SEQ ID NO 224
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 224
acagctcctg ttgccatagg arggagctgg gtgagatact ag                              42
```

```
<210> SEQ ID NO 225
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 225
aaaaactttt tctgatccct tmcttttgaa aagcccatta at                         42

<210> SEQ ID NO 226
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 226
tgcgcgcgca gcagagcagt csctggaagg ccttgcggaa gt                         42

<210> SEQ ID NO 227
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 227
cttttcacag gaaatttct trggagtcta ttgtcactgt ct                          42

<210> SEQ ID NO 228
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 228
cgcatcggcc tctatgactc crtcaagcag gtgtacaccc cc                         42

<210> SEQ ID NO 229
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 229
acaccgcggt actgggcgct grctgtagcg cgcactggcc cc                         42

<210> SEQ ID NO 230
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g
```

<400> SEQUENCE: 230
tgcaatgaaa tgctctgtcg grttggggtt gtctaattgc ct        42

<210> SEQ ID NO 231
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 231
tcatcaatcc atgaaactta gmataatact gataaattga at        42

<210> SEQ ID NO 232
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 232
cattgcgtat tatcaggaaa araatactgt ctattaaaga aa        42

<210> SEQ ID NO 233
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 233
ctcatcarct tctacatccc crttgccatc atgatcgtga cc        42

<210> SEQ ID NO 234
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 234
atgcgggtgg ggaggtgaga grttggcgac attgacggga gg        42

<210> SEQ ID NO 235
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 235
taaagtttga cttttcctat tsgtagctca cttgaagaca aa        42

<210> SEQ ID NO 236
<211> LENGTH: 42
<212> TYPE: DNA
<213> ORGANISM: Homo Sapiens

```
<220> FEATURE:
<221> NAME/KEY: misc_feature
<222> LOCATION: (22)..(22)
<223> OTHER INFORMATION: r = a or g

<400> SEQUENCE: 236
gaccagggct tctgaactgc araggtgctt tttcctaaaa cc                             42

<210> SEQ ID NO 237
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 237
aagggcattt gcattcaaag grttctaaac ggaaaatgac aa                             42

<210> SEQ ID NO 238
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 238
agacttcccc aggaaagtcc tmtgtgtctt gtatttggtt ac                             42

<210> SEQ ID NO 239
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 239
atgttcatga gagcaaacct crtgccaatg cagtttctgg gt                             42

<210> SEQ ID NO 240
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 240
agtgaggctt ggaaaggcgt crtggacaga cctgggtcgc tt                             42

<210> SEQ ID NO 241
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 241
cttcaaaaag tgaaactaac tmctcgtttc tggtaaagag cc                             42
```

```
<210> SEQ ID NO 242
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 242
ccagtttaaa aatacatcat argtaaggca atgagaagag tt                              42

<210> SEQ ID NO 243
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 243
atgaattgtc actcagaaga arcttaatag gcattaatac ta                              42

<210> SEQ ID NO 244
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 244
tgctttgagc aagggtaccc crctctgaga attcccagcc at                              42

<210> SEQ ID NO 245
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 245
ttctgcttaa atatggcttg tscattataa cataagttag gc                              42

<210> SEQ ID NO 246
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 246
tttccctcta ctcagttatc crattattca tgactagatg ag                              42

<210> SEQ ID NO 247
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t
```

<400> SEQUENCE: 247
ccatagatcc aaacatcttt awctatccat gtatttgagt ag                              42

<210> SEQ ID NO 248
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 248
tcaagggcct tgctgggggc aracaaggtg gaacataaca cg                              42

<210> SEQ ID NO 249
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 249
ttgtcccagt tgccaagtga grggtgtgat ctcatttcct ag                              42

<210> SEQ ID NO 250
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 250
attttcttct gggtggccct aractgcttt cttttccccc at                              42

<210> SEQ ID NO 251
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 251
ctcaggaggc cttactgtgc crtggttctt gccctttgat tt                              42

<210> SEQ ID NO 252
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 252
aaccaattct ggcctttaaa gmagtctctt tatctcattc cc                              42

<210> SEQ ID NO 253
<211> LENGTH: 42
<212> TYPE: DNA

<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 253
gccttcccct tagagaagag crcctgccag acaagggaga ag            42

<210> SEQ ID NO 254
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 254
ttctgcagag cttcttctcc trtctcccac atgactaatg tt            42

<210> SEQ ID NO 255
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 255
atagggagtc atggagggtt tstgagcagg ccagggatta ga            42

<210> SEQ ID NO 256
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 256
cagaaggaag agttctgggg gmtcatctgg ggcctgcagc ag            42

<210> SEQ ID NO 257
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 257
caggattgta agcacccct gratccaggt aaggccaagt tt            42

<210> SEQ ID NO 258
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 258
accaaatatc tagggatcag araaattgat tcaggaaata ct            42

```
<210> SEQ ID NO 259
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 259
tctaagtcat agctcttgat trtggcccac ccccagtagg ga                          42

<210> SEQ ID NO 260
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 260
ttatgtcacc ctggggagta aragaatggt cttcctgctc ct                          42

<210> SEQ ID NO 261
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 261
atctgccggt gattcaacag crtgcggaac ctgcatgacg tt                          42

<210> SEQ ID NO 262
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 262
gtagtgtagc accagggtcc crtggtgctg ctgtcggggt tg                          42

<210> SEQ ID NO 263
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 263
cctccggggc gtcttatggc cmccatgccg ctccagcgcg gc                          42

<210> SEQ ID NO 264
<211> LENGTH: 42
<212> TYPE: DNA
<213> ORGANISM: Homo Sapiens
<220> FEATURE:
<221> NAME/KEY: misc_feature
<222> LOCATION: (22)..(22)
```

```
<223> OTHER INFORMATION: r = a or g

<400> SEQUENCE: 264
gacacagcac acaaccaccc grcctgttcc cgacacctcc cg                              42

<210> SEQ ID NO 265
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 265
taggaatggg caaatgaagt grccttctgc cccagcctct ct                              42

<210> SEQ ID NO 266
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 266
gctcaaagac cacgggcggg tsccaggggt cgttctggtg gt                              42

<210> SEQ ID NO 267
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 267
catagctttg ttagctatgc crgtaattaa caggcataac tc                              42

<210> SEQ ID NO 268
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 268
agccaggagc tttcctgggc gmttttgta caggatctca tt                              42

<210> SEQ ID NO 269
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 269
tgatttcttg catactttat tragcaaaat ccatgagaag tg                              42

<210> SEQ ID NO 270
<211> LENGTH: 42
```

```
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 270
tgagatctag tagaaggaca crtcttgaat tgggtcatgc tt                              42

<210> SEQ ID NO 271
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 271
tggggacaga ggctaaatac trccccctcc cctttctac tt                              42

<210> SEQ ID NO 272
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 272
tttgcaagca ctttctcttc trcacgtttg gaacctaccc cg                             42

<210> SEQ ID NO 273
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 273
ttataaactg acacacacac amaaaaaatc cacacacact tt                             42

<210> SEQ ID NO 274
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 274
aggagctcgg agcaagaagg crcccaccga gagcgtctga ag                             42

<210> SEQ ID NO 275
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 275
```
taataaatat taagggtgac crgtgactca ggctctgcct ct                             42

<210> SEQ ID NO 276
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 276
ctgcagaagc aaggccaata artctctcaa aatgcagttc aa                             42

<210> SEQ ID NO 277
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 277
agtcaacata tatttgagag amcttcaact tatcaagtat tg                             42

<210> SEQ ID NO 278
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 278
ggtgaagagg ctgatggggc cmagcaggtc acagagctca tc                             42

<210> SEQ ID NO 279
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 279
agaagctctt tcatgttgtc artttagaa atccaaatca tt                              42

<210> SEQ ID NO 280
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 280
cacgttgacg atgttgagca crtagaaggg catccagcag ag                             42

<210> SEQ ID NO 281
<211> LENGTH: 42
<212> TYPE: DNA
<213> ORGANISM: Homo Sapiens
<220> FEATURE:
<221> NAME/KEY: misc_feature

```
<222> LOCATION: (22)..(22)
<223> OTHER INFORMATION: s = c or g

<400> SEQUENCE: 281
tgtgtgacat cccgacagaa asgcacttgt gaaatcgaca at                              42

<210> SEQ ID NO 282
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 282
agacacaggt gacccaactc cmatggctgg cctaggcccc tc                              42

<210> SEQ ID NO 283
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 283
ctccctagag ttacacacgc tmtctctccc gccaattgcc gg                              42

<210> SEQ ID NO 284
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 284
tttggatttt tccagccagg grttttttgtg tcctgttgct tt                             42

<210> SEQ ID NO 285
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 285
agtgttttcc aaggtgtgat traaaatgga gatttcttac ct                              42

<210> SEQ ID NO 286
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 286
ttccgctctc cctctgagag trtattactg tgcttcaata ca                              42

<210> SEQ ID NO 287
```

```
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 287
cattaggcac tgttttgttc craggaagat attgcaggag aa                              42

<210> SEQ ID NO 288
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 288
aatttcaact tataaacata crttgctata aatatgttca at                              42

<210> SEQ ID NO 289
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 289
agggactgga gcctgctgcc crgcacggtg gtcacaccct gg                              42

<210> SEQ ID NO 290
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 290
ggggatggag aaggcaggat gsggcaggag gccttgggggg ga                             42

<210> SEQ ID NO 291
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 291
cctgtaggat tgtgttcctc traaactgtc ccctaaatta tg                              42

<210> SEQ ID NO 292
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 292
```
tcaggtatta gcacttgaaa tmtaacttct ttatgaagct cc                              42

<210> SEQ ID NO 293
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 293
acagccttta cctaaggcag trctcttgct gacattcagg ac                              42

<210> SEQ ID NO 294
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 294
cccaaagctg agaagtggga crccccagca caccctcccc ca                              42

<210> SEQ ID NO 295
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 295
aactgaaagc agtttaatct crccagagcc actgaaggag tt                              42

<210> SEQ ID NO 296
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 296
catcaggatt atcagcattt argccagagt tgcaaattaa gt                              42

<210> SEQ ID NO 297
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 297
cggcctggta cactgccagg crcttctgca ggtcatcggc at                              42

<210> SEQ ID NO 298
<211> LENGTH: 42
<212> TYPE: DNA
<213> ORGANISM: Homo Sapiens
<220> FEATURE:

```
<221> NAME/KEY: misc_feature
<222> LOCATION: (22)..(22)
<223> OTHER INFORMATION: r = a or g

<400> SEQUENCE: 298
agactgggcc ctgcacctcc crgggctgct agcatttgca gg                               42

<210> SEQ ID NO 299
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 299
ggacactggt tccacctccg crtggctgta cagtgctgcc ga                               42

<210> SEQ ID NO 300
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 300
agcaccttaa ctatagatgg trtaacccgg agtgaccaag ga                               42

<210> SEQ ID NO 301
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 301
cagcacctag caaaataccc crtggtatga tgttcaaagt aa                               42

<210> SEQ ID NO 302
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 302
tcagatggaa aaatgaagtc crgattcatt ctgggtcttt cc                               42

<210> SEQ ID NO 303
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 303
acaaatgctc tgagtcacca crctgcggct cagatgctat ga                               42
```

<210> SEQ ID NO 304
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 304
cacacagcat caaggactcc artaagatgg tcccagcctc tt                            42

<210> SEQ ID NO 305
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 305
cactatcatt gattatttcc crggaaccca taacaaatta ct                            42

<210> SEQ ID NO 306
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 306
cacaaaggca acagaccgtg araatagatg ccaatgtgct ag                            42

<210> SEQ ID NO 307
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 307
cagttagaat tgtcaatcta grtggggaca actcattatt tt                            42

<210> SEQ ID NO 308
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 308
cttcttcagc tacagcctgg gmgccatctg cccgaagcac tg                            42

<210> SEQ ID NO 309
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

```
<400> SEQUENCE: 309
ttggctgaca ctttcgaaca crtgatagaa gagctgttgg at                    42

<210> SEQ ID NO 310
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 310
atcgacttca ttgtaaagaa arctggacag aagcagctac ac                    42

<210> SEQ ID NO 311
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 311
ggcaaagttt catctattag crataaaatg tgaattttct gc                    42

<210> SEQ ID NO 312
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 312
acttatttca gtggttcaaa amatttcttc aacgcttaac ca                    42

<210> SEQ ID NO 313
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 313
acccgcatct cccaccccca gracgcccct ttcgccccaa cg                    42

<210> SEQ ID NO 314
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 314
atcgaagtta cgcatccggt tragttccag ctggaaggcc ag                    42

<210> SEQ ID NO 315
<211> LENGTH: 42
<212> TYPE: DNA
<213> ORGANISM: Homo Sapiens
```

```
<220> FEATURE:
<221> NAME/KEY: misc_feature
<222> LOCATION: (22)..(22)
<223> OTHER INFORMATION: r = a or g

<400> SEQUENCE: 315
aaagtagaac ataccaggcc grgagaacaa catgtgctgc tt                              42

<210> SEQ ID NO 316
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 316
aaatctctct tcttcgataa asttcccagg aggtaaccca at                              42

<210> SEQ ID NO 317
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 317
aacaaatgta tctcatgtgt graccctgaa gacaaatgta ag                              42

<210> SEQ ID NO 318
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 318
aatcaaccaa gtggaagaaa gratatcaga gtctgaagac aa                              42

<210> SEQ ID NO 319
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 319
atcactcctc ttctagcatc trttacattt tctggcattt ct                              42

<210> SEQ ID NO 320
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 320
aacctgcgca tagtggtggc tracctgttc tctgccggga tg                              42
```

<210> SEQ ID NO 321
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 321 aggggcaac aggacacctg arggatggaa gggtcaggag gc        42

<210> SEQ ID NO 322
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 322
ggtggggtta gagggatgg trcctggcag tgtgcagcag ac        42

<210> SEQ ID NO 323
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 323
gcgtctttac agatccaaag craatttta aatctccagg ct        42

<210> SEQ ID NO 324
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 324
gtctttctcc agatgatgcc artttgtgg atgccattca ta        42

<210> SEQ ID NO 325
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 325
gccctggttt cctccagtat gmctgcaaaa tttcctctcc at        42

<210> SEQ ID NO 326
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

```
<400> SEQUENCE: 326
ccaatgtact ttcctgaatg crgccagaaa ctgagcccac cc                              42

<210> SEQ ID NO 327
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 327
gctgttgctg ctctggcctc trtgagcccc gggagtccgc ag                              42

<210> SEQ ID NO 328
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 328
atttgcaaag tatgtacagc arcccccct tatcctcagt gg                               42

<210> SEQ ID NO 329
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 329
ccctccttca atattgacct arcgggggag aaaagattta ga                              42

<210> SEQ ID NO 330
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 330
tttacgttct cgaggttcga trtcttggct acaagctcta aa                              42

<210> SEQ ID NO 331
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 331
gatgcaccta ctagacacct amtctgcgct agatggtggg gg                              42

<210> SEQ ID NO 332
<211> LENGTH: 42
<212> TYPE: DNA
```

<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 332
gtcagtgact ggagagctcc awggaaagtc tctcagtgac ct                          42

<210> SEQ ID NO 333
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 333
tggtctggag tctcggagtc crggcgatgg ccacgatgac ca                          42

<210> SEQ ID NO 334
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 334
aaaaggcctc tggggcaggg argaatgtcc tttaatgggg ac                          42

<210> SEQ ID NO 335
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 335
catgctggag gagacaacag awcccaagtc tggcttccat at                          42

<210> SEQ ID NO 336
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 336
gccaaggatg gctctactgc crtccacttt gagcactctt gg                          42

<210> SEQ ID NO 337
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 337
tgtggtatct ttactggaac crataaatgc acctctggct ct                          42

<210> SEQ ID NO 338
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 338
caaaaattgg aattttgcca grtttaaatt ccagtggcct tc         42

<210> SEQ ID NO 339
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 339
cagtttaaag tccagggtgt trttattacg tgtgcgcaaa ac         42

<210> SEQ ID NO 340
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 340
gtggacgtgc agactgcatc cmtgcttgca ttcccaggga tg         42

<210> SEQ ID NO 341
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 341
ccctttcagc aacaacacca tsggtagaaa tatgatgcag cg         42

<210> SEQ ID NO 342
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 342
cccagcctgc aatcacagct trttactctg ggtgtgggtg gg         42

<210> SEQ ID NO 343
<211> LENGTH: 42
<212> TYPE: DNA
<213> ORGANISM: Homo Sapiens
<220> FEATURE:
<221> NAME/KEY: misc_feature
<222> LOCATION: (22)..(22)

<223> OTHER INFORMATION: m = a or c

<400> SEQUENCE: 343 attttcctttt tttattcttt cmttttccct cctttttctga at                             42

<210> SEQ ID NO 344
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 344
ctggtaggaa attgaactga artcataaac ggaaagcagc ta                               42

<210> SEQ ID NO 345
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 345
ttctaagtcc tctgccatgc crggaaagcc tgggtgcacc ca                               42

<210> SEQ ID NO 346
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 346
ccagggatca gtgaggtctc tragaccctt ggggagcttg cc                               42

<210> SEQ ID NO 347
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 347
acgacgccgt gccgggaata grgaagcagt gtgaggacca ca                               42

<210> SEQ ID NO 348
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 348
actcaagttg agttgatcca trtaattcaa atccctcctc ac                               42

<210> SEQ ID NO 349
<211> LENGTH: 42

<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 349 gaactttat aggttgctgg arggaatgta aattagtgca aa                              42

<210> SEQ ID NO 350
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 350
atcaactgag gaagataata arctataaaa agatgaaaag ga                             42

<210> SEQ ID NO 351
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 351
gccacgggga tttagggaga argcccccg atggttggct cc                              42

<210> SEQ ID NO 352
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 352
ctctatgatt tcacagtgat grgctcaagt atgtgtctgc tt                             42

<210> SEQ ID NO 353
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 353
gctgtgaaca cgcccaccac crtggacagc agcagctggg cc                             42

<210> SEQ ID NO 354
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 354
aggttcatct tgacgcatcc tragctactt aacttcggtt cc    42

<210> SEQ ID NO 355
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 355
aatgtggctg aagccaaaag cmtaatgaat gagggaagc ct    42

<210> SEQ ID NO 356
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 356
tcttccctgg tatgacctga crtccatctg acatggtccc tg    42

<210> SEQ ID NO 357
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 357
aatagatgac tgtgaacagt grtggccagg gaactatctt ca    42

<210> SEQ ID NO 358
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 358
gggcgtcaga gcagactgtc tmcccaaaga atcctccgaa gg    42

<210> SEQ ID NO 359
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 359
gtgcacgagg tccagagata cmttgacctt ctccccacca gc    42

<210> SEQ ID NO 360
<211> LENGTH: 42
<212> TYPE: DNA
<213> ORGANISM: Homo Sapiens
<220> FEATURE:
<221> NAME/KEY: misc_feature -continued
<222> LOCATION: (22)..(22)
<223> OTHER INFORMATION: r = a or g

<400> SEQUENCE: 360
tttcagtagg tttgcaggga arccaactca aagctatatc tg					42

<210> SEQ ID NO 361
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 361
ttcctggcca cactgagaaa cmcctcctttt ccttcgacac at					42

<210> SEQ ID NO 362
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 362
cttggagagg cagataacgc traagcaggc ctctcatgac cc					42

<210> SEQ ID NO 363
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 363
ctgggactgt ggatggatgt artttcgttt tttctagtct gt					42

<210> SEQ ID NO 364
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 364
aagcatggat ctgggaggaa arcagcttgt gtgagttgga ta					42

<210> SEQ ID NO 365
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 365
tcctggcttc cttctggacc crcaaggggc agtctcaaaa ta					42

<210> SEQ ID NO 366

```
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 366
acacacatgt tcagcccaac trgagccttt tgtcagtaag tc                           42

<210> SEQ ID NO 367
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 367
ttatagattg tccagacatg arcagatcta tcacctgacc ac                           42

<210> SEQ ID NO 368
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 368
acaagtctct gaataagaag tsaggctggt gagcattctg gg                           42

<210> SEQ ID NO 369
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 369
cctaatctaa aattttctat trctacatca agggaacaat tt                           42

<210> SEQ ID NO 370
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 370
tcccaaggtg aatgatggtc traggacttc tggtggagag aa                           42

<210> SEQ ID NO 371
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 371
```

```
atgtggggaa gctggaattc trgtatgtga aggtcaggaa ct                    42

<210> SEQ ID NO 372
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 372
cggggaggag gccctaattg tscaatgggg gccgcgtaaa tg                    42

<210> SEQ ID NO 373
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 373
cagaagtttt ttgatatttc crtttgaata ttttggtatc tg                    42

<210> SEQ ID NO 374
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: w = a or t

<400> SEQUENCE: 374
cctcagtgag aacggggagg awgtctagga caggaaagat gc                    42

<210> SEQ ID NO 375
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 375
acctgcctag tcctgggcct grcccttgtc tttggtgaag gg                    42

<210> SEQ ID NO 376
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 376
atacttattg agagaaagaa tsgatccaaa aaatcaaatc tt                    42

<210> SEQ ID NO 377
<211> LENGTH: 42
<212> TYPE: DNA
<213> ORGANISM: Homo Sapiens
<220> FEATURE:
```

```
<221> NAME/KEY: misc_feature
<222> LOCATION: (22)..(22)
<223> OTHER INFORMATION: m = a or c

<400> SEQUENCE: 377
aagaagagat ctcttcaaga tmgataaaac agtgacctct gt                42

<210> SEQ ID NO 378
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 378
aaataaacca gaaattggta artcatcaca tggaaatcaa at                42

<210> SEQ ID NO 379
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: m = a or c

<400> SEQUENCE: 379
gaattggtcc accagcaaaa cmcatttgct tctccgtgga ct                42

<210> SEQ ID NO 380
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: s = c or g

<400> SEQUENCE: 380
ggaaaagaga cggcccggac asgcttcttt ccaaaacgtt ct                42

<210> SEQ ID NO 381
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 381
gcacctacac caacaattca grgtatccca ctgtaagata ta                42

<210> SEQ ID NO 382
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 382
ggcctccttt gctgccctca cratctcttc ctgtgacacc ac                42
```

```
-continued

<210> SEQ ID NO 383
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 383
atgatattga attaaaggaa artgaatggt ctcagtcaga ga                              42

<210> SEQ ID NO 384
<211> LENGTH: 42
<212> TYPE: DNA
<213> ORGANISM: Homo Sapiens
<220> FEATURE:
<221> NAME/KEY: misc_feature
<222> LOCATION: (22)..(22)
<223> OTHER INFORMATION: r = a or g

<400> SEQUENCE: 384
ggcacattca tctttggcac crtcatctgc aaggcggttt cc                              42
```

PHYSIOGENOMIC METHOD FOR PREDICTING CLINICAL OUTCOMES OF TREATMENTS IN PATIENTS

This application is a continuation-in-part application of U.S. patent application Ser. No. 11/010,716, filed on Dec. 14, 2004.

FIELD OF THE INVENTION

In general, the field of the invention is physiogenomics. More specifically, the invention comprises a physiotype method for predicting the results of treatment regimens in a patient.

BACKGROUND

Although clinically highly relevant, physiology has remained a systems and macroscopic embodiment of scientific thought separate from the molecular basis of genetics. The physiogenomics method of the present invention bridges the gap between the systems approach and the genomic approach by using human variability in physiological processes, either in health or disease, to drive their understanding at the genome level. Physiogenomics is particularly relevant to the phenotypes of complex diseases and the clustering of phenotypes into domains according to measurement technique, ranging from functional imaging and clinical scales to protein serology and gene expression.

Physiogenomics integrates genotypes, phenotypes and population analysis of functional variability among individuals. In physiogenomics, allelic genetic markers (single nucleotide polymorphisms or "SNPs", haplotypes, insertion/deletions, tandem repeats) are analyzed to discover statistical associations to physiological characteristics in populations of individuals either at baseline or after they have been similarly exposed or challenged to environmental triggers. These environmental challenges span the gamut from exercise and diet to drugs and toxins, and from extremes of temperature, pressure and altitude to radiation. In the case of complex diseases we are likely to find both baseline characteristics and response phenotypes to as yet undetermined environmental triggers. Variability in a genomic marker among individuals that tracks with the variability in physiological characteristics establishes associations and mechanistic links with specific genes.

Physiogenomics is a medical application of engineering sensitivity analysis [see, e.g., G. Ruano, A. Windemuth, and T. Holford: "Physiogenomics: Integrating systems engineering and nanotechnology for personalized health", The Biomedical Engineering Handbook, 3rd Edition, CRC Press 2006; T. R. Holford, A. Windemuth, and G. Ruano, "Personalizing public health", Personalized Medicine, 2(3), 2005; and A. Saltelli, K. Chan, and E. M. Scott "Sensitivity Analysis", John Wiley and Sons, Chichester, 2000]. Sensitivity analysis is the study about the relations between the input and the output of a model and the analysis utilizing systems theory, of how variation of the input leads to changes in the output quantities. Physiogenomics integrates systems engineering with molecular probes stemming from genomic markers available from industrial technologies. Physiogenomics utilizes as input the variability in genes and relates the genetic variability to variability in the physiological characteristics, which is the output. As a non-limiting example, the genetic variability may be measured by the frequency of single nucleotide polymorphisms (SNPs). With physiogenomics, ensembles of $10^5$ to $10^6$ SNP markers can be integrated with population analysis of functional variability among individuals similarly treated [T. R. Holford, A. Windemuth, and G. Ruano, "Personalizing public health", Personalized Medicine, 2(3), 2005]. Variability in SNP frequency among individuals, which tracks with variability in physiological characteristics, establishes genetic associations and mechanistic links with specific genes.

The physiogenomic method of the invention marks the entry of genomics into systems biology and requires novel analytical platforms to integrate the data and derive the most robust associations. Once physiological systems are under scrutiny, the industrial tools of high-throughput genomics do not suffice, as fundamentals processes such as signal amplification, functional reserve and feedback loops of homeostasis must be incorporated.

The inventive physiogenomics method includes marker discovery and model building. Each of these interrelated components will be described in a generic fashion. Reduction to practice of the generic physiogenomic invention will then be demonstrated by our experimental data in the Examples section.

SUMMARY OF THE INVENTION

One aspect of this invention is to provide a physiogenomics method for predicting whether a particular treatment regimen will produce a beneficial effect on a patient. The method comprises (a) selecting a plurality of genetic markers based on an analysis of the entire human genome or a fraction thereof; (b) identifying significant covariates among demographic data and the other phenotypes using mathematical modeling, preferably by linear regression and $R^2$ analysis or more preferably by principal component analysis; (c) performing for each selected genetic marker an unadjusted association test using genetic data; (d) using permutation testing to obtain a non-parametric and marker complexity probability ("p") value for identifying significant markers, wherein the significance is shown by $p<0.10$, more preferably $p<0.05$, and even more preferably $p<0.01$; (e) constructing a physiogenomic model by linear regression analyses and model parameterization for the dependence of said patient's response to treatment with respect to said markers, wherein said physiogenomic model has $p<0.10$, more preferably $p<0.05$, and even more preferably $p<0.01$; and (f) identifying one or more genes not associated with a particular outcome in said patient to serve as a physiogenomic control.

Another aspect of this invention is to provide a method for treating an individual suffering from a disease or disorder. This method includes the steps of (1) preparing a physiogenomics database that contains a plurality of physiotypes, (2) obtaining genotype and phenotype data of the individual; (3) comparing the genotype data of the individual with said physiotypes in said physiogenomics database; and (4) recommending a treatment regimen based on said comparison.

In an example of the utility of the invention, apolipoprotein E (APOE) haplotypes are used to predict the outcome of exercise training on serum lipid profiles, such as low density lipoprotein cholesterol (LDL-C), high density lipoprotein cholesterol (HDL-C) and lipoprotein particle size distributions.

In another example of the utility of the invention, apolipoprotein A1 (APOA1) genotypes are used to predict the outcome of exercise training on serum lipid profiles, such as LDL-C, HDL-C and lipoprotein particle size distributions.

In still another example of the utility of the invention, genotypes for cholesterol ester transfer protein (CETP), angiotensin converting enzyme (ACE), lipoprotein lipase (LPL), hepatic lipase (LIPC), and peroxisome proliferator-activated receptor-alpha (PPARA) are provided.

In still another embodiment of the invention, cardiovascular inflammatory markers in blood are associated with exercise training, with genetic probes being derived from candidate genes relevant to energy production, inflammation, muscle structure, mitochondrial oxygen consumption, blood pressure, lipid metabolism, and behavior, as well as transcription factors potentially influencing multiple physiological axes.

In yet another embodiment of the invention, phenotypes related to plasma concentrations of interleukins and growth factors and cellular expression of ligand receptors are added to the analysis.

In still another embodiment of the invention, a physiogenomic profile is created for a patient by combining the genomic data for the patient with the patient's clinical and physiological data for each possible treatment modality, said profile serving to provide a logical basis for selecting the most efficacious treatment(s) for the patient.

BRIEF DESCRIPTION OF THE DRAWINGS

FIG. 2: FIG. 2a shows a 40 SNP ensemble (represented as one per row) for 40 individuals (represented as one per column; from left to right, individuals 233, 202, 126, 2, 192, 227, 145, 29, 26, 215, 225, 238, 21, 72, 40, 169, 55, 81, 58, 149, 110, 74, 50, 121, 104, 54, 200, 218, 168, 241, 105, 214, 148, 191, 80, 132, 216, 16, 34 and 70) in a reference population. Each square is a genotype for a person for one of the SNPs in the ensemble. The color coding is as follows: Black-homozygous, Gray-heterozygous genotypes. Individuals 233 through 149 (20 people) are on the left of the figure and are representative of the bottom quartile of response rankings. Individuals 10 through 70 (20 people) are on the right of the figure and are representative of the upper quartile of response rankings.

DETAILED DESCRIPTION OF THE PREFERRED EMBODIMENTS

Figure 1:
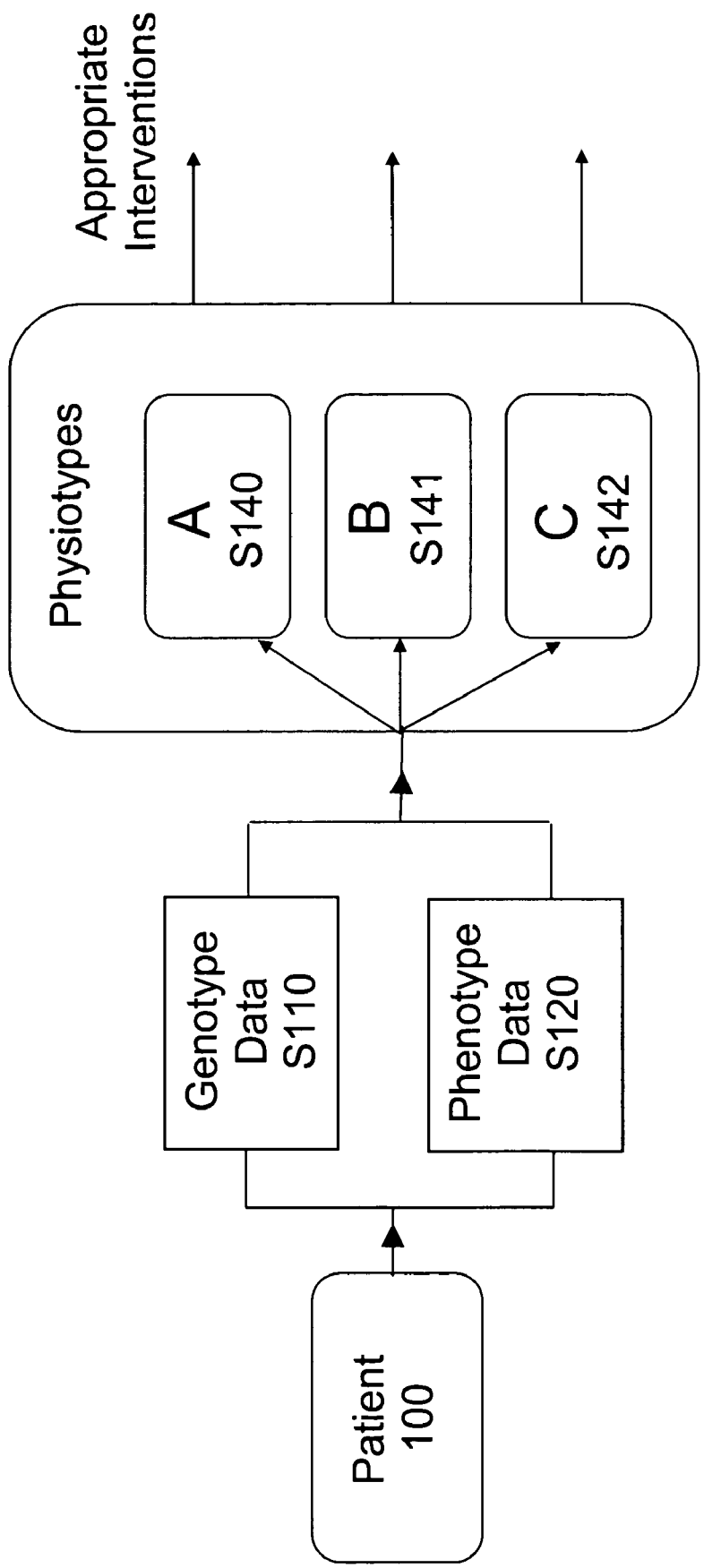
FIG. 1: A schematic diagram of the physiogenomic method according to the invention.

A physiogenomic method for predicting whether or not a particular treatment regimen will have a beneficial outcome in a patient has been invented. The physiogenomic aspect of the method consists of determining genetic markers that are associated with beneficial effects of a particular treatment regimen, and then selecting patients for treatment who present with the beneficial genotype. The physiotype aspect of the method consists of establishing a treatment profile for the patient by combining the aforementioned genomic data with physiological and clinical data for the same patient for each of a set of possible treatments for the patient's medical condition, so as to customize interventions for the patient.

The following definitions will be used in the specification and claims:

1. Correlations or other statistical measures of relatedness between genotypes and physiologic parameters are as used by one of ordinary skill in this art.
2. As use herein, "polymorphism" refers to DNA sequence variations in the cellular genomes of animals, preferably mammals. Such variations include mutations, single nucleotide changes, insertions and deletions. Single nucleotide polymorphism ("SNP") refers to those differences among samples of DNA in which a single nucleotide pair has been substituted by another.
3. As used herein, "variants" is synonymous with polymorphism.
4. As used herein, "phenotype" refers to any observable or otherwise measurable physiological, morphological, biological, biochemical or clinical characteristic of an organism. The point of genetic studies is to detect consistent relationships between phenotypes and DNA sequence variation (genotypes).
5. As used herein, "genotype" refers to the genetic composition of an organism. More specifically, "genotyping" as used herein refers to the analysis of DNA in a sample obtained from a subject to determine the DNA sequence in one or more specific regions of the genome, for example, at a gene that influences a disease or drug response.
6. As used herein, "genetic marker" refers to the partial or complete sequence of an inherited segment of DNA constitutional to an individual. The DNA segment may include a SNP, a part of a gene, an entire gene, several genes or a region devoid of genes
7. As used herein, the term "associated with" in connection with a relationship between a genetic marker (SNP, haplotype, insertion/deletion, tandem repeat) and a phenotype refers to a statistically significant dependence of marker frequency with respect to a quantitative scale or qualitative gradation of the phenotype.
8. As used herein, a "gene" is a sequence of DNA present in a cell that directs the expression of biochemicals, i.e., proteins, through, most commonly, a complementary RNA.
9. "BMI" refers to body mass index.

This invention provides methods for determining physiotypes acquired from physiogenomic data and using the physiotypes to select which treatment or treatments would be most efficacious for a patient suffering from a disease or a disorder. Physiotypes are useful for describing an ensemble of genetic markers and an interpretative algorithm used as a medical device or platform to predict an individual's physiological response to a treatment. The use of physiotypes for studying environmental interactions for the prevention and treatment of disease is attractive, for several reasons. For example, because the determination of a physiotype involves, in part, a determination of a genotype component that does not change as a result of environmental stimuli, the contribution of the genotype component is not confounded with environmental stimuli. Furthermore, some genotypes associated with a phenotype can act as a surrogate marker for the phenotype, which can be useful when measurement of the phenotype is difficult, expensive, or confounded by environmental conditions. Additionally, the cost of developing robust, reliable physiotypes has decreased with the decreasing cost associated with new automated genotyping technologies, which have allowed for economic determination of multiple genotypes from different genes coding for proteins in interacting pathways.

Figure 2A:
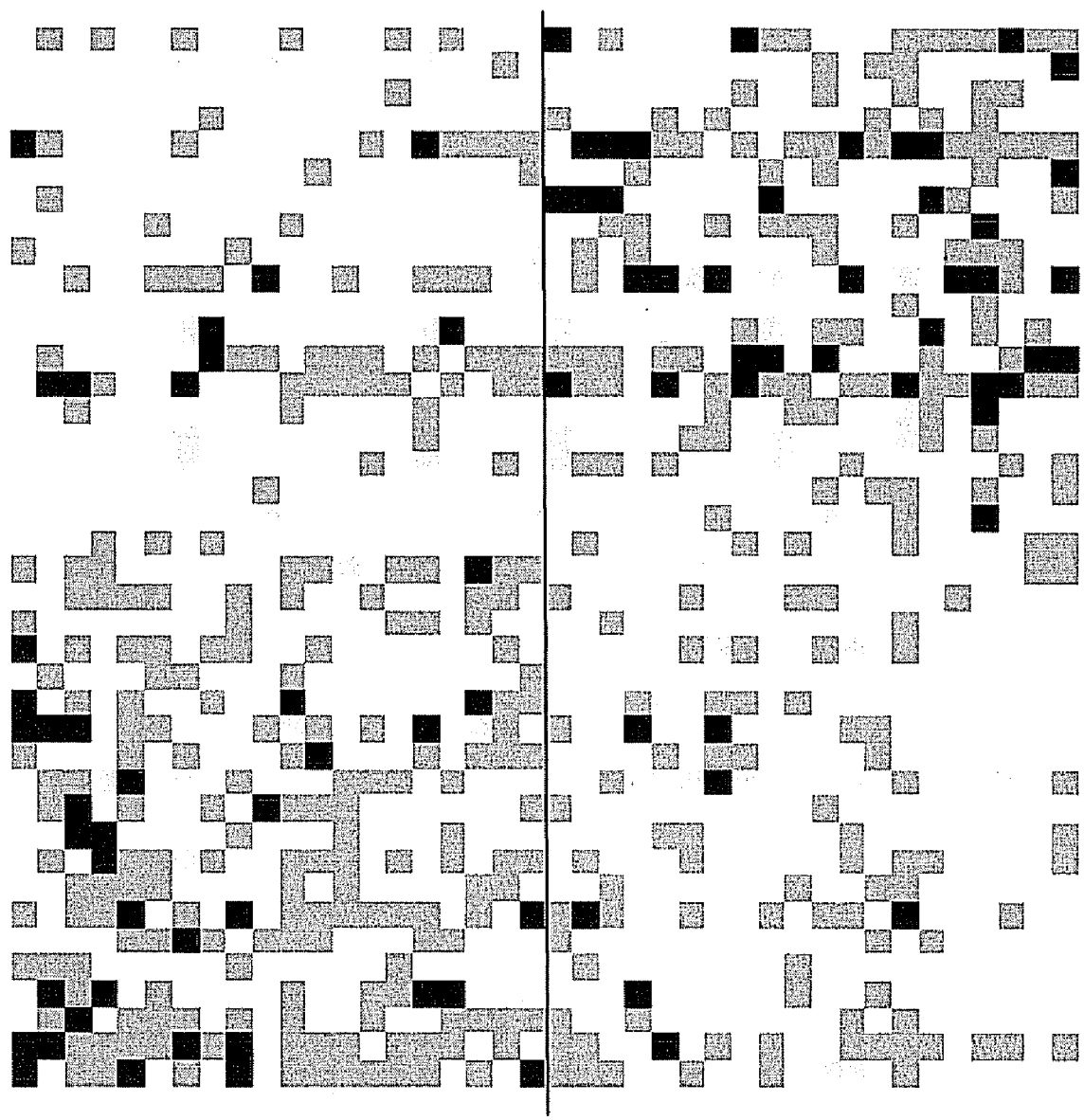
FIG. 2a shows the response distribution corresponding to serum creatine kinase (CK) activity as the result of statin treatment for the individuals in a reference population whose genetic data was used to form a physiogenomic database. More specifically.
Figure 2B:
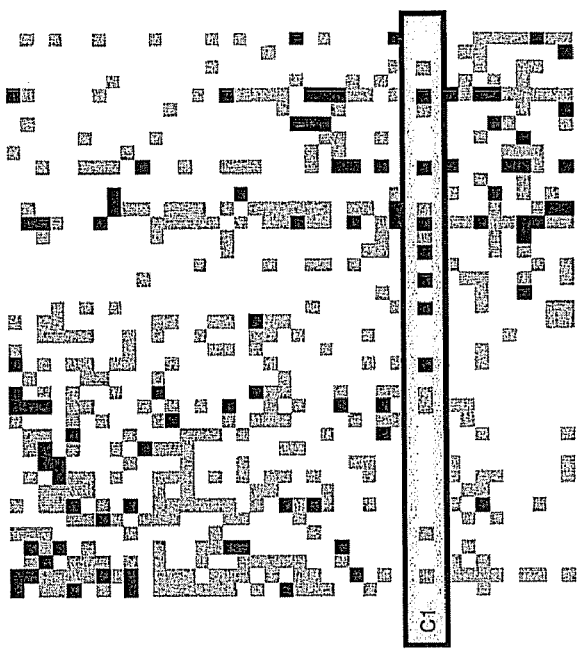
FIG. 2b shows a percentile ranking of a test individual Cl's predicted physical response against the distribution of SNP marker ensembles of the reference population (from left to right, individuals 233, 202, 126, 2, 192, 227, 145, 29, 26, 215, 225, 238, 21, 72, 40, 169, 55, 81, 58, 149, 110, 74, 50, 121, 104, 54, 200, 218, 168, 241, 105, 214, 148, 191, 80, 132, 216, 16, 34 and 70) which constitute the distribution curve.
Figure 2B:
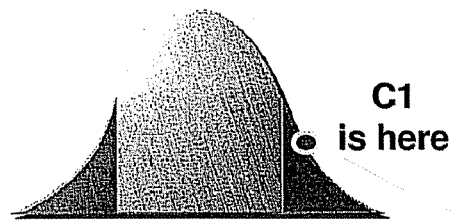

FIG. 1 shows a schematic diagram of the method according to the invention. The inventive method uses genotype data S110 and phenotype data S120 of patient 100 as inputs for physiogenomic analysis S130, which establishes physiotypes A, B, and C (corresponding to reference numerals S140, S141, and S142 in FIG. 1, respectively). In determining which interventions would be appropriate, it is often useful to calculate a patient's predicted physiological response using the physiological responses of the reference population whose genetic data forms the physiogenomic database. By way of example, FIG. 2a shows genetic data of a reference population consisting of 40 individuals. As shown in FIG. 2b, the predicted physiological response of a test individual C1 can be graphically displayed, on a percentile basis, by comparing the genetic data of C1 against the genetic marker ensembles of the reference population, illustrated as a distribution curve.

These physiotypes taken together constitute a physiogenomics database to which a physician could refer in order to determine an efficacious, personalized treatment protocol for a patient. A physician with genetic and clinical information about a particular patient could determine which interventions would be appropriate, by comparing the patient data with the physiotypes in the physiogenomic database.

As used herein, the term "interventions" refers to any type of treatment, non-limiting examples of which include dietary changes or restrictions, drug therapy, exercise, or even specific combinations of such treatments. Generally, the number of interventions will be sufficient such that the probability that the patient will respond poorly to all of the interventions will be quite small. For example, in a scenario where there are three possible interventions, the probability that the patient's response will be in the bottom 25% for all three treatments is $(1/4)^3 = 1/64$ or about 1.5%.

Development of Physiotypes

Physiotypes may be developed from genotypes from various genes and genomic regions. As set forth below, in preferred embodiments, the physiotypes are developed using either (1) hypothesis free association screening, or (2) hypothesis-led association screening. In either method of screening, genetic markers are correlated with phenotypes that may be determined from clinical studies. However, this invention also recognizes that sometimes genetic effects are not direct, and that it is advantageous to use endophenotypes in the development of physiotypes. As used herein, "endophenotypes" are observable intermediate phenotypes that can be measured to provide additional information about the association between an individual's genes and his response. Non-limiting examples of endophenotypes contemplated by the invention include mRNA expression levels, functional brain imaging data, and blood levels of cells, proteins, lipids, and metabolites. The use of endophenotypes to break down genetic/physiological associations into intermediate levels is advantageous for several reasons. First, each individual interaction is more direct, and therefore stronger (i.e., less diluted by confounding variables) and easier to detect. Second, there may be multiple associations on each level contributing to the overall association, providing a degree of redundancy such that the overall association can still be found, even if some of the components are missed. Third, the structure of the intermediate associations provides a significant amount of information about the underlying mechanism that gives rise to the association.

A. Determination of Markers by Hypothesis Free Association Screening Array Design and Fabrication With the rapid development array technology for SNP analysis, it has now become possible to use a "hypothesis free association screening" approach to determine the genotype component of a physiotype. In this context, the term "hypothesis free association screening" refers to a method of genetic screening that involves screening the entire human genome, rather than a subset of the genome based on a pre-conceived "hypothesis" of which genes would be relevant. This method offers the possibility of discovering new, previously unknown correlations between genotypes and phenotypes.

The genetic screening contemplated by the invention for hypothesis testing is not particularly limited, and may involve any DNA screening platform that has sufficiently high throughput density and is sensitive to one or more genetic markers, non-limiting examples of which include SNPs, haplotypes, insertions/deletions, and tandem repeats. By way of example, the array may be a fixed array, wherein SNP specific reagents are deposited on a substrate using photolithographic techniques similar to that commonly used in the semiconductor industry. Alternatively, the exemplary array may be a random array, wherein the location of the SNP specific reagents is not predetermined but random, and the identity of reagents is identified by use of various markers. For example, a SNP specific random array may be a microbead array, wherein various SNP specific reagents are chemically linked to microscopic beads (e.g., 2 microns or less) that also have covalently attached fluorescent identifier molecules. Typically, in such bead-based arrays, the beads are immobilized to a surface prior to detection. (See, e.g., U.S. Pat. Nos. 6,327,410; 6,429,027; and 6,797,524, all of which are hereby incorporated by reference in their entirety.)

In a particularly preferred embodiment of the invention, the DNA array platform involves attaching oligonucleotide probes 10-20 nm long onto the surface of microbeads with an average diameter of about 2 microns. The beads are divided into different subpopulations, wherein each bead in a given subpopulation has a different SNP specific oligonucleotided (typically about 50 bases in length) which is designed to hybridize specifically to a specific spot on the genome adjacent to the SNP. Allele specific extension with labeled oligonucleotides is used to confer a fluorescent signal to only those beads that carry a matching probe for a given allele. Furthermore, the individual subpopulations are marked by subpopulation-specific markers.

In addition to the fixed and random arrays described above, this invention also contemplates the use of a "liquid arrays", which do not require the immobilization of beads, but instead use a microfluidic device similar to a flow cytometer to identify and to read the signal from the microscopic beads while they are suspended in liquid. While current liquid arrays are suitable for small arrays only (e.g., analyzing 100 SNPs in parallel), the rapid advances in liquid array technology suggest that liquid array technology holds promise for large scale genetic analysis.

Determination of Array Size

Figure 3:
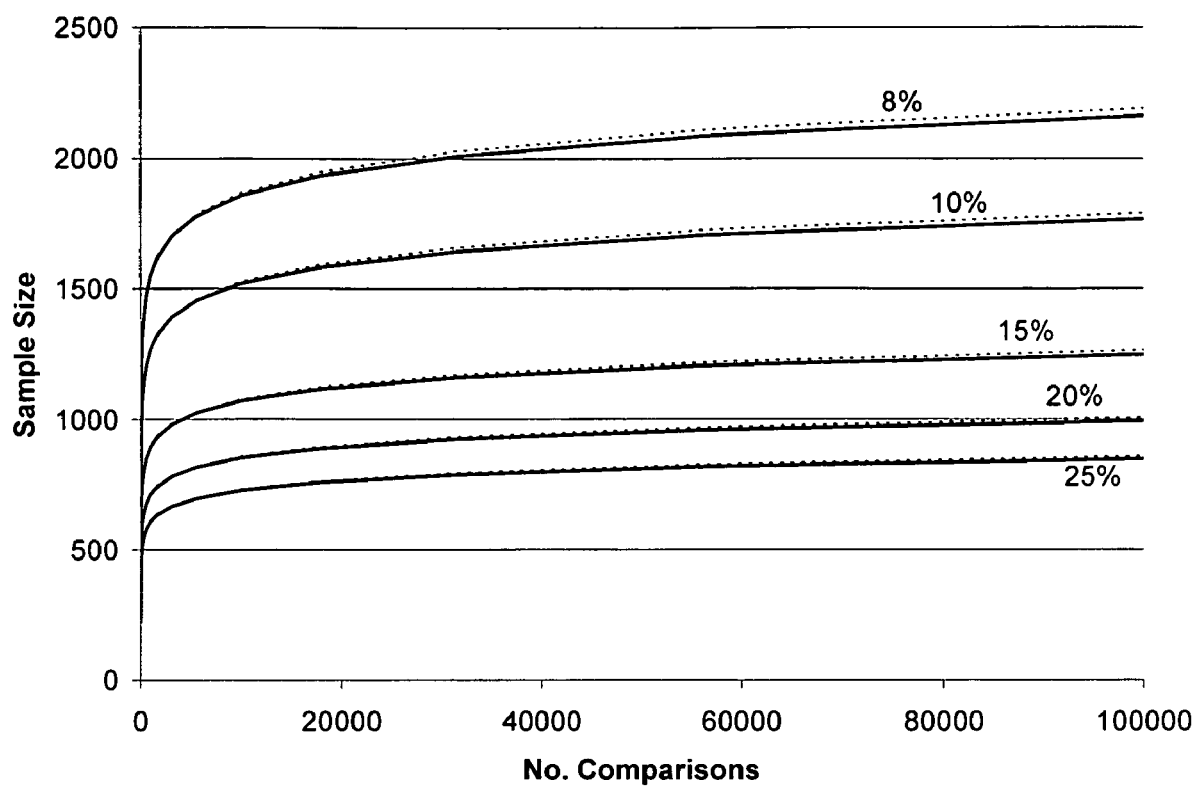
FIG. 3: The trend in required sample size to detect a 0.5 standard deviation effect by number of comparisons and carrier prevalence along with the estimate using this approximation.

While microarray technology, such as the bead-based microarray technology described above, can be used to produce thousands of biomarkers for subject, it is widely recognized that Type I error rates (i.e., the error rate resulting from false positives that exist when a test incorrectly reports that it has found a result when none really exists) from studies of numerous markers can become unacceptably high, producing false discoveries that arise from multiple comparisons. Accordingly, sample size must be increased to take into account these multiple comparisons. One aspect of this invention is the recognition that the logarithmic dependence of sample size on marker number makes it possible to analyze a large number of markers with only a modest increase in the number of people in the test population. For example, using a typical expression for calculating sample size, n, as well as an approximation to the error function yields a good approximation to sample size calculation with a Bonferroni adjustment, where the significance level is α/c (α=significance level, and c=number of SNPs $$n = \frac{(z_\alpha \sigma_0 + z_\beta \sigma_1)^2}{p(1-p)\Delta^2} + \frac{2(1 + (z_\beta / \sqrt{0.5 \ln c_{max} - 2\ln \alpha}))\sigma_0^2}{p(1-p)\Delta^2} \cdot \ln c$$

where $\sigma_0^2$ and $\sigma_1^2$ are variances of response under null and alternative hypotheses, β=Type II error (a Type II error, also called a false negative, exists when a test incorrectly reports that a result was not detected, when it was really present), z=standard normal deviate, p=carrier proportion (under Hardy-Weinberg equilibrium, p=1−(1−φ)² where φ=allele frequency), and Δ=effect size. Thus, the increased sample size required to study 10 genes (using the Bonferroni adjustment) instead of one is the same as that required to study 100 genes instead of 10. Thus, huge gains in efficiency may be realized with a modest increase in sample size. FIG. 3 shows the trend in required sample size to detect 0.5 standard deviation effect by number of comparisons and carrier prevalence along with the estimate using this approximation. For example, when the carrier prevalence is 20%, the total sample size required for a single gene is 263, which increases to 412 for 10 genes and 561 for 100 genes. Thus, if one were to consider the entire human genome (about 100,000 genes), the required sample size is only 1009, about four times as large for a single gene study.

By way of example, Table 1 lists a few strong associations reported in the literature, along with the sample sizes needed to detect each of them as significant (alpha=0.05, power=80%), while correcting for 100,000 markers testing using the Bonferroni correction. All of the markers listed would be detected as significant in a genome wide study of 400 subjects, In particular, the angiotensin converting enzyme would be significant at N=100.

While the Bonferroni method provides a conservative estimate of the required sample size, this invention also contemplates other methods of determining sample size, such as the false discovery rate (see. e.g., A Reinere, et al. "Identifying differentially expressed genes using false discovery rate controlling procedures", Bioinformatics 2003, 19:368-375; Y. Benjamin et al, "Controlling the false discovery rate: a practical and powerful approach to multiple testing"; Journal of the Royal Statistical Society, Series B 1995; 57:289-300; Y. Benjamin et al., "On adaptive control of the false discovery rate in multiple testing with independent statistics"; Journal of Educational and Behavior Statistics 2000; 25:60-83.)

B. Determining Physiogenomic Markers by Hypothesis-led Association Screening Association Screening In addition to hypothesis free testing, this invention also contemplates identifying physiogenomic markers by association screening. The purpose of association screening is to identify any of a large set of genetic markers (SNPs, haplotypes, insertion/deletions, tandem repeats) associated with physiological characteristics, i.e., factors that have an influence on the disease status of the patient, the progression to disease or the response to treatment. In certain preferred embodiments of the invention, association screening uses DNA screening technology (such as the fixed or random array technology described above) in order to determine the relevant genetic markers. However, unlike the hypothesis free association screening approach, the hypothesis-led association screening approach does not examine the entire human genome, but instead uses only a subset of genome as candidate genes. Typically, candidate genes have been already reported in the literature. For example, in certain preferred embodiments, the genetic markers of interest are SNPs, and the array is constructed using SNPs that are reported in the SNP Knowledge resource database, a user-friendly source for SNP annotation that represents a compendium of information derived from dbSNP, ENSEMBL, HapMap.Org, and Illumina's database. Useful factors to consider in the designing an array include Minor Allele Frequencies (MAF) information, validation status, genome coordinates, and locations within genes (intron, exon, splice site, promoter)

Association Testing

One of the challenges in data analysis is spotting the trends in the data when the amount of data is extremely large. This is particularly true in physiogenomic studies, where the entire genome may be investigated (e.g., by hypothesis free discovery) or a large set of genetic markers has been pre-selected (e.g., by hypothesis-led association screening) One aspect of this invention is the recognition that (1) it is advantageous to log transform clinically derived data (such as the serum concentration of a particular substance) in order to derive an approximately normally distributed variable, and (2) that an association can be visualized by plotting a locally smoothed

TABLE 1

Selection of strong associations reported in the literature. The minimum sample size (Nwg) required to detect the association in a whole genome association study of 100,000 markers is given for each.

| Gene | Marker | | N | | Effect | | |
| | Allele | Freq | tot | carr | Absolute | SD | Nwg |
| --- | --- | --- | --- | --- | --- | --- | --- |
| Apolioprotein E | *2 hom | 0.0081 | 14 | 4 | −53 mg/dl apo B in VLDL | 3.15 | 412 |
| Apolioprotein A1 | −75 G/A | 0.3 | 75 | 22 | 7.9 mg/dl HDL | 0.7 | 324 |
| Hepatic Lipase | 514 C/T | 0.015 | 133 | 2 | 28 mg/dl HDL-C | 2.8 | 283 |
| Apolioprotein E | *4 | 0.31 | 260 | 81 | 0.93 mg/L CRP | 0.86 | 207 |
| Adipocyte-derived leucine aminopeptidase | Arg527 | 0.4 | 40 | 16 | 13.4 g/m² dL VMI | 0.85 | 190 |
| Angiotensin converting enzyme | 250 bp Ins/del | 0.17 | 80 | 14 | 100 μg/l ACEser | 1.5 | 101 | function of the genetic marker data (e.g., the SNP frequency) against such log transformed data. In one particularly preferred embodiment, the locally smoothed function of the genetic data is obtained by using LOESS (Locally-weighted Scatter plot Smooth) smoothing. LOESS is a method to smooth data using a locally weighted linear regression [e.g., see W. S. Cleveland, "Robust locally weighted regression and smoothing scatterplots", J. Am. Stat. Assoc. 74, 829-836 (1979); W. S. Cleveland et al, "Locally weighted regression: an approach to regression analysis by local fitting, J. Am.Stat. Assoc. 83, 596-610 (1988)]. At each point on the LOESS curve, a quadratic polynomial is fitted to the data in the vicinity of that point. The data are weighted such that they contribute less if they are further away, according to the tricubic function $$w_i = \left(1 - \left|\frac{x - x_i}{d(x)}\right|^3\right)^3$$

where x is the abscissa of the point to be estimated, the $x_i$ are data points in the vicinity, and $d(x)$ is the maximum distance of x to the $x_i$.

Figure 4:
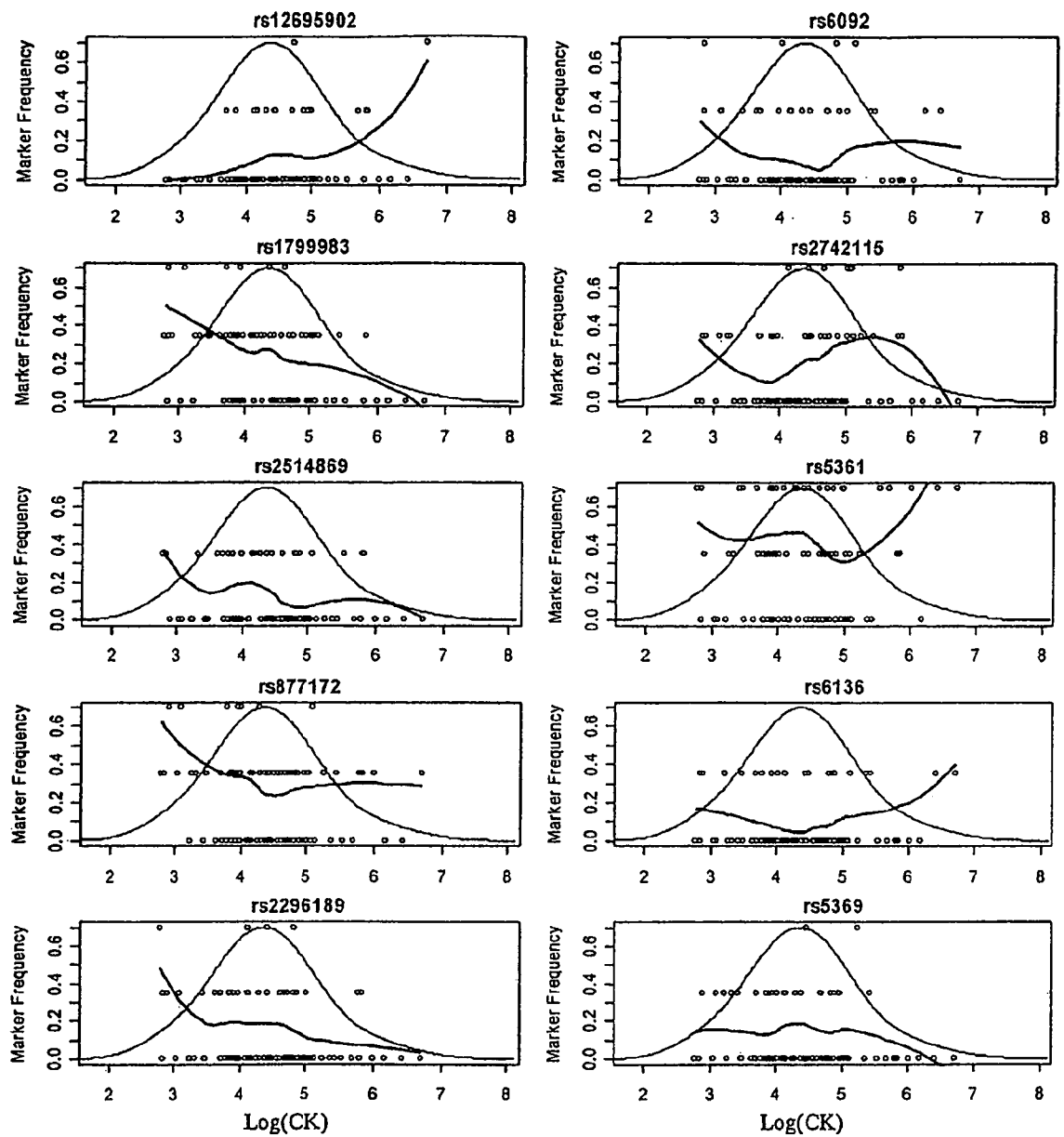
FIG. 4: A detailed representation of the genetic association tests for 10 SNPs. The overall distribution of log(CK) is shown along with the individual genotypes and a LOESS fit of the allele frequency as a function of log(CK).

The LOESS curve generated for a particular set of data that has been plotted as the genetic marker frequency versus the log transformed clinical data is useful because it shows the localized frequency of the least common allele for sectors of the distribution. For genetic markers with strong association, the marker frequency is significantly different between the high end and the low end of the distribution. Conversely, if a marker is neutral, the LOESS curve is essentially flat, because the marker frequency will be independent of the log transformed clinical data. By way of example, FIG. 4 shows a detailed representation of the genetic association tests for 10 different SNPs, and their relationship to creatine kinase (CK) levels. The overall distribution of log(CK) is shown along with the individual genotypes and a LOESS fit of the allele frequency as a function of log(CK). The bell curve shows the actual distribution of CK activity phenotype in a clinical database. The LOESS curve shows the localized frequency of the least common allele for sectors of the distribution. For SNPs with a strong association, the marker frequency is significantly different between the high end and the low end of the distribution. Conversely, if a marker is neutral, the frequency is independent on the CK activity and the LOESS curve is essentially flat such as for marker rs6092. For example, the first figure of the panel shows the LOESS curve for SNP rs12695902, which is located in the gene for angiotensin II receptor, type 1 (AGTR1). The frequency of the minor allele is almost zero in subjects with low CK activity, whereas it approaches 50% at the high end of CK activity. This is indicative of a strong association between the marker and CK activity. Thus, the model contains both neutral markers and strongly associated markers. Further, among the strongly associated markers the model also includes oppositely associated markers. For example, rs12695902, rs5361 and rs6136 are positively associated markers, that is, they have a higher frequency at high CK activity. In contrast, rs1799983, rs2514869, rs877172 and rs2296189 are negatively associated markers, that is, they have a higher frequency at low CK activity.

In certain embodiments, the association between each genetic marker and the outcome, whether derived from hypothesis-free discovery or by hypothesis-led association screening, is tested using logistic regression models, controlling for the other genetic markers that have been found to be relevant. The magnitude of these associations is measured with the odds ratio, and the statistical significance of these associations is determined by constructing 95% confidence intervals. Multivariate analyses are used which include all genetic markers that have been found to be important based on univariate analyses. Because the number of possible comparisons can become very large in analyses that evaluate the combined effects of two or more genes, the results include a random permutation test for the null hypothesis of no effect for two through five combinations of genes. This test is performed by randomly assigning phenotypes to each individual in the study. Random associations of phenotypes and genotypes of the invididuals are implied by the null distribution of no genetic effect. A test statistic can be calculated that corresponds to the null hypothesis of the random combination effects of genotypes and phenotypes. Repeating this process 1000 times provides an empirical estimate of the distribution for the test statistic, and hence a p-value that takes into account the process that gave rise to the multiple comparisons.

A single association test will proceed in 3 steps:

(Step 1) Covariates

The purpose of this step is to identify significant covariates among demographic data and the other phenotypes and delineate correlated phenotypes by principal component analysis. Covariates are determined by generating a covariance matrix for all markers and selecting each significantly correlated markers for use as a covariate in the association test of each marker. Serological markers and baseline outcomes are tested using linear regression.

(Step 2) Associations

The purpose of this step is to perform an unadjusted association test, linear regression for serum levels and baselines). Tests should be performed on each marker, and markers that clear a significance threshold of p<0.05 are selected for permutation testing.

(Step 3) Multiple Comparison Corrections

In this step, a non-parametric and marker complexity adjusted p-value are generated by permutation testing. This procedure is important because the p-value is used for identifying a few significant markers out of the large number of candidates. Model-based p-values are unsuitable for such selection, because the multiple testing of every potential serological marker and every polymorphic marker will be likely to yield some results that appear to be statistically significant even though they occurred by chance alone. If not corrected, such differences will lead to spurious markers being picked as the most significant. A correction will be made by permutation testing, i.e., the same tests will be performed on a large number of data sets that differ from the original by having the response variable permuted at random with respect to the marker, thereby providing a non parametric estimate of the null distribution of the test statistics. The ranking of the non-permuted test result in the distribution of permuted test results will provide a non-parametric and statistically rigorous estimate of the false positive rate for this marker. For permutation testing, a large number (e.g., 1000) of permutated data sets are generated, and each candidate marker is retested on each of those sets. A p-value is assigned according to the ranking of the original test result within the control results. A marker is selected for model building when the original test ranks, for example, within the top 50 of the 1000 (p<0.05).

(Step 4) Genomic Controls and Negative Results

Each gene not associated with a particular outcome effectively serves as a negative control, and demonstrates neutral segregation of non-related markers. The negative controls altogether constitute a "genomic control" for the positive associations where segregation of alleles tracks segregation of outcomes. By requiring the representation of the least common allele for each gene to be at least 10% of the population, one can rule out associations clearly driven by statistical outliers. Negative results are thus particularly useful in physiogenomics. To the extent that specific candidate genes are not linked to phenotypes, one can still gain mechanistic understanding of complex systems, especially for segregating the influences of the various candidate genes among the various phenotypes.

B. Construction of Physiogenomic Models (Step 1) Model Building

The next stage in the inventive method is physiogenomic modeling. Once the associated markers have been determined, a model is built for the dependence of response on the genetic markers. In the first phase, linear regression models of the following form are preferably used:

$$R = R_o + \sum_i \alpha_i M_i + \sum_i \beta_i D_i + \varepsilon$$

where R is the respective phenotype variable (e.g., BMI), $M_i$ represents the marker variables, $D_i$ are demographic covariates, and $\varepsilon$ is the residual unexplained variation. The model parameters that are to be estimated from the data are $R_o$, $\alpha_i$ and $\beta_i$.

(Step 2) Model Parameters

The models built in the previous step will include parameters based on the data. The maximum likelihood method is preferably used, as this is a well-established method for obtaining optimal estimates of parameters.

In addition to optimizing the parameters, model refinement may be performed. In the first phase linear regression model, this consists of considering a set of simplified models by eliminating each variable in turn and re-optimizing the likelihood function. The ratio between the two maximum likelihoods of the original compared to the simplified model then provides a significance measure for the contribution of each variable to the model.

(Step 3) Model Validation

A cross-validation approach is used to evaluate the performance of models by separating the data used for parameterization (training set) from the data used for testing (test set). A model to be evaluated is readjusted with parameters derived using all data except for one patient. The likelihood of the outcome for this patient is calculated using the outcome distribution from the model. The procedure is repeated for each patient, and the product of all likelihoods is computed. The resulting likelihood is compared with the likelihood of the data under the null model (no markers, predicted distribution equal to general distribution). If the likelihood ratio is p<0.05, the model should be evaluated as providing a significant improvement of the null model. If this threshold is not reached, the model is not sufficiently supported by the data, which could mean either that there is not enough data, or that the model does not reflect actual dependencies between the variables.

Physiotypes for various treatments are used for decision support in a menu driven format (see Example 6, below). For achieving a desired therapeutic outcome for a given patient, physiotypes for each of the various treatment alternatives (exercise, drugs, and diet) are applied to predict quantitatively the patient's response for each. To derive the physiotypes, physiological and clinical data gathered by the physician and genomic data from several genetic markers, are combined to produce an intervention profile menu. Predictions made by the physiotype will rank the best alternatives among the menu options to achieve a desired goal. As more options are built into the menu, the greater the chance that all patients will be served with increased precision of intervention and with optimal outcome.

As long as the appropriate physiogenomics research has been performed for each intervention in the menu, an individual's physiotypes would evaluate all possibilities for optimized healthcare. The clinician can query for simple indexes such as raising HDL, or lowering triglycerides or compounded indexes such as LDL/HDL ratios or simultaneous elevation of HDL and reduction of TG. Physiotypes are derived for each intervention to predict a single effect or combined outcomes, and the same decision-making process can proceed seamlessly.

Models can be created by the method of the invention that predict various lipid, inflammatory and anthropometric responses to diet, exercise and drugs.

The baseline physiological and clinical level is measured for several phenotypes ranging from serology, physical exam, imaging, endocrinology for genomic/proteomics markers. The response of each individual for the phenotypes is then acquired after the exposure. Physiogenomics utilizes variability in response in the cohort to derive the predictors of response. After the physiotypes have been established for each given intervention, they can be applied to predict the response of a new individual to the intervention.

The medical utility of the invention will depend on the range of options it can customize. Within each of the major treatment modes (exercise, drug and diet), alternatives should be available to achieve specified goals. For example, consider dietary intervention to raise HDL in a patient with metabolic syndrome, and a decision on whether to proceed with a low fat or low carbohydrate diet. With physiotypes discovered each for low fat and low carbohydrate diets, predictions can be drawn for an individual's response to either. The person's genetic markers would be entered into the physiotypes, and the best diet based on the physiotype's prediction can be identified for the individual. Physiotypes can be generated, not only for various kinds of diet, but also for various kinds of exercise and drug treatments. The menu of possible interventions is thus broadened. The physiotype yielding the best outcome for a given desired effect guides the mode of intervention from an increasingly diversified menu, thus allowing enhanced personalization and customization of treatment.

It is within the scope of the present invention to produce for a given patient in permanent printed form a record of the prognostic results of his/her physiogenomic analyses disclosed above. This profile will become part of the patient's records. The printed form may be produced by any means, including a computer-generated printout.

We have applied the physiogenomic prognostic method described above to several treatment regimens, including those described below in the Examples section. Examples are designed to illustrate the inventive method, and should not be interpreted as limiting the scope of the invention.

EXAMPLES

Example 1

Determination of Sample Size

In order to determine the sample size requirements for a study, preliminary data is obtained and the percent change in BMI with treatment is assessed. For example, the standard deviation for percent change in BMI among the subjects was 5%. Table 2 shows the total sample size required, compared against the physiogenomic prevalence to detect a given percent change in BMI using a 5% two-tailed test with 80% power. This demonstrates that a study with 150 subjects should have sufficient power to detect a mean difference of 2.5% BMI if the genetic prevalence is between 25% and 75% of the population and 3.0% if between 10% and 90%.

TABLE 2

Sample size required by percent change in BMI for 5% significance level and 80% power at genetic marker frequencies between 25% and 75% in the sample population

| Percent BMI Change | Sample Size |
|---|---|
| 2.5 | 150 |
| 3.0 | 100 |
| 4.0 | 60 |
| 5.0 | 40 |

Example 2

Physiogenomics of Exercise

The inventive method was tested by examining the effects of exercise on lipid profiles, as a function of the genotypes of seven marker biochemicals that are known to be involved in lipid metabolism and serum lipid levels. We correlated the exercise responses as measured by various outcomes with the variability of the selected candidate genes. The candidate genes were selected according to known mechanisms of cholesterol homeostasis and the exercise response. The candidate genes and the candidate genotypes are shown in Table 3. The genes and their abbreviations are: apolipoprotein E (APOE), apolipoprotein A1 (APOA1), cholesterol ester transfer protein (CETP), angiotensin converting enzyme (ACE), lipoprotein lipase (LPL), hepatic lipase (LIPC), and peroxisome proliferator-activated receptor-alpha (PPARA). Other genes analyzed were ATP-binding cassette, sub-family G (WHITE), member 5 (sterolin 1) (ABCG5) and cholesterol 7-alpha hydroxylase gene (CYP7).

TABLE 3

| Genes | Candidate Genetic Markers | References |
|---|---|---|
| APOE | Haplotype E2, E3, E4 | Thompson PD, et al., Metabolism 53: 193-202 (2004) |
| APOA1 | SNP −75 G/A | Marin, C et al., Am. J. Clin. Nutr. 76: 319 (2002) |
| CETP | SNP −629 C/A | Tai, ES et al., Clin. Genet. 63: 19 (2003) |
| LPL | SNP −93 T/G S447X (CtoG) | Corella et al., J. Lipid Res. 43: 416-427 (2002) |
| LIPC | SNP −514 C/T | Ordovas, JM et al., Circulation 106: 2315 (2002) |
| ACE | Insertion/Deletion I/D 287 | Rankinen T, et al., J. Appl. Physiol. 88: 1029-1035 (2000) |
| PPARA | SNP Leu162Val | Tai, ES et al. Clin. Genet. 63: 19 (2003) |

A preferred method for obtaining additional genotypes is the BeadStation 500GX system (Illumina®, Inc., 9885 Towne Creek Center Drive, San Diego, Calif. 02121). This is an integrated system that supports highly parallel SNP genotyping and RNA profiling applications on a single, high-performance platform that delivers a scalable range of sample throughput.

Example 3

Exercise Physiogenomics Incorporating APOE Genetic markers

The following experiments explored the inventive concept that APOE variability is related to lipid changes with exercise training. To this end, three equal cohorts with subjects having the most common APOE haplotype pairs in the general population, APOE 2/3, 3/3, and 3/4, were recruited. To control for this design characteristic, APOE haplotype was utilized as covariate for the analysis of the other genetic markers, and was found not to be associated, thus demonstrating that none of the other gentic markers were in physical linkage with APOE and assorted randomly in the three cohorts. Variability in each gene was measured by a genetic polymorphism with a frequency of at least 10%. Such sampling establishes three groups of individuals for each gene: homozygous for either allele or heterozygous.

TABLE 4

Physiogenomics data analysis and screening for associations of gene marker and phenotypes

| Lipids | | | | | | Physiological | | | | |
|---|---|---|---|---|---|---|---|---|---|---|
| A | B | C | D | E | F | G | H | I | J | Phenotype |
| 4 | 0 | 3 | 23 | 2 | 5 | 1 | 27 | 30 | 0 | APOE |
| 4 | 3 | 1 | 5 | 3 | 16 | 17 | 25 | 23 | 3 | PPARA |
| 0 | 3 | 4 | 6 | 0 | 27 | 0 | 7 | 3 | 11 | LIPC |
| 0 | 0 | 3 | 0 | 3 | 2 | 4 | 1 | 5 | 16 | LPL |
| 21 | 32 | 21 | 0 | 1 | 2 | 11 | 2 | 3 | 6 | APOA1 |
| 9 | 5 | 0 | 0 | 23 | 5 | 3 | 9 | 12 | 11 | CETP |
| 4 | 6 | 5 | 2 | 1 | 1 | 0 | 3 | 1 | 2 | ACE |
| 1 | 2 | 0 | 1 | 5 | 8 | 9 | 1 | 0 | 0 | ABCG5 |
| 2 | 2 | 3 | 4 | 6 | 0 | 4 | 0 | 2 | 2 | CYP7 |

TABLE 5

Summary of highest ranked association results from Table 4

| Column | Gene | Phenotype | Adj P | In Count | Out Count |
|---|---|---|---|---|---|
| B | APOA1 | CHGSMHDL | 32 | 22 | 53 |
| I | APOE | VMAXLCHG | 30 | 42 | 77 |
| H | APOE | VMXMLCHG | 27 | 42 | 77 |
| F | LIPC | CHGAPOB | 27 | 6 | 83 |
| H | PPARA | VMXMLCHG | 25 | 11 | 89 |
| D | APOE | CHGL2M | 23 | 40 | 66 |
| I | PPARA | VMAXLCHG | 23 | 11 | 89 |
| E | CETP | CHGLDLSZ | 23 | 44 | 25 |
| C | APOA1 | CHGH345 | 21 | 22 | 53 |
| A | APOA1 | CHGV56 | 21 | 22 | 53 |
| G | PPARA | CHGHLA | 17 | 11 | 86 |
| F | PPARA | CHGAPOB | 16 | 11 | 90 |
| J | LPL | CHGBMI | 16 | 18 | 64 |

The code letters and names for the phenotypes in Tables 4 and 5 are defined as:
A  CHGV56 = change in VLDL subpopulations V5 and V6 (i.e., largest VLDL particles)
B  CHGSMHDL = Change in small HDL
C  CHGH345 = change in large HDL cholesterol
D  CHGL2M = change in medium LDL particle concentration
E  CHGLDLSZ = change in LDL diameter (this is the mean for entire LDL population)
F  CHGAPOB = change in apo B
G  CHGHLA = change in hepatic lipase activity
H  VMXMLCHG = change in VO2 max, mL 02 per kg BW per minute
I  VMAXLCHG = change in VO2 max, Liters per minute
J  CHGBMI = change in Body Mass Index (BMI)

The basis of the statistical analysis in physiogenomics is a parallel search for associations between multiple phenotypes and genetic markers for several candidate genes. The summary in Table 3 depicts the data set gathered from the initial application to exercise physiogenomics. In the top panel, each column represents a single phenotype measurement. Each row represents alleles for a given gene, and quantitatively render associations of specific alleles to the variability in the phenotype. The various numbers in the table refer to the negative logarithms of p value times 10. These p values are adjusted for multiple comparisons using the non parametric permutation test described earlier. For example, 30 refers to a p value of <0.001. Because of the large numbers of genes and outcomes that can be found, an interactive program can be prepared that can be used to search a large table with a structure similar to that shown in Table 4. As already noted, the p-value displayed in a cell is generated under the assumption of a linear trend for the effect of an intervention.

The platform allows visual recognition of highly significant association domains. There are also clearly negative fields. The same gene is associated to some phenotypes but not to others Similarly, a given phenotype may have associations to some genes, but not others. Each negative result lends power to the positive associations. Had the populations related to a phenotype being stratified based on confounder founder effects, most genes would have had specific founder alleles overrepresented in that population, and associated with similarly stratified founder phenotypes.

Table 5 above provides information on the association grid. The table lists in order of significance the "hits" of positive association between a gene alleles and a phenotype. The top ranking associations refer to APOA1 and CHGSMH, change in cholesterol, small HDL sub-fraction change (adjusted p of 32 or $p<10^{-3.2}$). Noteworthy also are high ranking associations of APOE to VMAXLCHG, change in maximum oxygen consumption (adjusted p of 30 or $p<10^{-3}$) and to CHGL2M (adjusted p of 23 or $p<10^{-2.3}$). The "InCount" represents individuals with the associated allele, and the "OutCount", individuals without. The counts among various phenotypes may be different depending on measurement sampling during the study. Well represented distributions among the "in" and "out" groups to assure that a given association is not being driven by outliers. In the case of rare side effects, the outliers actually represent the susceptible population associated with a lower frequency predictive marker.

The initial analysis yielded several associations.

Changes in serum lipids were related to APOE haplotype. Specifically, changes in the ratios of lower density lipoprotein to HDL, were greater in the APOE haplotype ⅗ subjects than in those subjects with haplotypes ⅔ and ¾. This demonstrates that the lipid response to an environmental challenge, exercise training, is influenced by APOE haplotype.

Despite the more favorable lipid response to exercise training, the increase in exercise performance was less in the APOE haplotype ⅗ subjects than in the other two genetic groups. This is a novel observation, but suggests that genes related to lipid metabolism affect the increase in exercise performance with exercise training. These results are consistent with animal studies showing reduced exercise capacity and muscle amyloid accumulation in APOE-deficient mice.

The response of the LDL and HDL lipid subfractions to exercise also varied by APOE haplotype. Reductions in small dense LDL, an atherogenic particle, were greatest in APOE haplotype ⅗ subjects.

APOA1 genotypes correlate with a switch of small to large HDL particles in some individuals and of large to small HDL particles in others. The direction of the switch in a given individual correlates with APOA1 genotype.

Small dense LDL particles are atherogenic. Therefore lipoprotein particle subpopulations were analyzed in 106 subjects. Exercise decreased small LDL particle concentration by −13.7±±5.1 mg/dL selectively in those with the APOE ⅗ haplotypes, compared to increases of +5.6±5.2, and +12.6±5.6 mg/dL, respectively, in those with ⅔ and ¾ haplotypes. Surprisingly, maximal oxygen uptake, the best marker of aerobic fitness, increased 9-10% for the entire cohort, but only 5% in the ⅗ subjects vs. 13% in the ⅔ and ¾ groups. This difference in the response of exercise performance to exercise training was significantly different among the haplotypes (p<0.01 for changes). Thus, subjects with APOE ⅗ haplotypes, the most common APOE haplotype in the general population, experienced greater improvement in clinically relevant lipid parameters compared to subjects with APOE haplotypes ⅔ and ¾, despite smaller improvements in cardiorespiratory fitness.

Example 4

Exercise Physiogenomics Incorporating APOA1 Genetic Markers

APOA1 is necessary for nascent HDL generation. Tables 3 and 4 above also demonstrate APOA1 genetic association to Cholesterol (CH) values (LDL, HDL and their sub-fractions). The APOA1 gene has a well-characterized SNP in its promoter, namely, −75 G/A. The data demonstrates that this variant was highly predictive of changes in the concentrations of small and large HDL particles with exercise training. Exercise markedly affects HDL fractions, eliciting a transition from small to large HDL in some individuals and the opposite in others. The presence of the A allele was associated with increased small HDL by 4.7 mg/dL with exercise and decreased large HDL. In contrast, the G/G genotype was associated with increased large HDL concentration by 1.8 mg/dL and decreased small HDL particles. APOA1 appears to be involved in the switch in particle size in response to exercise and the −75A allele of APOA1 is a potential predictor of the polarity of the HDL fraction switch in response to exercise. When translated into a DNA diagnostic, would be useful for the individualization of exercise programs to effect desired changes in lipid profiles of individuals.

Example 5

Results of Model Building

To illustrate the creation of predictive models that are the central part of physiogenomics, a data set was explored to find optimally predictive linear regression models for small LDL particle concentration and small HDL particle concentration. These two response variables have the strongest genetic component observed herein.

The objective of these analyses is to search for genetic markers that modify the effect produced by a particular type of intervention, which epidemiologists refer to as an effect modifier. These are be parameterized in our models as gene-intervention interactions. For example, if $M_i$ is a 0 or 1 indicator of the presence of at least one recessive allele of gene i, and $X_j$ represents the level of intervention, then the entire contribution to the outcome will be given by the contribution of not only the gene and intervention main effects, but their interaction, as well, i.e., $M_i\alpha_i + X_j\beta_j + M_iX_j(\alpha\beta)_{ij}$. Under this model, when the allele is absent ($M_i=0$), the effect of a unit change in the intervention is described by the slope, $\beta_j$, but when the allele is present ($M_i=1$), the effect of a unit change in the intervention is $\beta_j+(\alpha\beta)_{ij}$. Thus, the gene-intervention interaction parameter, $(\alpha\beta)_{ij}$, represents the difference in the effect of the intervention seen when the allele is present.

In the usual modeling framework, the response is assumed to be a continuous variable in which the error distribution is normal with mean 0 and a constant variance. However, it is not uncommon for the outcomes to have an alternative distribution that may be skewed, such as the gamma, or it may even be categorical. In these circumstances, one can make use of a generalized linear model, which includes a component of the model that is linear, referred to as the linear predictor, thus enabling one to still consider the concept of a gene-intervention interaction, as described earlier. The advantage of this broader framework is that it allows for considerable flexibility in formulating the model through the specification of the link function that described the relationship between the mean and the linear predictor, and it also provides considerable flexibility in the specification of the error distribution, as well (McCullagh P, et al. Generalized Linear Models. London: Chapman and Hall, 1989, which is incorporated herein by reference).

To this point, an analysis has been developed in which the effect of the intervention is assumed to be linear, but in practice the effect may take place until a threshold is past, or it may even change directions. Thus, an important component of one's exploration of the intervention effect on a particular response may involve the form for the relationship. In this case one can make use of generalized additive models (GAMs, Hastie et al. *Stat. Sci.* 1:297 (1986)) in which the contribution of the marker and intervention is given by $M_i\alpha_i+\beta(X_j)+M_i\beta_a(X_j)$. In this case, the effect when the allele is absent ($M_i=0$) is $\beta(X_j)$ which is an unspecified function of the level of the intervention. In subject in which the allele is present ($M_i=1$), the effect is given by the function $\beta(X_j)+M_i\beta_a(X_j)$. In practice, these functions may be estimated through the use of cubic regression splines (Durrelman, S et al., *Stat. Med.* 8:551 (1989), which is incorporated herein by reference).

Predictive models may be sought by starting out with a hypothesis (which may be the null model of no marker dependence) and then adding each one out of a specified set of markers to the model in turn. The marker that most improves the p-value of the model is kept, and the process is repeated with the remaining set of markers until the model can no longer be improved by adding a marker. The p-value of a model is defined as the probability of observing a data set as consistent with the model as the actual data when in fact the null-model holds. The resulting model is then checked for any markers with coefficients that are not significantly (at p<0.05) different from zero. Such markers are removed from the model.

For predicting small LDL-C change (CHGLIS) in response to exercise, we started out with the null model, and considered the three categories of variables in Table 6. We arrived at an optimized model, specified in Table 6, containing three markers: baseline small LDL (LIS.1), pre-exercise triglycerides (TGPRE), and two APOE haplotypes (APOE GENE). The model explains 47% of the observed variance for small LDL-C change (CHGL1S) in response to exercise and has a p-value of $4\times10^{-13}$. The p-values for the components are $5\times10^{-14}$ for LIS.1, $8\times10^{-9}$ for TGPRE, $3\times10^{-3}$ for APOE GENE$_1$, and $6\times10^{-2}$ for APOE GENE$_2$. The correlation between the response predicted by the model vs. the observed response for all subjects can be depicted graphically.

TABLE 6

Predictors of Response to Diet, Exercise and Drugs

| Genetic | Physiological | Demographic |
|---|---|---|
| Genotype alpha (gene A) | Baseline Factor 1 | Gender |
| Genotype beta (gene B) | Baseline Factor 2 | Heredity |
| Genotype gamma (gene C) | Baseline Factor 3 | Age |

TABLE 7

Most predictive linear model of small LDL change due to exercise
CHGLIS~L 1S.1 + TGPRE + APOE GENE
[1] Explains: 46.6%
[1] P-value: 4.23e−013

| | Value | StdErr | t value | Pr (>|t|) |
|---|---|---|---|---|
| Intercept | — | 4.1346 | −0.6069 | 5.4530e−001 |
| LIS.1 | — | 0.0832 | −8.7388 | 5.3291e−014 |
| TGPRE | 0.19923 | 0.0316 | 6.2901 | 8.2059e−009 |
| APOEGENE$_1$ | — | 2.7148 | −3.0293 | 3.1126e−003 |
| APOEGENE$_2$ | 3.14274 | 1.6655 10 | 1.88700 | 6.2038e−002 |

For predicting small HDL-C change (CHGSMHDL) in response to exercise, the initial hypothesis was that the response depends on APOA1 genotype, as discovered in the physiogenomics analysis. We also considered the three categories of variables in Table 6, and constructed an optimized model, specified in Table 8, The model contains three markers: two APOA1 genotypes (APOA1.), the pre-exercise small HDL cholesterol concentration (SM HDL.1), and the baseline ratio of fat mass to body mass (PERFAT.1). This model explained 43% of the observed variance for small HDL-C change (CHGSMHDL) in response to exercise and had a p-value of 7x 10-8. The p-values for the components are $9\times10^{-3}$ and $9\times10^{-1}$ for APOA1 genotypes (APOA1.11 and APOA1.12), $1\times10^{-6}$ for SM HDL.1, and $3\times10^{-2}$ for PERFAT.1. The correlation between the response predicted by the model vs. the observed response for all subjects can be depicted graphically.

TABLE 8

Most predictive linear model of small HDL change due to exercise
CHGSMHDL~APOA1.1 + SM HDL.1 + PERFAT.1
[1] Explains: 42.7%
[1] P-value: 6.9e−008

| | Value | StdErr | t value | Pr (>|t|) |
|---|---|---|---|---|
| Intercept | 4.72843 | 2.140831 | 2.20869 | 3.0520e−002 |
| APOA1.11 | 2.00143 | 0.745134 | 2.68599 | 9.0513e−003 |
| APOA1.12 | 0.14581 | 1.035824 | 0.14077 | 8.8846e−001 |
| SMHDL.1 | −0.48786 | 0.092239 | −5.28914 | 1.3722e−006 |
| PERFAT.1 | 0.18331 | 0.085013 | 2.15632 | 3.45479e−002 |

Example 6

Exercise and Markers of Inflammation

The above-described analyses permits the extension of the present examples to additional genes and outcomes. For example, inflammatory markers and their relationship to atherosclerosis are an area of intense interest in clinical medicine. The ability to measure changes in inflammatory markers with exercise training and related genes provides a unique opportunity to examine genes determining the interplay of exercise response and inflammation. The gene probes are derived from candidate genes relevant to energy generation, inflammation, muscle structure, mitochondria, oxygen consumption, blood pressure, lipid metabolism, and behavior, as well as transcription factors potentially influencing multiple physiological axes. The method utilizes blood plasma and DNA from each patient to measure the appropriate genotypes and inflammatory markers in blood.

The inflammatory markers will introduce proteomics to the physiogenomic study of exercise. By profiling at high sensitivity the plasma concentrations of various interleukins, growth factors, and the cellular expression of various receptors, phenotypic components can be added to the analysis. In addition, peripheral white cell monitoring can be included in protocols to demonstrate reporter gene array expression levels. It will also be possible to introduce phenotypic morphometric markers to introduce further bridges between genotype and outcome.

Table 9 provides an example of personalized healthcare by customizing treatment intervention. In the table, the choices are to recommend a given kind of exercise, drug or diet regimen. If one of the options is high scoring, it can be used on its own. Thus in the example, diet is high scoring in the first patient, a drug in the second, and exercise in the fourth. If the options are midrange, they can be used in combination, as is the case in the third patient, where exercise and diet will each have a positive effect but unlikely to be sufficient independently. If none of the options is high or at least mid-scoring, the physiotype analysis suggests that the patient requires another option not yet in the menu. As more options are built into the menu, the greater than chance that all patients will be served at increased precision of intervention and with optimal outcome.

TABLE 9

Personalized Healthcare by Customizing Intervention
Interventions
Physiotype Scores

| Patient No. | Exercise | Drugs | Diet |
|---|---|---|---|
| 1 | 3 | 4 | 7 |
| 2 | 4 | 9 | 5 |
| 3 | 4 | 2 | 5 |
| 4 | 8 | 2 | 3 |

Example 7

Construction of Physiogenomics Array Using Hypothesis-Led Association Screening

In this example, a physiogenomics array consisting of 384 SNPs from 215 genes known to be relevant to certain physiological processes has been designed and tested. The array has been tested on 2000 different samples from different clinical studies for validation of the gene and SNP selection process. After identifying candidate genes through an intensive review of the literature, as well as public databases (db-SNP, ensembl) for validated SNPs with known heterozygosities (HET) for mixed or Caucasian populations. The low HET limit was set to 10% to ensure a sufficient representation of the respective SNP. The high HET limit was set at 30% under the assumption that alleles with a close to even distribution are more likely to be neutral (i.e., not associated with a phenotype). The number of SNPs per gene was based on the length of the gene: <25 kb=1SNP, 25 to 100 kb=2SNPs, >100 kb=3 SNPs. The reference numbers of the identified SNPs were evaluated by Illumina using the electronic OligoDesigner software package, and only SNPs with a score higher than 0.6 were used for the gene array.

Furthermore, the OligoDesigner algorithm uses information from a variety of sources to derive a numerical value intended to score the likelihood of a given assay being developed on the Illumina platform. Some of the criteria used to calculate this value include (1) the presence of adjacent SNPs in the DNA sequence, (2) proximity to the repetitive elements, (3) uniqueness of oligo target sequences, (4) melting temperatures of any oligos selected for the assay, and (5) whether there is any complementation in the 3' regions of the assay oligos. The result of this informatics process is a score between 0 and 1 with assays scoring 0 being disallowed.

While it is often advantageous to construct a physiogenomics array using all 384 SNPs in Table 10, this invention is not limited to such an embodiment. In other embodiments, a physiogenomics array is constructed that contains at least about 10 SNPs taken from Table 10, more preferably at least about 20 SNPs, even more preferably at least about 50 SNPs, even more preferably at least about 100 SNPs, even more preferably at least about 200 SNPs, even more preferably, at least about 300 SNPs.

The 480 samples in this example were run in five different batches of 96 samples each. The DNA was quantitated and normalized using the PicoGreen® quantitation assay. Genotyping was performed strictly according to Illumina® protocols, using a Sentrix®Array Matrix and the Illumina® Beadstation 500. Data were analyzed using GENCALL™ version 6.0.7, and reports were prepared with GTS Reports version 4.1.2.0. Table 10 shows a comprehensive listing of all the SNPs on the array with an indication of the quality of data achieved. Furthermore, a numerical measure of quality is given as the sum over all 5 arrays of the 10% percentile of the GENCALL™ scores, as reported by the Locus report of the GTS Reports. In addition, the following was defined as the quality control(QC) criteria for any given assay: (1) Fail if the p-value of the chi-squared test for Hardy-Weinberg equilibrium is less than 0.02; (2) Fail if the 10% GC score is less than 0.3; (3) Fail if the GENTRAIN™ score is less than 0.4; (4) Fail if the minor allele frequency is zero; 5) Fail if the number of calls is less than 80% of the number of samples. For each SNP assay, the number of runs in which the assay passed these quality control requirements is listed in Table 10, and the results are summarized in Table 11. There is a clear bimodal distribution, with 18% of the assays which never worked, and 36% of the assays that worked in 3 runs. We considered assays that never worked or only worked once as failures, resulting in 99 failed assays for an assay conversion rate of 73%.

TABLE 10

List of the 384 SNPs in the physiogenomics array, CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| apolipoprotein L, 1 | APOL1 | rs136163 | 0.73 | 0.85 | 0.9 | 1 | 2.18 | ACTGCTCTCTAGTTGAAAGA[A/C]GAAAGGATAAGGTTGGAGGA (SEQ ID NO. 1) | 16.1% |
| selectin P (granule membrane protein 140 kDa, antigen CD62) | SELP | rs6136 | 0.1 | 0.07 | 0 | 0 | 2.99 | CAAGAGAATGGCCACTGGTCA[A/C]CTACCGTGCCAACCTGCCAA (SEQ ID NO. 2) | 10.2% |
| cytochrome P450, family 2, subfamily C, polypeptide 19 | CYP2C19 | rs1509676 | 0.15 | 0.26 | 0.28 | 0.14 | 2.49 | CTTTACAACAGGCATAAATTA[A/T]TTCTTCAGAGAAGTTCAATT (SEQ ID NO. 3) | 14.1% |
| lipase, hepatic | LIPC | rs6078 | 0 | 0.03 | 0.08 | 0 | 3.10 | TCCCCTCCTCAGGTGGACGGC[A/G]TGCTAGAAAACTGGATCTGG (SEQ ID NO. 4) | 5.2% |
| kinase insert domain receptor (a type III receptor tyrosine kinase) | KDR | rs2125489 | 0.15 | 0.01 | 0.01 | 0 | 3.46 | GCAGATGTCTTTGTAAAACTC[A/G]TCTCTTTATTCTGGAAATTA (SEQ ID NO. 5) | 12.8% |
| leptin receptor | LEPR | rs1171276 | 0.13 | 0.04 | 0.02 | 0.55 | 2.61 | AGTTTCATGTACATTAAATAT[A/G]AATTTCTTTGGCTGGAAAT (SEQ ID NO. 6) | 25.3% |
| adenosine A2b receptor | ADORA2B | rs758857 | 0.83 | 0.68 | 0.63 | 0.18 | 2.65 | CCTTACTCAGATGCTCTCTGC[A/G]CCCAGTGTGCTAGCCTTGTG (SEQ ID NO. 7) | 22.9% |
| solute carrier family 6 (neurotransmitter transporter, dopamine), member 3 | SLC6A3 | rs3756450 | 0.16 | 0.44 | 0.44 | 0.5 | 2.88 | CCTAAATGCCAAGTCGGCTTT[A/G]TTATCATTGTGGTTGCTGCT (SEQ ID NO. 8) | 13.5% |
| apoptosis, caspase activation inhibitor | AVEN | rs2702285 | 0.86 | 0.53 | 0.47 | 0.07 | 3.09 | AGCTTTCAAATGTCATGCATT[A/G]TGTGGCAGGAGTAGGTTTTA (SEQ ID NO. 9) | 25.3% |
| dystrobrevin binding protein 1 | DTNBP1 | rs1040410 | 0.08 | 0.07 | 0.09 | 0.23 | 2.54 | AAGAGTCCATTCAAAAGGGTT[A/G]TACAGACAGAAAACCAGTGG (SEQ ID NO. 10) | 9.9% |
| glycogen synthase 2 (liver) | GYS2 | rs1505873 | 0.63 | 0.79 | 0.91 | 0.38 | 2.88 | TGCTCAGCCTTCTTCAATGAC[A/G]TGTGTTTTGCTATTGTCTCTA (SEQ ID NO. 11) | 44.8% |
| phosphoinositide-3-kinase, class 2, gamma polypeptide | PIK3C2G | rs1044082 | 0.14 | 0.27 | 0.28 | 0.31 | 3.11 | TTGTTTTTCAAGTTTTTGATTT[A/C]TCTGCTAAAATTCAGACCTG (SEQ ID NO. 12) | 20.6% |
| dopamine beta-hydroxylase (dopamine beta-monooxygenase) | DBH | rs1611115 | 0.83 | 0.78 | 0.84 | 0.88 | 3.29 | CTCTCCCCTCCTGTCCTCTCC[A/G]CAAGTAGACTGAGGGCAGCT (SEQ ID NO. 13) | 20.6% |
| cytochrome P450, family 2, subfamily C, polypeptide 9 | CYP2C9 | rs1799853 | 0 | 0 | 0 | 0 | 0.10 | AGCGGGCTTCCTTCTCCTTGAACAC[A/G]GTCCTCAATGCTCCTCTTCC (SEQ ID NO. 14) | 13.0% |
| chemokine (C-C motif) ligand 2 | CCL2 | rs3760396 | 0.26 | 0.11 | 0 | 0 | 1.65 | GACAGAGAGAGGACCCAAGCA[C/G]GCAACTAGTTGGAGGACTTG (SEQ ID NO. 15) | 22.7% |
| corticotropin releasing hormone receptor 2 | CRHR2 | rs2240403 | | | 0.06 | | 3.11 | TTTCAACTCCTTCCTGCAGTC[A/G]TTCCAGGTGGGGCCTGTGAC (SEQ ID NO. 16) | 7.0% |
| dopamine receptor D1 interacting protein | DRD1IP | rs2298122 | 0.81 | 0.94 | 0.86 | 0.35 | 3.52 | CTCCCCTCCTCTCAGTTCAGGGCT[A/C]TCTTGGGTCCCTGCCAGCTG (SEQ ID NO. 17) | 23.4% |
| Tyrosine hydroxylase | TH | rs6578993 | 0.91 | 0.9 | 0.77 | 0.93 | 2.92 | CCCTCATCTGAAACAAGAACTT[A/G]GAGGCCTGGGCTGCTCCTCC (SEQ ID NO. 18) | 15.1% |
| cholesteryl ester transfer protein, plasma | CETP | rs711752 | 0.5 | 0.4 | 0.4 | 0.22 | 2.52 | TTCAAGGTCAAGTTCTTTGGT[A/G]AGAAGGTCTAGCTGCATTG (SEQ ID NO. 19) | 40.9% |
| lipase, endothelial | LIPG | rs4245232 | 0.81 | 0.54 | 0.42 | 1 | 2.52 | TAAAAAACTAAAGCCCGCCTG[A/G]TCTTGTTAATGAATGATAG (SEQ ID NO. 20) | 20.3% |
| peroxisome proliferative activated receptor, alpha | PPARA | rs5766741 | 0.29 | 0.22 | 0.13 | 0.22 | 3.03 | GCATAAAGGAAGAAAACCATCA[A/G]ATGGTTCAGAATTGGTAAGA (SEQ ID NO. 21) | 28.6% |
| apolipoprotein A-IV | APOA4 | rs5092 | | | | | 2.72 | CAGTGCTGACCAGGTGGCCAC[A/G]TGTAGTGATGTGGACTACTTCAG (SEQ ID NO. 22) | 19.5% |
| phosphoinositide-3-kinase, class 2, beta polypeptide | PIK3C2B | rs7556371 | 0.74 | 0.7 | 0.72 | 0.33 | 2.69 | CCGTTGCTCTTAACCATCTGCC[A/G]AACTTGCACTGCCAGTCATT (SEQ ID NO. 23) | 27.6% |
| scavenger receptor class B, member 2 | SCARB2 | rs3853188 | 0.05 | 0.18 | 0.3 | 0.13 | 2.83 | TTCACATACTGGGAGTTCAG[A/C]ATAGTAAATGTTTTTGAAAA (SEQ ID NO. 24) | 9.6% |
| interleukin 10 | IL10 | rs1800871 | 0.83 | 0.26 | 0.31 | 0.54 | 2.95 | AGCAAACTGAGGCACAGAGATT[A/G]TTACATCACCTGTACAAGGG (SEQ ID NO. 25) | 27.6% |
| cytochrome P450, family 2, subfamily D, polypeptide 6 | CYP2D6 | rs1058167 | 0.32 | | | 0.9 | 2.33 | CCAGCCAGCGCTGGGATGTGC[A/G]GGAGGACGGGACAGCATTC (SEQ ID NO. 26) | 35.2% |
| transforming growth factor, beta 1 (Camurati-Engelmann disease) | TGFB1 | rs1800471 | | | | | 2.26 | TACTGGTGCTGACGCCTGGCC[C/G]GCCGGCCGCGGGACTATCCA (SEQ ID NO. 27) | 11.7% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| cytochrome P450, family 3, subfamily A, polypeptide 4 | CYP3A4 | rs2242480 | 0.08 | 0.26 | 0.25 | 0.89 | 3.02 | ACCCAATAAGGTGAGTGGATG[A/G]TACATGGAGAAGGAGGGAGG (SEQ ID NO. 28) | 15.4% |
| insulin receptor | INSR | rs4804103 | 0.21 | 0.14 | 0.14 | 0.45 | 2.79 | TCCTGTGAGAGAGTTGAGAGC[A/G]ATAATTTAGGGTGGTTATT (SEQ ID NO. 29) | 18.5% |
| histamine receptor H3 | HRH3 | rs1614845 | 0.78 | 0.92 | 0.99 | 0.96 | 2.88 | AAGCTGCTGTAAATGGAGGCT[A/G]CTAGAGAGGAGAGGGCTG (SEQ ID NO. 30) | 18.8% |
| Notch homolog 4 (Drosophila) | NOTCH4 | rs204987 | 0.98 | 1 | 1 | 1 | 3.03 | GGGAGAGCAGTCCTTGCCCGAG[A/G]CAGCCCTGGGCAAGGAGAC (SEQ ID NO. 31) | 2.9% |
| v-akt murine thymoma viral oncogene homolog 2 | AKT2 | rs7247515 | 0.08 | 0.1 | 0.06 | 0.3 | 2.94 | CTAGCACATCTCTTGCCCGAG[A/G]CCTCAGCGTTGCTGTCGC (SEQ ID NO. 32) | 10.7% |
| acetyl-Coenzyme A acetyltransferase 2 (acetoacetyl Coenzyme A thiolase) | ACAT2 | rs2146162 | 0.18 | 0.4 | 0.41 | 0.15 | 2.82 | AAACTAGGAATTACATGGTAA[A/G]TTGAAAGAGGAAGTTAGGGG (SEQ ID NO. 33) | 18.0% |
| cytochrome P450, family 3, subfamily A, polypeptide 5 | CYP3A5 | rs776746 | 0.06 | 0.33 | 0.25 | 0.85 | 2.22 | AAAGAGCTCTTTTGTCTTTCA[A/G]TATCTCTTCCCTGTTTGGAC (SEQ ID NO. 34) | 12.5% |
| lipoprotein lipase | LPL | rs264 | 0.14 | 0.24 | 0.23 | 0.08 | 3.10 | TCTCTTGAAGGTGGGTGGGCC[A/G]CTACCACCAAGAATATCTCC (SEQ ID NO. 35) | 16.4% |
| guanine nucleotide binding protein (G protein), beta polypeptide 3 | GNB3 | rs6489738 | | | | | 3.02 | GCCACTGAGGGGAGAAGGCAC[A/G]GACGTGATGCCGAGATGAT (SEQ ID NO. 36) | 36.5% |
| choline acetyltransferase | CHAT | rs3810947 | 0.06 | 0.68 | 0.52 | 0.58 | 3.18 | ATCTTTTAGAGTCCGACCTCT[A/G]GAAATGTGTATGATGTGA (SEQ ID NO. 37) | 8.9% |
| solute carrier organic anion transporter family, member 1B1 | SLCO1B1 | rs4149056 | 0.16 | 0.16 | 0.1 | 0.01 | 2.85 | CGAAGCATATTACCCATGAAC[A/G]CATATATCCACATGTATGAC (SEQ ID NO. 38) | 15.4% |
| phosphoinositide-3-kinase, class 2, gamma polypeptide | PIK3C2G | rs11043982 | 0.08 | 0 | 0 | 0 | 3.01 | TGCAAAGTTCTGTGACAATAC[A/G]TACTCGGGCTAGAGGTGACT (SEQ ID NO. 39) | 8.1% |
| ATP-binding cassette, sub-family C (CFTR/MRP), member 8 | ABCC8 | rs916829 | 0.88 | 0.86 | 0.94 | 0.99 | 2.96 | CGGGGCTGGCTCTCATTGCTG[A/G]CCTTCACTGTGCACTGTGAG (SEQ ID NO. 40) | 14.3% |
| fatty acid synthase | FASN | rs2228309 | 0.55 | 0.17 | 0.15 | 0.5 | 2.76 | GGTGTTGGGTTCAGCAGGAC[A/G]TTGATGCCCCCACGATGGC (SEQ ID NO. 41) | 45.1% |
| transcriptional adaptor 2 (ADA2 homolog, yeast)-like | TADA2L | rs7211875 | 0.85 | 0.75 | 0.75 | 0.93 | 2.00 | CACTGTACTTACTGCTAAAGG[A/G]ACCCAAACGGTCCATTCCCT (SEQ ID NO. 42) | 34.6% |
| solute carrier family 6 (neurotransmitter transporter, serotonin), member 4 | SLC6A4 | rs140700 | 0.1 | 0.06 | 0.1 | 0.04 | 2.13 | ATCTTTCTGCCACACCACCTC[A/G]CCCTCCTTTCTCAAGGTCTT (SEQ ID NO. 43) | 8.9% |
| low density lipoprotein receptor (familial hypercholesterolemia) | LDLR | rs8110695 | 0.17 | 0.38 | 0.39 | 0.55 | 2.88 | AAACTGAGTCCCAGAAGGATT[A/T]AGTCAGTTACCCAAGTTGTT (SEQ ID NO. 44) | 24.5% |
| lipase A, lysosomal acid, cholesterol esterase (Wolman disease) | LIPA | rs1556478 | 0.25 | 0.86 | 0.69 | 0.26 | 3.38 | CACGGAGACTTATGCACCAGA[A/G]TGAAATGCTGAGATGTTCTT (SEQ ID NO. 45) | 33.3% |
| adrenergic, alpha-1A-, receptor | ADRA1A | rs7816340 | 0.85 | 1 | 1 | 1 | 2.77 | GTCAAGGGTATAACACCTTAG[A/G]GTATAATTTGTTACAGTGTT (SEQ ID NO. 46) | 18.0% |
| tumor necrosis factor receptor superfamily, member 1B | TNFRSF1B | rs235249 | 0.25 | 0.24 | 0.18 | 0.26 | 1.82 | TGCATGAGTGTGTCCGTGTCC[A/G]TGGGGGTGATTGTGGGTAAG (SEQ ID NO. 47) | 26.0% |
| phosphoinositide-3-kinase, class 3 | PIK3C3 | rs7229485 | 0.01 | 0 | 0 | 0.21 | 2.81 | AGAATTTGTATCTCACCAA[A/G]TAATTTTAAAAGGTCATT (SEQ ID NO. 48) | 0.8% |
| adenosine A1 receptor | ADORA1 | rs3766560 | 0.19 | 0.08 | 0.24 | 0.53 | 2.76 | ATGATGTGTGTGGGGAGGAA[A/G]AAGCTTATCAAATCAAAGCC (SEQ ID NO. 49) | 17.4% |
| phosphoinositide-3-kinase, class 2, beta polypeptide | PIK3C2B | rs1877394 | 0.02 | 0.12 | 0.1 | 0.05 | 3.19 | AGTTTGAGACGTGGGTGAAAAC[A/G]TAGGTGGAAAAGTCCAGCAA (SEQ ID NO. 50) | 2.1% |
| apolipoprotein A-IV | APOA4 | rs675 | | | | | 3.22 | GAGAAAGAGCAGGACAAG[A/T]CTCTCCTCCCCTGAGCTG (SEQ ID NO. 51) | 18.8% |
| corticotropin releasing hormone receptor 1 | CRHR1 | rs4792887 | 0.07 | 0 | 0 | 0.3 | 2.64 | CTCTCCAGTGTGCCAAGATC[A/G]AAGATGTACCTGTGACCCC (SEQ ID NO. 52) | 9.6% |
| similar to apoptosis inhibitor 5; fibroblast growth factor 2-interacting factor 2; API5-like 1 | LOC441514 | rs5950584 | | | | 0.58 | 2.56 | CTATCCTCAAATGCTATATAA[A/C]CCAACTGGTGGAAAAAATT (SEQ ID NO. 53) | 4.2% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| cholesteryl ester transfer protein, plasma | CETP | rs3764261 | 0.37 | 0.17 | 0.21 | 0.26 | 2.95 | AGTGAATGAGATAGCAGACAA[A/C]CCAGATGCTACCGACAGGT (SEQ ID NO. 54) | 32.3% |
| adrenergic, beta-1-, receptor | ADRB1 | rs1801252 | 0.16 | 0 | 0 | 0.01 | 0.23 | TTGCTGCCTCCCGCCAGCGAA[A/G]GCCCCGAGCCGTGTCTCAG (SEQ ID NO. 55) | 25.5% |
| cytochrome P450, family 2, subfamily C, polypeptide 19 | CYP2C19 | rs4986894 | | 0.26 | 0.28 | 0.14 | 2.63 | GTGTGTGCCTCTTTGATGGAT[A/G]AAGTGGCAATCACCTAGGC (SEQ ID NO. 56) | 15.1% |
| insulin receptor | INSR | rs891087 | 0.08 | 0.07 | 0.07 | 0.26 | 3.06 | GCAGGTCTCCACACACCTGCC[A/G]TCCAGGTAGAAGTTGCGGCA (SEQ ID NO. 57) | 8.9% |
| phosphoinositide-3-kinase, catalytic, alpha polypeptide | PIK3CA | rs2230461 | | | | | 3.16 | TGAATGGCTGAATTATGATAT[A/G]TACATTCCTGATCTTCCTCG (SEQ ID NO. 58) | 10.2% |
| pyruvate kinase, liver and RBC | PKLR | rs3762272 | 0.25 | 0.18 | 0.31 | 0.43 | 3.11 | AACAAAGATTCTCCTTTCCTC[A/G]TTCACCACTTTCTTGCTGTT (SEQ ID NO. 59) | 4.2% |
| 5-hydroxytryptamine (serotonin) receptor 3B | HTR3B | rs1176744 | | | | | 1.84 | ATAGTGTGGACATTGAAAGAT[A/C]CCCTGACCTTCCCTATGTTT (SEQ ID NO. 60) | 35.7% |
| protein kinase, AMP-activated, gamma 1 non-catalytic subunit | PRKAG1 | rs2293445 | 0.35 | 0.31 | 0.46 | 0.27 | 2.83 | AAAAGTGTTTCCCAGAAACCC[A/G]CCATCCCTTTATCCTTTTAT (SEQ ID NO. 61) | 34.9% |
| apolipoprotein A-II | APOA2 | rs5085 | 0.18 | 0.26 | 0.28 | 0.04 | 2.75 | CAGACTCTAGAGACTGAAATT[C/G]AAGGCCCAGTTCTTGCTGTT (SEQ ID NO. 62) | 16.7% |
| apolipoprotein H (beta-2-glycoprotein I) | APOH | rs8178847 | 0.08 | 0.06 | 0.06 | 0.08 | 2.05 | TACCTACGTTTGCAACACTTC[A/G]TGTTTATAAGCCATCAGCTG (SEQ ID NO. 63) | 8.9% |
| carnitine palmitoyltransferase 1A (liver) | CPT1A | rs2228502 | 0.97 | 0.92 | 0.9 | 0.86 | 3.09 | TTCAGTTTCATCTAACGTCAC[A/G]AAGAAGCGCTGCTTTCTCCAC (SEQ ID NO. 64) | 6.0% |
| nuclear receptor subfamily 3, group C, member 1 (glucocorticoid receptor) | NR3C1 | rs1438732 | 0.18 | 0.09 | 0.09 | 0.17 | 2.82 | TTAGGGACTTTCAAAAACTCA[C/G]ACTCTTGGGTTCTGACCCTG (SEQ ID NO. 65) | 14.8% |
| adrenergic, alpha-2A-, receptor | ADRA2A | rs1800544 | 0.33 | 0.53 | 0.39 | 0.48 | 3.06 | TGGGAGTTGGCCATGCAGCTC[C/G]GGGCCGACGGAGCAGAAGC (SEQ ID NO. 66) | 34.6% |
| adrenergic, beta-2-, receptor, surface | ADRB2 | rs1042713 | 0.15 | 0.31 | 0.38 | 0.44 | 0.00 | GCCTTCTTGCTGGCACCCAAT[A/G]GAAGCCATGCGCCGGACCAC (SEQ ID NO. 67) | 22.4% |
| D-amino-acid oxidase | DAO | rs2070586 | 0.08 | 0 | 0 | 0 | 2.32 | TTGCCAGGAGCTGAGGTCTGC[A/G]GGAGGAGAGTTGTGAGTGAA (SEQ ID NO. 68) | 18.2% |
| choline acetyltransferase | CHAT | rs8178990 | | | | | 1.87 | CCAGCAGGGCCTTGTAGCTGA[A/G]TGCCTTTCAAGAAGATGAGGCTGG (SEQ ID NO. 69) | 5.5% |
| monoamine oxidase B | MAOB | rs1181252 | | | | | 2.83 | AGTTGGCAAGCAGCAACATAGA[A/G]TGGCCTTTTCAAGAAATAAAC (SEQ ID NO. 70) | 3.9% |
| phosphoinositide-3-kinase, class 3 | PIK3C3 | rs4121817 | 0.14 | 0.3 | 0.35 | 0.18 | 2.67 | CAGCACTCCGAATGAAAGGCTG[A/G]CAGTGAAACATGAAAGTTC (SEQ ID NO. 71) | 11.7% |
| retinoic acid receptor, beta | RARB | rs2033447 | 0.11 | 0.2 | 0.22 | 0.58 | 2.85 | ATGCCGGGTGCTAGAGATACA[A/G]CAGTGAACATGACAAAGTTC (SEQ ID NO. 72) | 14.1% |
| apolipoprotein E | APOE | rs439401 | 0.62 | 0.46 | 0.35 | 0.88 | 2.91 | GGAAACTGAGGGGGTGGGAGG[A/G]GAAGAGAGTGCCGGCGGCTC (SEQ ID NO. 73) | 35.7% |
| dystrobrevin binding protein 1 | DTNBP1 | rs2743867 | 0.08 | 0.06 | 0.09 | 0.31 | 2.83 | GATTAAATGCATTCTGCCACA[A/G]TTCTCATTATTTTCATAGTC (SEQ ID NO. 74) | 10.4% |
| glutamate decarboxylase 2 (pancreatic islets and brain, 65 kDa) | GAD2 | rs8190586 | | | | | 2.45 | CACCCGCCATCAATCCTGCCG[A/G]CTCTGGCCGCTCTGCCTCAT (SEQ ID NO. 75) | 3.1% |
| acetyl-Coenzyme A acetyltransferase 1 (acetoacetyl Coenzyme A thiolase) | ACAT1 | rs10890819 | 0.22 | 0.29 | 0.35 | 0 | 2.74 | ACCAGAAAGCTAGCATAATGGA[A/G]TATCGCCCCTCACTTTGTTC (SEQ ID NO. 76) | 31.5% |
| 3-hydroxy-3-methylglutaryl-Coenzyme A reductase | HMGCR | rs3761740 | 0.14 | 0.03 | 0.05 | 0.03 | 3.01 | CGTCAGAAATGTGTGTGGGGI[A/C]CATATTAGTGGTGACAGGTT (SEQ ID NO. 77) | 9.6% |
| dopa decarboxylase (aromatic L-amino acid decarboxylase) | DDC | rs1466163 | 0.83 | 0.99 | 0.99 | 0.93 | 3.20 | GGCTGGTTGGAGCTCTCCCC[A/G]GGCAGCAGCCCTGGTGGAGA (SEQ ID NO. 78) | 10.9% |
| 5-hydroxytryptamine (serotonin) receptor 3B | HTR3B | rs2276307 | 0.17 | 0.18 | 0.3 | 0.08 | 2.64 | CCTTCTCTCTTGGGCCAAGGA[A/G]TTTCTGCTCTATTGCATGTT (SEQ ID NO. 79) | 19.5% |
| platelet/endothelial cell adhesion molecule (CD31 antigen) | PECAM1 | rs1131010 | | | | | 1.33 | AACCTCACTTAACATTTTGGC[A/G]TGGGAATGGCAAATTATCTGC (SEQ ID NO. 80) | 4.7% |
| scavenger receptor class B, member 1 | SCARB1 | rs4765623 | 0.42 | 0.31 | 0.44 | 0.43 | 2.91 | GATTTTGCCCAGTGGCTCTC[A/G]AGGTGGCTGTATCGATGAC (SEQ ID NO. 81) | 36.5% |
| protein kinase, AMP-activated, alpha 1 catalytic subunit | PRKAA1 | rs3792822 | | | | | 2.84 | GATGTGGATACTGAGCCTCGC[A/G]GCTTATATGATTGCTCACAG (SEQ ID NO. 82) | 17.2 |
| apolipoprotein E | APOE | rs429358 | | 0 | 0.01 | 0.02 | 1.38 | GGTACTGCACCAGGCGGCCGC[A/G]CACGTCCTCCATGTCCGCGC (SEQ ID NO. 83) | 26.8% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| nitric oxide synthase 3 (endothelial cell) | NOS3 | rs1549758 | | | | | 2.05 | TGGGTCCCCCGCACAGAGCC[A/G]TCCTGCTGCCGGTAGCCCGC (SEQ ID NO. 84) | 29.4% |
| 5,10-methylenetetrahydrofolate reductase (NADPH) | MTHFR | rs2066470 | | 0.01 | 0.01 | 0.01 | 3.02 | CCGGAGTCTCTCATGCCGCTC[A/G]GGGTCCAGGCCCGGGGTGGA (SEQ ID NO. 85) | 9.6% |
| angiopoietin 1 | ANGPT1 | rs1283694 | 0.86 | 0.88 | 0.9 | 0.88 | 3.13 | CAAACCCTTTCCACTCCATTA[A/T] AAGAACATGAATCCTGATAA (SEQ ID NO. 86) | 17.4% |
| peroxisome proliferative activated receptor, gamma | PPARG | rs1801282 | 0.08 | 0.02 | 0.06 | 0 | 3.48 | CTGGGAGATTCTCCTATTGAC[C/G] CAGAAAGCGATTCCTTCACT (SEQ ID NO. 87) | 12.0% |
| solute carrier family 6 (neurotransmitter transporter, serotonin), member 4 | SLC6A4 | rs2020933 | 0.05 | 0.07 | 0.01 | 0.39 | 3.12 | TTTTTGTCCAGAAAAGTGAACC[A/T] GGTCAATGGATTATTTATGA (SEQ ID NO. 88) | 11.2% |
| phosphofructokinase, platelet | PFKP | rs6901 | 0.66 | 0.74 | 0.86 | 0.69 | 2.49 | AGGACCCATCCTGGATCATCC[A/G]ATGAGCAGCCGTGGCGCTCG (SEQ ID NO. 89) | 28.9% |
| apolipoprotein C-IV | APOC4 | rs2288911 | 0.45 | 0.68 | 0.72 | 0.7 | 3.29 | CTCCGGACGGGCACAGAGAGG[A/C] TTTATAGTGGTTGAGACCCA (SEQ ID NO. 90) | 49.2% |
| adiponectin receptor 2 | ADIPOR2 | rs2058112 | 0.13 | 0 | 0.01 | 0.13 | 2.71 | TCTTCTTGCCCTACATACTTC[A/G]AAAGCCCTTGGAGAAATCCT (SEQ ID NO. 91) | 13.0% |
| catechol-O-methyltransferase | COMT | rs4680 | 0.52 | 0.26 | 0.24 | 0.29 | 2.64 | CGGATGGTGGATTTCGCTGGC[A/G]TGAAGGACAAGGTGTGCATG (SEQ ID NO. 92) | 47.9% |
| selectin P (granule membrane protein 140 kDa, antigen CD62) | SELP | rs6131 | 0.2 | 0.19 | 0.19 | 0.32 | 2.71 | GTCAGCACCTGGAAGCCCCCA[A/G]TGAAGGAACCATGGACTGTG (SEQ ID NO. 93) | 19.8% |
| apolipoprotein L, 3 | APOL3 | rs132653 | 0.86 | 0.98 | 0.98 | 0.37 | 2.80 | GTTCCAGGGTATATCTCAGAG[A/C]CTGGAGAACGTGTCTGGTTA (SEQ ID NO. 94) | 17.4% |
| fms-related tyrosine kinase 1 (vascular endothelial growth factor/vascular permeability factor receptor) | FLT1 | rs2296189 | 0.11 | 0.21 | 0.09 | 0.27 | 3.34 | GATTTTGTCAAAGATAGATTC[A/G]GGGAGCCATCCATTTCAGAGG (SEQ ID NO. 95) | 22.4% |
| dopamine beta-hydroxylase (dopamine beta-monooxygenase) | DBH | rs4531 | | | | | 3.16 | AGGACCCTGGACCCCCGAAGG[A/C]AAGGCCGGCTTCCTCTGGGT (SEQ ID NO. 96) | 7.6% |
| interleukin 1, beta | IL1B | rs1143634 | 0.22 | 0 | 0.07 | 0.1 | 2.57 | AGCTCGTTATCCCATGTGTC[A/G]AAGAAGATAGGTTCTGAAAT (SEQ ID NO. 97) | 20.3% |
| phosphoenolpyruvate carboxykinase 1 (soluble) | PCK1 | rs8192708 | 0.1 | 0 | 0 | 0.03 | 3.03 | AAAGAATCTTGTCCCAACAG[A/G]TTCTGGGTATAACCAACCCT (SEQ ID NO. 98) | 7.6% |
| cytochrome P450, family 3, subfamily A, polypeptide 4 | CYP3A4 | rs2740574 | 0.98 | 1 | 1 | 0.25 | 2.43 | ACAGCCATAGAGACAAGGGCA[A/G]GAGAGAGGCGATTTAATAGA (SEQ ID NO. 99) | 9.1% |
| cytochrome P450, family 2, subfamily D, polypeptide 6 | CYP2D6 | rs7286458 | | | | | 1.35 | ACGCTGGGCTGCACGTACCC[A/G]CCAGGTCCCCTGCCACTGCC (SEQ ID NO. 100) | 7.3% |
| angiotensinogen (serine (or cysteine) proteinase inhibitor, clade A (alpha-1 antiproteinase, antitrypsin), member 8) | AGT | rs5049 | | | | | 2.82 | TGTGTAACTCGACCCTGCACC[A/G]GCTCCACTCTGTTCAGCAGTG (SEQ ID NO. 101) | 11.2% |
| acetyl-Coenzyme A carboxylase alpha | ACACA | rs2229416 | 0.03 | 0 | 0 | 0.17 | 2.96 | GTTAGAGACTGAAAGCTTTCA[A/G]ATGAACAGAATTGATACTGG (SEQ ID NO. 102) | 13.3% |
| dopamine receptor D3 | DRD3 | rs9288993 | | 0 | 0 | 0.23 | 2.77 | GGCAGGTAATGATATTTGTGAC[A/G]TGGAGAATGTGCACTTAGAA (SEQ ID NO. 103) | 5.2% |
| TEK tyrosine kinase, endothelial (venous malformations, multiple cutaneous and mucosal) | TEK | rs600728 | 0.08 | 0.32 | 0.31 | 0.26 | 2.76 | GGCTCCACGACAATGAGTACA[A/G]CTGTGTCCGTGGCTTCTTG (SEQ ID NO. 104) | 9.1% |
| phosphoinositide-3-kinase, class 2, beta polypeptide | PIK3C2B | rs10494851 | 0.01 | 0 | 0 | | 2.84 | AAGGGGACTGTGAGAAAAAAA[A/G]TGTTCATGAGGCTCGAGTCC (SEQ ID NO. 105) | 1.0% |
| v-akt murine thymoma viral oncogene homolog 2 | AKT2 | rs4802071 | 0.73 | 0.68 | 0.63 | 0.76 | 1.57 | CAGTTCAGTTGTTTAGTAT[A/G]TTCAGAGTTGTGCATCCATC (SEQ ID NO. 106) | 34.9% |
| protein kinase, AMP-activated, gamma 2 non-catalytic subunit | PRKAG2 | rs1029947 | 0.12 | 0.41 | 0.52 | 0.33 | 3.22 | GTTGGCTCTACTCATTTCCTC[A/G]TCGTCATTCTCTTGTAGTCA (SEQ ID NO. 107) | 14.8% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| cytochrome P450, family 1, subfamily A, polypeptide 2 | CYP1A2 | rs2470890 | 0.64 | 0.12 | 0.18 | 0 | 3.41 | AGAATGGTGGTGICTTCTTCA[A/G]TTGATGGAGAAGCGCAGCCG (SEQ ID NO. 108) | 43.2% |
| cytochrome P450, family 3, subfamily A, polypeptide 4 | CYP3A4 | rs12333983 | 0.12 | 0.34 | 0.3 | 0.84 | 2.37 | AATTAGATTGGAAATGGATGTA[A/T]CCGTGTATATTCATACCCTT (SEQ ID NO. 109) | 23.2% |
| paraoxonase 1 | PON1 | rs662 | 0.36 | 0.57 | 0.68 | 0.78 | 3.43 | ATTTTCTTGACCCTACTTAC[A/G]ATCCTGGGAGATGTATTTGG (SEQ ID NO. 110) | 34.4% |
| apolipoprotein C-III | APOC3 | rs4520 | 0.24 | 0.12 | 0.3 | 0.26 | 2.52 | CTTGGTGGCGTGCTTCATGTA[A/C]CCCTGCATGAAGCTGAGAAG (SEQ ID NO. 111) | 29.4% |
| microsomal triglyceride transfer protein (large polypeptide, 88 kDa) | MTP | rs3816873 | 0.24 | 0.12 | 0.21 | 0.26 | 3.66 | CGCCCCTTTACCTTTCCATGG[A/G]TTAGATGAAGGAGCGTAGGT (SEQ ID NO. 112) | 25.0% |
| phosphoinositide-3-kinase, catalytic, gamma polypeptide | PIK3CG | rs4727666 | 0.84 | 0.87 | 0.96 | 0.52 | 3.07 | GCTCTTAGAACTAGCTACAAA[A/G]ATATTTCATATGTTTATGTC (SEQ ID NO. 113) | 26.0% |
| apoptosis, caspase activation inhibitor | AVEN | rs504714 | 0.95 | 0.91 | 0.88 | 0.4 | 3.30 | ACTTGTAATTATGCGTGGAGT[A/T]GTTAACTGTATTTTTTACAC (SEQ ID NO. 114) | 6.5% |
| peptide YY | PYY | rs231460 | 0.09 | 0.01 | 0.02 | 0.02 | 2.42 | TGCTCACCCTAGGATGGAGGG[A/G]CAGTGGGGCTGGTTAGGA (SEQ ID NO. 115) | 22.1% |
| selectin E (endothelial adhesion molecule 1) | SELE | rs5361 | 0.09 | 0.01 | 0.02 | 0.02 | 1.73 | GCCTGTACCAATACATCCTGC[A/C]GTGGCCACGGTGAATGTGTA (SEQ ID NO. 116) | 30.5% |
| cytochrome P450, family 2, subfamily C, polypeptide 19 | CYP2C19 | rs11188092 | 0.2 | 0.02 | 0 | 0.26 | 2.87 | GCAAGCCCTATTAGACATATA[A/C]TTTTCCCAACTTTTCCCTTT (SEQ ID NO. 117) | 21.9% |
| phosphoinositide-3-kinase, catalytic, beta polypeptide | PIK3CB | rs10513055 | 0.2 | 0.01 | 0 | 0.1 | 3.36 | GGGTAGGAAAATTAAGTGAATA[A/C]TTTTTGTGATCCAAGAAAGA (SEQ ID NO. 118) | 18.5% |
| apolipoprotein A-I | APOA1 | rs4225 | | | | | 2.83 | CTTTTAAGCAACTACAGGGG[A/C]AGCCCTGGAGATTGCAGGAC (SEQ ID NO. 119) | 45.1% |
| interleukin 10 | IL10 | rs3024492 | | | | | 2.86 | GAAATGAGCAAGAGATCTGAC[A/T]CCAGGAGTCTTTCCTCATTT (SEQ ID NO. 120) | 24.2% |
| glycogen synthase kinase 3 beta | GSK3B | rs10934502 | 0.06 | 0.49 | 0.5 | 0.36 | 2.98 | GCTTCCTTATGTAAAATTGAG[A/G]TATTTCTAAAGTAACGCAAT (SEQ ID NO. 121) | 22.4% |
| Fms-related tyrosine kinase 1 (vascular endothelial growth factor/vascular permeability factor receptor) | HIF1A | rs2301108 | 0.94 | 0.78 | 0.76 | 0.19 | 3.12 | CTACTGGAAGATTAGCCACGT[A/G]TTGAGTTTTGTCTTTGCATT (SEQ ID NO. 122) | 12.8% |
| ATP-binding cassette, sub-family B (MDR/TAP), member 1 | ABCB1 | rs1128503 | 0.61 | 0.31 | 0.42 | 0.88 | 3.03 | ACTCTGCACCTTCAGGTTCAG[A/G]CCCTTCAAGATCTAXCAGGA (SEQ ID NO. 123) | 39.6% |
| apolipoprotein B (including Ag(x) antigen) | APOB | rs3791981 | 0.1 | 0.07 | 0.04 | 0.49 | 3.51 | TTTTCCAAAGATGATCTCTCC[A/G]GAGCTATTGTTCTTCATTC (SEQ ID NO. 124) | 12.8% |
| phosphoinositide-3-kinase, regulatory subunit 1 (p85 alpha) | PIK3R1 | rs10515070 | 0.25 | 0.8 | 0.76 | 0.44 | 3.12 | AGATTCCTCCCTGTACGATAG[A/T]GTCTTACTTACTTTTCCACTTTGC (SEQ ID NO. 125) | 29.2% |
| insulin receptor substrate 1 | IRS1 | rs1801123 | 0.05 | 0.26 | 0.33 | 0.42 | 3.24 | CCTTTCTCTATGCTGCAACAGC[A/G]GATGATTCTTCCTCTTCCAC (SEQ ID NO. 126) | 14.3% |
| melanocortin 3 receptor | MC3R | rs6024725 | 0.33 | 0.21 | 0.27 | 0.62 | 3.14 | CCTAGAGACATATCCAGTTA[A/G]TTTTAGCCTCCACCAGTATT (SEQ ID NO. 127) | 33.3% |
| cholinergic receptor, muscarinic 3 | CHRM3 | rs7520974 | 0.53 | 0.46 | 0.51 | 0.75 | 3.50 | CAGCTGAAAGAAAGACAAATA[A/G]TAGAATACCCAGTCTTTACCA (SEQ ID NO. 128) | 43.5% |
| apolipoprotein L, 2 | APOL2 | rs1001293 | 0.12 | 0.01 | 0.15 | 0.49 | 3.08 | TTCCTTGACCTCCGTCGTCTCGG[A/T]TGGGAAACCCAGTCTTACCA (SEQ ID NO. 129) | 12.8% |
| lipase A, lysosomal acid, cholesterol esterase (Wolman disease) | LIPA | rs6586179 | 0.11 | 0.04 | 0.09 | 0.18 | 3.28 | ACCCTGCATTCTGAGGGGTCT[A/G]GAGGGAAACTGACAGCTGTG (SEQ ID NO. 130) | 10.4% |
| leptin receptor | LEPR | rs8179183 | 0.1 | 0.02 | 0.13 | 0.13 | 3.48 | TAATGGAGATACTATGAAAAA[C/G]GAGAAAAAATGTCACTTTACT (SEQ ID NO. 131) | 21.1% |
| ATP-binding cassette, sub-family B (MDR/TAP), member 1 | ABCB1 | rs2032582 | 0.61 | 0.5 | 0.48 | 1 | 2.76 | TAGTTTGACTCACCTTCCCAG[A/C]ACCTTCTAGTTCTTTCTTAT (SEQ ID NO. 132) | 38.5% |
| lipase, hepatic | LIPC | rs936960 | 0.88 | 1 | 1 | 0.77 | 2.87 | CAGAGCACGAGGCTGATTTTC[A/C]ATCCCAGTGTGGGCCACC (SEQ ID NO. 133) | 11.5% |
| peroxisome proliferative activated receptor, gamma | PPARG | rs4135268 | 0.04 | 0.06 | 0.09 | 0.03 | 3.33 | ATTAACCCATGGTCCAGAAAT[C/G]ATGGGTTGTTAAATGACCAA (SEQ ID NO. 134) | 6.0% |
| hypothetical protein MGC4093 | MGC4093 | rs1982072 | 0.69 | 0.53 | 0.47 | 0.82 | 2.78 | TACGATTCTCACCCCATATTT[A/T]CAAGCCTAGTCCAAGGATTA (SEQ ID NO. 135) | 33.1% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| retinoic acid receptor, alpha | RARA | rs4890109 | 0.05 | 0 | 0 | 0 | 3.41 | GGCTGCTCAGGGCCTCGTCCA[A/C]CCCCAGCCTGACAGAGAGCT (SEQ ID NO. 136) | 2.9% |
| angiotensin II receptor, type 1 | AGTR1 | rs931490 | 0.81 | 0.84 | 0.86 | 0.98 | 2.01 | GGGGCCCCTGACTTCTGCT[A/G]GAATTTAGATTTAAATAGAT (SEQ ID NO. 137) | 25.0% |
| platelet/endothelial cell adhesion molecule (CD31 antigen) | PECAM1 | rs4072032 | 0.63 | 0.51 | 0.51 | 0.89 | 2.80 | AGTGCCGATATACATTAAGT[A/G]CTTAATAAATGACTGCTACC (SEQ ID NO. 138) | 46.6% |
| angiotensin I converting enzyme (peptidyl-dipeptidase A) 1 | ACE | rs4333 | 0.51 | 0.77 | 0.56 | 0.45 | 3.38 | CTGACCCCAAGAGGAGGGGA[A/G]CCCAACTCTGTGCTCTCACC (SEQ ID NO. 139) | 47.4% |
| neuropeptide Y | NPY | rs1468271 |  | 1 | 1 | 1 | 2.66 | GACCCTGTAATTTCAGAAAC[A/G]CACATAGGAGTGGGTGTCTG (SEQ ID NO. 140) | 4.9% |
| titin.cap (telethonin) | TCAP | rs931992 | 0.7 | 0.52 | 0.58 | 0.1 | 2.50 | TACCTGGACGCTGGCTGCCCC[A/C]CGGTCAGAGGTCTGGGGTCC (SEQ ID NO. 141) | 39.3% |
| pyruvate kinase, muscle | PKM2 | rs2856929 | 0.21 | 0.42 | 0.28 | 0.15 | 2.46 | CAGGCTCAGGGTCTAAATTCC[A/G]TATCCTTTTCTTCCATACCCT (SEQ ID NO. 142) | 19.3% |
| dopamine receptor D3 | DRD3 | rs167771 | 0.83 | 0.78 | 0.82 | 0.13 | 3.22 | TGCTCCAAAGTTCATCTTTTCCACAAT[A/G]ATCCTCTTTTCCATAAGCC (SEQ ID NO. 143) | 24.5% |
| phosphoinositide-3-kinase, catalytic, alpha polypeptide | PIK3CA | rs1356413 | 0.02 | 0.05 | 0.03 | 0.08 | 2.96 | TTTAGACATATGCCTCTATAT[C/G]CTTCTATAATTATTAATAGT (SEQ ID NO. 144) | 4.4% |
| apolipoprotein L, 5 | APOL5 | rs2076672 | 0.2 | 0.06 | 0.06 | 0.04 | 0.87 | CTCAGTTCTCTCTGTCTC[A/G]TCCTTGCCCATCTCCAGG (SEQ ID NO. 145) | 39.3% |
| lipase, hepatic | LIPC | rs417344 | 0.09 | 0.09 | 0.07 | 0.07 | 3.08 | TTTCCTAATTTGCAGTTGAGA[A/G]TTTAAGAGGTTGGGAACTGG (SEQ ID NO. 146) | 14.8% |
| tumor necrosis factor receptor superfamily, member 1A | TNFRSF1A | rs4149578 | 0.11 | 0.31 | 0.15 | 0.33 | 1.23 | ATGGGGCCCTGGGAGGAGAGC[A/G]TGGCAAGTTCTCAGCATTCG (SEQ ID NO. 147) | 12.5% |
| glycogen synthase 1 (muscle) | GYS1 | rs2287754 | 0.07 | 0.1 | 0.03 | 0.02 | 2.87 | CGGGAAGCTTGCAAGACGCTC[A/G]CTTCCTATTGCAAGACCGC (SEQ ID NO. 148) | 8.9% |
| disrupted in schizophrenia 1 | DISC1 | rs821616 | 0.31 | 0.14 | 0.07 | 0.39 | 3.69 | GCTTGTCGATTGCTTATCCAG[A/T]GCCTACAGCTCCAGGAAGCC (SEQ ID NO. 149) | 25.3% |
| phosphofructokinase, platelet | PFKP | rs10508244 | 0.06 | 0.08 | 0.11 | 0.21 | 2.67 | CACACACTAACATGCAGAAAC[A/G]TACTACCTCACCACTCAAATG (SEQ ID NO. 150) | 10.2% |
| lipoprotein lipase | LPL | rs268 | 0.01 | 0 | 0 | 0 | 3.13 | ACAAATCTGGGCTATGAGATCA[A/G]TAAAGTCAGAGCCAAAAGAA (SEQ ID NO. 151) | 1.0% |
| intercellular adhesion molecule 1 (CD54), human rhinovirus receptor | ICAM1 | rs1801714 |  |  |  |  | 0.24 | TTCAGCAGGAGCTGGGCCCTC[A/G]GGCCCAGTGGCTGGGCTGGA (SEQ ID NO. 152) | 2.6% |
| cholesteryl ester transfer protein, plasma | CETP | rs5880 | 0.05 | 0 | 0 | 0 | 2.85 | GATATCGTGACTACCGTCCAG[C/G]CCTCCTATTCTAAGAAAAGC (SEQ ID NO. 153) | 5.7% |
| scavenger receptor class B, member 1 | SCARB1 | rs10846744 | 0.14 | 0.63 | 0.6 | 0.81 | 3.11 | TAGCTTATCAGGTTTATTGCT[C/G]TCCATCTGTATCACCTGCCT (SEQ ID NO. 154) | 19.0% |
| apolipoprotein M | APOM | rs707922 |  |  |  |  | 3.19 | CCTGTTTATGAGATTTTAAC[A/C]CCTTACCTTGATTCCTAGGA (SEQ ID NO. 155) | 10.4% |
| growth hormone releasing hormone | GHRH | rs6032470 | 0.16 | 0.24 | 0.24 | 0.61 | 3.15 | GGGGGCCCCTGGGAC[A/G]GTGGGAAGCCTTAACAACAT (SEQ ID NO. 156) | 16.1% |
| solute carrier family 12 (potassium/chloride transporters), member 4 | SLC12A4 | rs7200210 | 0.06 | 0 | 0.01 | 0.48 | 3.14 | CAAGAGCTCCCTACCCAGGAA[A/G]CCCAAGCCTCACCCAGAATG (SEQ ID NO. 157) | 7.0% |
| cytochrome P450, family 2, subfamily D, polypeptide 6 | CYP2D6 | rs1135821 |  |  |  |  | 0.00 | CCCTTGGGAAGCGGCCCGAA[A/G]CCCAGGATCTGGGTGATGGG (SEQ ID NO. 158) | 1.0% |
| interleukin 1 receptor, type I | IL1R1 | rs2192752 | 0.13 | 0.17 | 0.34 | 0.13 | 3.66 | CCTTTTAATGGCCATCAATAA[A/C]ACAGCCTGACTAGTTCAACA (SEQ ID NO. 159) | 22.4% |
| cholecystokinin A receptor | CCKAR | rs3822222 | 0.06 | 0.04 | 0.11 | 0.2 | 3.04 | AAACTGACCTCCAACATGGAT[A/G]ATGGGGACCGACTTGTGGGG (SEQ ID NO. 160) | 13.3% |
| gamma-aminobutyric acid (GABA) A receptor, alpha 4 | GABRA4 | rs1398176 |  |  |  |  | 3.39 | AAATAAAAAGAATTGCAGCCCA[A/G]TGTGGGGTAAGTAAAAGGAT (SEQ ID NO. 161) | 16.9% |
| acetyl-Coenzyme A carboxylase alpha | ACACA | rs8081866 | 0.79 | 0.69 | 0.64 | 0.38 | 2.97 | GAGAAGCTCCCATCTAGCTGT[A/G]TATGATAGGGGGTTTATCTG (SEQ ID NO. 162) | 24.0% |
| ornithine aminotransferase (gyrate atrophy) | OAT | rs2807071 | 0.82 | 0.97 | 0.92 | 0.93 | 3.22 | GGTTAGGGAGACTAGCAATTA[A/G]TTGAAGAGATGTAGTTTGAC (SEQ ID NO. 163) | 16.1% |
| apolipoprotein L, 4 | APOL4 | rs2005590 | 0.23 | 0.09 | 0.07 | 0.49 | 2.07 | TGCCTGATTTTGTCACTGAAC[A/G]ATGAGCATGATTTTTCCAGG (SEQ ID NO. 164) | 26.8% |
| phosphoinositide-3-kinase, catalytic, alpha polypeptide | PIK3CA | rs7641983 | 0.18 |  |  | 0.4 | 2.48 | CTCATAAAGAGCCAGACAAAA[A/G]GAAAAAAACCCAGAAATTA (SEQ ID NO. 165) | 26.0% |
| Williams Beuren syndrome chromosome region 14 | WBSCR14 | rs6967107 | 0.1 | 0 | 0 | 0.07 | 1.60 | GGAAATCTCACAGGCCTTCACC[A/C]CTCTCCCCTGCCCTTTCTCA (SEQ ID NO. 166) | 6.5% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| hypothetical protein FLJ32252 | FLJ32252 | rs619698 | 0.65 | 0.24 | 0.26 | 0.73 | 2.35 | TGGGACAGGTGCGCTCCCAGA[A/C]GGGATCCTGTCGCCAGTTCT (SEQ ID NO. 167) | 38.5% |
| gamma-aminobutyric acid (GABA) A receptor, alpha 2 | GABRA2 | rs1442061 | 0.25 | 0.07 | 0.06 | 0.28 | 3.16 | GGGTGTGCCCTCTAGATTTAG[C/G]CAGAGATCTATCCAGTGTAT (SEQ ID NO. 168) | 25.3% |
| glycogen synthase kinase 3 beta | GSK3B | rs4688046 | 0.06 | 0.48 | 0.5 | 0.36 | 3.01 | TAGTAAACTATTTCTTCCCAT[A/G]GGGAGAAGATGGATTCTTTTC (SEQ ID NO. 169) | 21.6% |
| tyrosine hydroxylase | TH | rs3842726 | | 1 | 1 | | 2.17 | GCCCCACATCTGTGCCACAGA[C/G]ACAGACCCTGGGATCCTCAG (SEQ ID NO. 170) | 3.9% |
| 5-hydroxytryptamine (serotonin) receptor 5A | HTR5A | rs1440451 | 0.99 | 1 | 1 | 0.46 | 2.63 | CTTGTTCAATGAGATTATA[C/G]CTGATCTGACGTGAGAATGC (SEQ ID NO. 171) | 3.6% |
| paraoxonase 1 | PON1 | rs854572 | 0.56 | 0.48 | 0.41 | 0.05 | 2.67 | GGTGCCTCTGTACAACCATGT[C/G]TCTCTTCTCTGCTGTCTGCT (SEQ ID NO. 172) | 47.7% |
| paraoxonase 1 | PON1 | rs3917550 | 0.18 | 0.04 | 0.08 | 0.1 | 2.91 | AGCAACGTCTTGCTGTTTTTC[A/G]GAGGTAGAGGGCTGCTTTCT (SEQ ID NO. 173) | 13.5% |
| uncoupling protein 3 (mitochondrial, proton carrier) | UCP3 | rs826082 | 0.01 | 0 | 0 | 0.54 | 2.76 | GCCCCACCCACTCTCCTGACT[A/T]TCGGGAGCAAACCAGTAGAG (SEQ ID NO. 174) | 4.2% |
| 5-hydroxytryptamine (serotonin) receptor 7 (adenylate cyclase-coupled) | HTR7 | rs1891311 | 0.1 | | 0.18 | 0.17 | 0.3 | 3.49 | AATGACCGGTTATACTCTTCT[A/G]TAAAGGAATCCTGGAGGTGT (SEQ ID NO. 175) | 6.8% |
| cholinergic receptor, nicotinic, alpha polypeptide 7 | CHRNA7 | rs3087454 | | | | | 3.28 | TAGCCATACTCCAGAAAAAAT[A/C]AATAAATTCCCTTGGCCCCA (SEQ ID NO. 176) | 34.4% |
| ATP-binding cassette, sub-family G (WHITE), member 5 (sterolin 1) | ABCG5 | rs4148189 | 0.09 | 0.08 | 0.07 | 0.64 | 3.29 | TTCAACAAGCCTGCTTACTGC[A/G]GTTAGTTGTGACCATTGTCT (SEQ ID NO. 177) | 16.7% |
| cholesteryl ester transfer protein, plasma | CETP | rs1800776 | | | | | 0.01 | ATGATCTCAGAGCGTGTATAC[A/C]CACCCAGAGTTATTTATGC (SEQ ID NO. 178) | 6.8% |
| glutamate decarboxylase 1 (brain, 67 kDa) | GAD1 | rs3791850 | 0.18 | 0.03 | 0.07 | 0.14 | 2.94 | CACAACAAGGGTTTAGCTCTA[A/G]GGGAGCAGAGGCAGGATGA (SEQ ID NO. 179) | 22.1% |
| angiotensin I converting enzyme (peptidyl-dipeptidase A) 1 | ACE | rs4305 | 0.6 | 0.71 | 0.52 | 0.08 | 2.52 | ATTGAGTGGCTGGGGCCTGGC[A/G]CAGCCAGAAATGACAGTGGC (SEQ ID NO. 180) | 46.9% |
| apoptosis, caspase activation inhibitor | AVEN | rs563895 | 0.89 | 0.78 | 0.74 | 0.31 | 3.29 | GCCAATGCAGATTTATCCTCC[A/G]CCCTTCTCCAACCTGTTCTA (SEQ ID NO. 181) | 16.1% |
| glutamate decarboxylase 2 (pancreatic islets and brain, 65 kDa) | GAD2 | rs7072137 | 0.18 | 0.06 | 0.02 | 0.32 | 3.14 | TGCTCACTATATGCCAATAGC[A/G]TCCCACAACCACTGATTGTG (SEQ ID NO. 182) | 9.9% |
| neuropeptide Y receptor Y5 | NPY5R | rs11100494 | 0.08 | 0.13 | 0.14 | 0.1 | 3.42 | CAGAAAGATGTCATCATCCAG[A/C]ATTGCGTCCACAGTCAAC (SEQ ID NO. 183) | 7.0% |
| cytochrome P450, family 3, subfamily A, polypeptide 5 | CYP3A5 | rs4646450 | 0.18 | 0.34 | 0.27 | 1 | 3.44 | GAGGCGAGGAGCGCTATTGCA[A/G]TGCCACGTGAAGTGAATTGT (SEQ ID NO. 184) | 20.8% |
| intercellular adhesion molecule 1 (CD54), human rhinovirus receptor | ICAM1 | rs5491 | 0 | 0.08 | 0.06 | 0.25 | 3.21 | GCACCTCCTGTGACCAGCCA[A/T]GTTGTTGTGGCATAGAGACCC (SEQ ID NO. 185) | 2.6% |
| glycogen synthase 1 (muscle) | GYS1 | rs5447 | | | | | 2.19 | CTGGTTGGGAGCCTTCCCGAC[A/G]TGAACAAGATGCTGGATAAG (SEQ ID NO. 186) | 0.0% |
| malate dehydrogenase 1, NAD (soluble) | MDH1 | rs1255 | 0.81 | 0.99 | 0.97 | 0.99 | 3.36 | CGAACAAGGACGCTTTGAAGA[A/G]TGTGGAATTACTGTGCAAGGA (SEQ ID NO. 187) | 28.1% |
| dopamine receptor D2 | DRD2 | rs2471857 | 0.17 | 0.5 | 0.42 | 0.17 | 2.71 | CTTCCCAGTTGCACTAACAGA[A/G]CCTTTGATTCAGTTCAGCAA (SEQ ID NO. 188) | 18.8% |
| gamma-aminobutyric acid (GABA) A receptor, alpha 4 | GABRA4 | rs3762611 | 0.07 | 0.14 | 0.19 | 0.07 | 2.60 | CTCTCTGTTTGGGAAAAATA[A/G]CGGAAGAACTAGTGTATCCT (SEQ ID NO. 189) | 9.6% |
| glutamate decarboxylase 1 (brain, 67 kDa) | GAD1 | rs701492 | 0.27 | 0.3 | 0.3 | 0.23 | 1.64 | GGAGGGAAATTAAAATGAAGA[A/G]TCAATGAGATTGCACATGAA (SEQ ID NO. 190) | 16.9% |
| acetyl-Coenzyme A acetyltransferase 1 (acetoacetyl Coenzyme A thiolase) | ACAT1 | rs11212515 | 0.22 | 0.31 | 0.35 | 0.01 | 2.84 | GGATTGCAATAAAGGGAAGGA[A/T]GAAGGATGATTTTGGCTTGA (SEQ ID NO. 191) | 31.0% |
| cholinergic receptor, muscarinic 1 | CHRM1 | rs2067477 | 0.1 | 0.14 | 0.06 | 0 | 2.64 | TACCACGTACCTGCTCATGGG[A/C]CACTGGGCTCTGGGCACGCT (SEQ ID NO. 192) | 11.2% |
| selectin P (granule membrane protein 140 kDa, antigen CD62) | SELP | rs1800808 | 0.13 | 0.18 | 0.21 | 0.01 | 3.60 | ATGTGAATAATAAGGATAATA[A/G]TCACCAAATACATAGACATG (SEQ ID NO. 193) | 11.7% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| cholesteryl ester transfer protein, plasma | CETP | rs1532624 | 0.51 | 0.29 | 0.36 | 0.1 | 3.16 | TCTGCCCCTTTGGGCTGCAGC[A/C]TCACAAGCTGTGTGGCGTTG (SEQ ID NO. 194) | 40.1% |
| adrenergic, beta-2, receptor, surface | ADRB2 | rs1042718 | 0.19 | 0.34 | 0.52 | 0.35 | 2.91 | CCCATTCAGATGCACTGGTAC[A/C]GGGCCACCCACCAGGAAGCC (SEQ ID NO. 195) | 19.5% |
| retinoid X receptor, alpha | RXRA | rs3118536 | 0.84 |  |  |  | 2.14 | CTGCAGGTGCACGGTTCCTG[A/C]TTGCCCAGGTGTCTGAGC (SEQ ID NO. 196) | 19.0% |
| apolipoprotein E | APOE | rs405509 | 0.5 | 0.34 | 0.25 | 0.76 | 2.70 | GAGGACACCTCGCCAGTAAT[A/C]CAGACACCCTCCTCCATTCT (SEQ ID NO. 197) | 46.6% |
| phosphoinositide-3-kinase, catalytic, gamma polypeptide | PIK3CG | rs849404 | 0.09 | 0.06 | 0.02 | 0.23 | 3.31 | TCTGGTTGAATAAAGGTTCTT[A/G]AAAACCTCCTGAGTCAGGAC (SEQ ID NO. 198) | 13.5% |
| protein kinase, AMP-activated, gamma 2 non-catalytic subunit | PRKAG2 | rs6960931 | 0.08 | 0.2 | 0.14 | 0.23 | 3.44 | TCTGGGAAATGCAAGGCACAC[A/G]GCCAAGTGTGTGGGGTAG (SEQ ID NO. 199) | 11.5% |
| adenosine A1 receptor | ADORA1 | rs903361 | 0.68 | 0.51 | 0.64 | 0.68 | 3.44 | AGTGGTCAGGCTTCACCCAGT[A/G]TACAGAGACGATCTGGGAC (SEQ ID NO. 200) | 37.8% |
| phosphofructokinase, muscle | PFKM | rs2269935 | 0.15 | 0.28 | 0.21 | 0.05 | 3.47 | CGGCAATTAGACTGGCTAGAG[A/C]CACCTCAGTCAGGCTCTCC (SEQ ID NO. 201) | 22.7% |
| retinoid X receptor, alpha | RXRA | rs3750546 |  |  |  |  | 1.43 | CCTGAGGATGAAGGGGCGTCC[A/G]TGGCCAGGCAGCAGTGAGAA (SEQ ID NO. 202) | 12.0% |
| lipase, hormone-sensitive | LIPE | rs1042283 | 0.03 | 0.07 | 0.03 | 0.33 | 0.89 | GGAAGGAACCTCGTACATCCT[A/G]CGGGGCAGTGGGGACAGCGT (SEQ ID NO. 203) | 26.0% |
| phosphoinositide-3-kinase, class 2, beta polypeptide | PIK3C2B | rs2292459 | 0.8 | 0.48 | 0.51 | 0.41 | 1.67 | ATTCTCTTTCTCCCTTTCTTC[A/G]AAACAGGCCCTGAAGTATGA (SEQ ID NO. 204) | 6.3% |
| cytochrome P450, family 3, subfamily A, polypeptide 5 | CYP3A5 | rs15524 | 0.07 | 0.33 | 0.27 | 0.76 | 3.05 | TTCTTGAAGACCAAAGTAGAA[A/G]TCTTAGAATAACTCATTCT (SEQ ID NO. 205) | 12.2% |
| paraoxonase 1 | PON1 | rs705381 | 0.02 | 0.86 | 0.84 | 0 | 2.48 | GGTGGGGGCTGACCGCAAGCC[A/G]CGCCTTCTGTGCACCTGGTC (SEQ ID NO. 206) | 26.0% |
| acetyl-Coenzyme A carboxylase beta | ACACB | rs2430683 | 0.94 | 0.91 | 0.84 | 0.72 | 2.96 | CCAGCAAACACCAGGCTACCA[A/C]GGATCCAAAGATGCCAAAA (SEQ ID NO. 207) | 12.0% |
| dopamine receptor D3 | DRD3 | rs167770 | 0.71 | 0.67 | 0.76 | 0.28 | 2.80 | TGGCTTCAGCTTGTAAAGCTT[A/G]GAAAACATTCTGAAACAACAT (SEQ ID NO. 208) | 34.1% |
| dopamine receptor D5 | DRD5 | rs2867383 | 0.33 | 0.52 | 0.43 | 0.5 | 0.77 | GCCTGTGGTCACAGAGCTCCT[A/G]AGTGGCAGAACTCAACTTGA (SEQ ID NO. 209) | 33.3% |
| similar to SALL4B | LOC391530 | rs10460960 | 0.92 | 0.73 | 0.71 | 0.59 | 2.55 | CCATACTGAAAATGCTAGTCC[A/G]CCAAGCACACTTTGAGATCA (SEQ ID NO. 210) | 12.8% |
| TEK tyrosine kinase, endothelial (venous malformations, multiple cutaneous and mucosal) | TEK | rs617333 | 0.89 | 1 | 1 | 0.96 | 3.16 | TGAAATCCTTTTCCCTGCTTT[A/C]TCCCAGCACTTGGGGGATGT (SEQ ID NO. 211) | 15.6% |
| glycogen synthase kinase 3 beta | GSK3B | rs334555 | 0.8 | 1 | 1 | 1 | 3.34 | AATTATATCTTATTATTAAAA[C/G]TCTACCAACTCAAAGCTTCC (SEQ ID NO. 212) | 15.4% |
| cytochrome P450, family 1, subfamily A, polypeptide 2 | CYP1A2 | rs762551 | 0.69 | 0.67 | 0.61 | 0.57 | 3.28 | CAAAGGGTGAGCTCTGTGGGC[A/C]CAGGACGCATGGTAGATGGA (SEQ ID NO. 213) | 32.8% |
| histamine receptor H1 | HRH1 | rs901865 | 0.83 | 0.93 | 0.93 | 0.68 | 3.23 | CTCATTGGCGCAAGAGCAGCC[A/G]CCAGTTATGGCTCACTCCCT (SEQ ID NO. 214) | 19.8% |
| cholesteryl ester transfer protein, plasma | CETP | rs5883 | 0.06 | 0 | 0 | 0.13 | 2.94 | AGCTACCTTGGCCAGCGAGTG[A/G]GAAGACTCGCTCAGAACCA (SEQ ID NO. 215) | 6.8% |
| somatostatin | SST | rs2162189 |  |  |  |  | 3.13 | TCTAGAAGGCATCCAGGCCTC[A/G]CCTCTTCTTTCATGTGCAGCTTT (SEQ ID NO. 216) | 11.5% |
| dopamine receptor D1 | DRD1 | rs1799914 | 0 | 0.07 | 0.13 | 0 | 2.26 | CAACTTCTTTGTCATCCTCTT[A/G]GCTGTGTCAGATCTCTTGGT (SEQ ID NO. 217) | 0.3% |
| oxidised low density lipoprotein (lectin-like) receptor 1 | OLR1 | rs2742115 | 0.27 | 0.54 | 0.56 | 0.18 | 2.89 | ACATGTGTACACGTGGTGTAT[A/G]TTAAAAACTTCAGGCTCTCT (SEQ ID NO. 218) | 24.5% |
| lipase, hepatic | LIPC | rs1800588 | 0.26 | 0.39 | 0.59 | 0.53 | 2.84 | TGCAGAAAACCCTTCACCCCC[A/G]TGTCAAAAGGAGCTGACGAA (SEQ ID NO. 219) | 25.0% |
| peroxisome proliferative activated receptor, gamma | PPARG | rs6809631 | 0.21 | 0.41 | 0.44 |  | 3.37 | GGAGAGGGAAAAATAAAGTTA[A/T]TGCATGTCCCAGTTTCCTCA (SEQ ID NO. 220) | 27.3% |
| phosphoinositide-3-kinase, regulatory subunit 1 (p85 alpha) | PIK3R1 | rs706713 | 0.25 | 0.74 | 0.74 | 0.43 | 3.10 | TTTCTCCAATATATTCTAC[A/G]TGTAAGTTCCCGAAAGTCCC (SEQ ID NO. 221) | 27.9% |
| adrenergic, alpha-2A-, receptor | ADRA2A | rs521674 | 0.73 | 0.31 | 0.32 | 0.19 | 1.49 | TTCTACTCCCCTCTTCCCCTTA[A/T]TGAAGGATGCTGTGTGTACA (SEQ ID NO. 222) | 33.3% |
| solute carrier family 39 (zinc transporter), member 7 | SLC39A7 | rs1547387 | 0.13 | 0.04 | 0.05 | 0.02 | 2.96 | GCAACCCGGACATGGACACTC[C/G]CACAGTGGTGAGGAAGAGAC (SEQ ID NO. 223) | 9.9% |
| apolipoprotein C-III | APOC3 | rs2071521 |  |  |  |  | 3.53 | ACAGCTCCTGTTGCCATAGGA[A/G]GGAGCTGGGTGAGATACTAG (SEQ ID NO. 224) | 43.2% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| phosphoinositide-3-kinase, catalytic, beta polypeptide | PIK3Cb | rs1663554 | 0.59 | 0.98 | 0.98 | 0.19 | 2.80 | AAAAACTTTTTCTGATCCCTT[A/C]CTTTTGAAAAGCCCATTAAT (SEQ ID NO. 225) | 45.6% |
| adrenergic, beta-1, receptor | ADRB1 | rs1801253 | 0.68 | 0.75 | 0.85 | 0.59 | 0.93 | TGCGCGCGCAGCAGAGCAGTC[C/G]CTGGAAGGCCTTGCGGAAGT (SEQ ID NO. 226) | 19.0% |
| adiponectin receptor 2 | ADIPOR2 | rs7975375 | 0.13 | 0.07 | 0.09 | 0.23 | 2.61 | CTTTTCACAGGAAAATTTCTT[A/G]GGAGTCTATTGTCACTGTCT (SEQ ID NO. 227) | 14.6% |
| uncoupling protein 3 (mitochondrial, proton carrier | UCP3 | rs2734830 | | | | | 2.93 | CGCATCGGCCTCTATGACTCC[A/G]TCAAGCAGGTGTACACCCCC (SEQ ID NO. 228) | 1.6% |
| uncoupling protein 2 (mitochondrial, proton carrier) | UCP2 | rs660339 | 0.38 | 0.43 | 0.46 | 0.5 | 3.52 | ACACCGCGGTACTGGGCGCTG[A/G]CTGTAGCGCGCACTGGCCC (SEQ ID NO. 229) | 40.9% |
| lipase, hepatic | LIPC | rs11632618 | 0.01 | 0 | 0 | 0 | 2.59 | TGCAATGAAAATGCTCTGTCGG[A/G]TTGGGGTTGTCTAATTGCT (SEQ ID NO. 230) | 6.3% |
| cholinergic receptor, muscarinic 2 | CHRM2 | rs324651 | 0.11 | 0.03 | 0 | 0.25 | 3.07 | TCATCAATCCATGAAACTTAG[A/C]ATAATACTGATAAATTGAAT (SEQ ID NO. 231) | 13.5% |
| autoimmune regulator (autoimmune polyendocrinopathy candidiasis ectodermal dystrophy) | AIRE | rs1003854 | 0.35 | 0.19 | 0.27 | 0.08 | 2.76 | CATTGCGTATTATCAGGAAAA[A/G]AATACTGTCATTAAAGAAA (SEQ ID NO. 232) | 23.7% |
| dopamine receptor D5 | DRD5 | rs2227852 | 0.99 | | | 0 | 1.31 | CTCATCARCTTCTACATCCCC[A/G]TTGCCATCATGATCGTGACC (SEQ ID NO. 233) | 2.9% |
| acetylcholinesterase (YT blood group) | ACHE | rs3757868 | 0.14 | 0 | 0 | 0.03 | 1.81 | ATGCGGGTGGGAGGTGAGAG[A/G]TTGGCGACATTGACGGGAGG (SEQ ID NO. 234) | 13.8% |
| phosphoinositide-3-kinase, class 2, gamma polypeptide | PIK3C2G | rs12582982 | 0.11 | 0.46 | 0.52 | 0.14 | 2.89 | TAAAGTTTGACTTTTCCTATT[C/G]GTAGCTCACTTGAAGACAAA (SEQ ID NO. 235) | 16.9% |
| corticotropin releasing hormone receptor 1 | CRHR1 | rs1396862 | 0.2 | | | 0 | 2.93 | GACCAGGGCTTCTGAACTGCA[A/G]AGGTGCTTTTCCTAAAACC (SEQ ID NO. 236) | 18.8% |
| insulin receptor | INSR | rs7254060 | 0.92 | 0.86 | 0.89 | 0.32 | 3.48 | AAGGGCATTTGCATTCAAAGG[A/G]TTCTAAACGGAAAATGACAA (SEQ ID NO. 237) | 10.4% |
| guanine nucleotide binding protein (G protein), alpha activating polypeptide O | GNAO1 | rs1190762 | 0.12 | 0.1 | 0.15 | 0.27 | 3.18 | AGACTTCCCCAGGAAAGTCCT[A/C]TGTGTCTTGTATTTGGTTAC (SEQ ID NO. 238) | 8.9% |
| cytochrome P450, family 3, subfamily A, polypeptide 4 | CYP3A4 | rs4986910 | 0.01 | 0 | 0 | 0 | 1.74 | ATGTTCATGAGAGCAAACCTC[A/G]TGCCAATGCAGTTTCTGGGT (SEQ ID NO. 239) | 0.3% |
| adrenergic, alpha-1A-, receptor | ADRA1A | rs573542 | 0.97 | 0.97 | 0.78 | 0.79 | 1.19 | AGTGAGGCTTGGAAAGGCGTC[A/G]TGGACAGACCTGGGTCGCTT (SEQ ID NO. 240) | 26.3% |
| angiopoietin 1 | ANGPT1 | rs1283718 | 0.11 | 0.07 | 0.09 | 0.08 | 3.25 | CTTCAAAAAGTGAAACTAACT[A/C]CTCGTTTCTGGTAAAGAGCC (SEQ ID NO. 241) | 7.0% |
| 3-hydroxy-3-methylglutaryl-Coenzyme A reductase | HMGCR | rs3846662 | 0.47 | 0.57 | 0.53 | 0.93 | 2.59 | CCAGTTTAAAAATACATCATA[A/G]GTAAGGCAATGAGAAGAGTT (SEQ ID NO. 242) | 47.1% |
| neuropeptide Y receptor Y5 | NPY5R | rs6837793 | 0.9 | 0.99 | 0.99 | 0.66 | 2.81 | ATGAAATTGTCACTCAGAAGAA[A/G]CTTAATAGGCATTAATACTA (SEQ ID NO. 243) | 12.0% |
| ATP-binding cassette, sub-family C (CFTR/MRP), member 8 | ABCC8 | rs3758947 | 0.19 | 0.31 | 0.24 | 0 | 2.70 | TGCTTTGAGCAAGGGTACCCC[A/G]CTCTGAGAATTCCCAGCCAT (SEQ ID NO. 244) | 15.1% |
| interleukin 1 receptor, type I | IL1R1 | rs2228139 | 0.08 | 0 | 0 | 0.08 | 3.09 | TTCTGCTTAAATATGCTTGT[C/G]CATTATAACATAAGTTAGGC (SEQ ID NO. 245) | 7.0% |
| phosphoinositide-3-kinase, catalytic, delta polypeptide | PIK3CD | rs6541017 | 0.14 | 0.2 | 0.34 | 0.14 | 3.17 | TTTCCCTCTACTCAGTTATCC[A/G]ATTATTCATGACTAGAATGAG (SEQ ID NO. 246) | 14.8% |
| gamma-aminobutyric acid (GABA) A receptor, alpha 2 | GABRA2 | rs11503016 | | | | | 2.86 | CCATAGATCCAAACATCTTTA[A/T]CTATCCATGTATTTGAGTAG (SEQ ID NO. 247) | 14.6% |
| adenosine A2a receptor | ADORA2A | rs3761422 | 0.63 | 0.66 | 0.68 | 0.66 | 2.10 | TCAAGGGCCTTGCTGGGGGCA[A/G]ACAAGGTGGAACATAACACG (SEQ ID NO. 248) | 36.7% |
| insulin-like growth factor 1 (somatomedin C) | IGF1 | rs5742612 | 0.03 | 0.27 | 0.27 | 0.04 | 3.00 | TTGTCCCAGTTGCCAAGTGAG[A/G]GGGTGTGATCTCATTTCCTAG (SEQ ID NO. 249) | 3.9% |
| guanine nucleotide binding protein (G protein), alpha activating activity polypeptide O | GNAO1 | rs4784642 | 0.44 | 0.6 | 0.55 | 0.43 | 3.14 | ATTTTCTTCTGGGTGGCCCTA[A/G]ACTGCTTTCTTTTTCCCCAT (SEQ ID NO. 250) | 46.1% |
| scavenger receptor class B, member 2 | SCARB2 | rs894251 | 0.09 | 0.46 | 0.4 | 0.19 | 3.31 | CTCAGGAGGCCTTACTGTGCC[A/G]TGGTTCTTGCCCTTTGATTT (SEQ ID NO. 251) | 13.8% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| phosphoinositide-3-kinase, class 2, gamma polypeptide | PIK3C2G | rs10841044 | 0.12 | 0 | 0 | 0.02 | 3.44 | AACCAATTCTGGCCTTAAAAG[A/C]AGTCTCTTTATCTCATTCCC (SEQ ID NO. 252) | 15.4% |
| retinoic acid receptor, alpha | RARA | rs9904270 | 0.14 | 0.31 | 0.42 | 0.08 | 3.35 | GCCTTCCCCTTAGAGAAGAGC[A/G]CCTGCCAGACAAGGGAGAAG (SEQ ID NO. 253) | 14.1% |
| ATP-binding cassette, sub-family C (CFTR/MRP), member 8 | ABCC8 | rs722341 | 0.07 | 0.04 | 0.03 | 0 | 2.78 | TTCTGCAGAGCTTCTTCCTCCTTCCT[A/G]TCTCCCACATGACTAATGTT (SEQ ID NO. 254) | 13.0% |
| intercellular adhesion molecule 1 (CD54), human rhinovirus receptor | ICAM1 | rs281432 | 0.48 | 0.26 | 0.36 | 0.64 | 3.03 | ATAGGGAGTCATGGAGGGTTT[C/G]TGAGCAGGCCAGGGATTAGA (SEQ ID NO. 255) | 46.4% |
| nitric oxide synthase 3 (endothelial cell) | NOS3 | rs1799983 | 0.66 | 0.89 | 0.93 | 0.93 | 2.58 | CAGGAGGAAAGAGTTCTGGGGG[A/C]TCATCTGGGGCTGCAGCAG (SEQ ID NO. 256) | 29.7% |
| cytochrome P450, family 2, subfamily C, polypeptide 19 | CYP2C19 | rs4986893 | 0 | 0.03 | 0.05 | 0 | 2.39 | CAGGATTGTAAGCACCCCCTG[A/G]ATCCAGGTAAGGCCAAGTTT (SEQ ID NO. 257) | 0.0% |
| vascular cell adhesion molecule 1 | VCAM1 | rs1041163 | 0.08 | 0.09 | 0.18 | 0.18 | 3.07 | ACCAAATATCTAGGGATCAGA[A/G]AAATTGATTCAGGAAATACT (SEQ ID NO. 258) | 18.0% |
| apolipoprotein F | APOF | rs4301822 | 0 | 0 | 0 | 0.59 | 2.92 | TCTAAGTCATAGCTCTTGATT[A/G]TGGCCCACCCCAGTAGGGA (SEQ ID NO. 259) | 6.3% |
| 5-hydroxytryptamine (serotonin) receptor 3A | HTR3A | rs1150226 | 0.93 | 1 | 1 | 0.63 | 2.82 | TTATGTCACCCTGGGAGTAA[A/G]AGAATGGTCTTCCTGCTCCT (SEQ ID NO. 260) | 11.2% |
| dystrobrevin binding protein 1 | DTNBP1 | rs1018381 | 0.08 | 0.06 | 0.09 | 0.31 | 2.89 | ATCTGCCGGTGATTCAACAGC[A/G]TGCGGAACCTGCATGACGTT (SEQ ID NO. 261) | 9.9% |
| coagulation factor II (thrombin) | F2 | rs5896 | 0.05 | 1 | 1 | 0 | 3.32 | GTAGTGTAGCACCAGGGTCC[A/G]TGGTGCTGCTGCGGGGTTG (SEQ ID NO. 262) | 12.5% |
| protein kinase, AMP-activated, beta 1 non-catalytic subunit | PRKAB1 | rs1062688 | 0 | 1 | 1 | 0 | 0.57 | CCCTCCGGGGCGTCTATGGCC[A/C]CCATGCCGCTCCAGCGCGGC (SEQ ID NO. 263) | 9.9% |
| low density lipoprotein receptor (familial hypercholesterolemia) | LDLR | rs3927 | 0.73 | 0.93 | 0.96 | 0.65 | 2.87 | GACACAGCACACACAACCACCCG[A/G]CTGTTCCCGACACCTCCCG (SEQ ID NO. 264) | 24.0% |
| adenosine A3 receptor | ADORA3 | rs2298191 | 0.28 | 0.26 | 0.31 | 0.12 | 2.31 | TAGGAATGGGCAAATGAAGTG[A/G]CCTTCTGCCCAGCCTCTCT (SEQ ID NO. 265) | 30.5% |
| amiloride binding protein 1 (amine oxidase (copper-containing)) | ABP1 | rs1049793 | 0.31 | 0.54 | 0.61 | 0.67 | 3.01 | GCTCAAAGACCACGGGCGGGT[C/G]CCAGGGGTCGTTCTGGTGGT (SEQ ID NO. 266) | 33.3% |
| superoxide dismutase 1, soluble (amyotrophic lateral sclerosis 1 (adult)) | SOD1 | rs2070424 | 0.09 | 0.53 | 0.39 | 0.19 | 3.03 | CATAGCTTTTGTTAGCTATGCC[A/G]GTAATTAACAGGCATAACTC (SEQ ID NO. 267) | 8.9% |
| glycogen synthase 2 (liver) | GYS2 | rs1871143 | 0.87 | 0.7 | 0.85 | 0.55 | 2.40 | AGCCAGGAGGCTTTCCTGGGCG[A/C]TTTTTTGTACAGGATCTCATT (SEQ ID NO. 268) | 22.4% |
| microsomal triglyceride transfer protein (large polypeptide, 88 kDa) | MTP | rs745075 | 0.09 | 0 | 0 | 0.05 | 3.17 | TGATTTCTTGCATACTTTATT[A/G]AGCAAAATCCATGAGAAGTG (SEQ ID NO. 269) | 11.7% |
| histamine receptor H2 | HRH2 | rs686874 | 0.04 | 0.24 | 0.1 | 0.39 | 3.04 | TGAGATCTAGTAGAAGGACAC[A/G]TCTTGAATTGGGTCATGCTT (SEQ ID NO. 270) | 6.5% |
| LOC441301 | LOC441301 | rs4726107 | 0.05 | 0 | 0 | 0.02 | 2.52 | TGGGGACAGAGGCTAAATACT[A/G]CCCCCTCCCCTTTTCTACTT (SEQ ID NO. 271) | 8.6% |
| dopamine receptor D4 | DRD4 | rs4987059 | | 0 | 0 | 0.43 | 2.79 | TTTTGCAAGCACTTTCTCTT[A/G]CACGTTTGGAACCTACCCCG (SEQ ID NO. 272) | 6.8% |
| proopiomelanocortin (adrenocorticotropin/beta-lipotropin/ alpha-melanocyte stimulating hormone/beta-melanocyte stimulating hormone/beta-endorphin) | POMC | rs3769671 | 0.05 | 0.06 | 0.02 | 0.03 | 2.45 | TTATAAACTGACACACACACA[A/C]AAAAATCCACACACACTTT (SEQ ID NO. 273) | 3.4% |
| adrenergic, alpha-2A-, receptor | ADRA2A | rs1800545 | 0.69 | 0.78 | 0.73 | 0.38 | 0.66 | AGGAGCTCGGAGCAAGAAGGC[A/G]CCCACCGAGGAGGCGTCTGAAG (SEQ ID NO. 274) | 25.0% |
| low density lipoprotein receptor (familial hypercholesterolemia) | LDLR | rs1433099 | | | | | 3.03 | TAATAAATATTAAGGGTGACC[A/G]GTGACTCAGGCTCTGCCTCT (SEQ ID NO. 275) | 28.9% |
| corticotropin releasing hormone | CRH | rs3176921 | 0.07 | 0 | 0 | 0.63 | 2.92 | CTGCAGAAAGCAAGGCCAATAA[A/G]TTCTCTCAAAATGCAGTTCAA (SEQ ID NO. 276) | 15.1% |
| cytochrome P450, family 7, subfamily A, polypeptide 1 | CYP7A1 | rs3808607 | 0.63 | 0.59 | 0.43 | 0.42 | 3.52 | AGTCAACATATATTTGAGAGA[A/C]CTTCAACTTATCAAGTATTG (SEQ ID NO. 277) | 39.8% |
| Oxytocin (Neurophysin 1) | OXT | rs877172 | 0.33 | 0.46 | 0.49 | 0.49 | 2.94 | GGTGAAGAGGGCTGATGGGCC[A/C]AGCAGGTTCACAGAGCTCATC (SEQ ID NO. 278) | 34.1% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| retinoic acid receptor, beta | RARB | rs1290443 | 0.11 | 0.16 | 0.17 | 0.36 | 2.43 | AGAAGCTCTTTCATGTTGTCA[A/G]TTTTAGAAATCCAAATCATT (SEQ ID NO. 279) | 16.4% |
| somatostatin receptor 3 | SSTR3 | rs2071710 | 0.19 | 0.7 | 0.57 | 0.2 | 2.51 | CACGTTGACGATGTTGAGCAC[A/G]TAGAAGGGCATCCAGCAGAG (SEQ ID NO. 280) | 25.0% |
| peroxisome proliferative activated receptor, alpha | PPARA | rs1800206 | 0.04 | 0 | 0 | 0 | 2.59 | TGTGTGACATCCGACAGAAA[C/G]GCACTTGTGAAATCGACAAT (SEQ ID NO. 281) | 7.3% |
| apolipoprotein E | APOE | rs446037 | | | | | 2.02 | AGACACAGGTGACCCAACTCC[A/C]ATGGCTGGCCTAGGCCCCTC (SEQ ID NO. 282) | 1.0% |
| malate dehydrogenase 1, NAD (soluble) | MDH1 | rs2278718 | 0.25 | 0.17 | 0.21 | 0.01 | 3.12 | CTCCCCTGAGTTACACACGCT[A/C]TCTCTCCCGCCAATTGCCGG (SEQ ID NO. 283) | 24.2% |
| thioredoxin reductase 2 | TXNRD2 | rs737865 | | | | | 3.17 | TTTGGATTTTTCCAGCCAGGG[A/G]TTTTTGTGTCCTGTTGCTTT (SEQ ID NO. 284) | 28.9% |
| insulin receptor substrate-1 | IRS1 | rs4675096 | 0.08 | 0.2 | 0.13 | 0.63 | 3.03 | AGTGTTTTTCCAAGGTGTGATT[A/G]AAAATGGAGATTTCTTACCT (SEQ ID NO. 285) | 11.7% |
| apolipoprotein L, 3 | APOL3 | rs132661 | 0.33 | 0.86 | 0.81 | 0.32 | 3.36 | TTCCGCTCCTCCCTGAGCAT[A/G]TATTACTGCTTCCAATACA (SEQ ID NO. 286) | 36.5% |
| protein kinase, AMP-activated, alpha 1 catalytic subunit | PRKAA1 | rs461404 | 0.67 | 0.67 | 0.86 | 0.67 | 2.34 | CATTAGGCACTGTTTTGTTCC[A/G]AGGAAGATATTGCAGGAGAA (SEQ ID NO. 287) | 31.8% |
| microcephaly, primary autosomal recessive 1 | MCPH1 | rs2515449 | 0.07 | 0 | 0 | 0 | 2.64 | AATTTCAACTTATAAACATAC[A/G]TTGCTATAAATATGTTCAAT (SEQ ID NO. 288) | 6.5% |
| Corticotropin-releasing hormone receptor 2 | CRHR2 | rs107540 | 0.77 | 0.47 | 0.65 | 0.58 | 1.82 | AGGGACTGGAGCCTGCTGCCC[A/G]CACGGTGGTCACACCCTGG (SEQ ID NO. 289) | 35.2% |
| v-akt murine thymoma viral oncogene homolog 1 | AKT1 | rs2494746 | 0.92 | 0.26 | 0.34 | 0.56 | 2.68 | GGGGGATGGAGAAGGCAGGATG[C/G]GGCAGGAGGCCTTGGGGGGA (SEQ ID NO. 290) | 13.5% |
| retinoic acid receptor, beta | RARB | rs322695 | 0.23 | 0.08 | 0.07 | 0.02 | 2.69 | CCTGTAGGATTGTGTTCTCT[A/G]AAACTGTCCCTAAATTATG (SEQ ID NO. 291) | 16.7% |
| phosphoinositide-3-kinase, catalytic, alpha polypeptide | PIK3CA | rs870995 | | | | | 2.71 | TCAGGTATTAGCACTTGAAAT[A/C]TAACTTCTTTATGAAGCTCC (SEQ ID NO. 292) | 44.8% |
| 5-hydroxytryptamine (serotonin) receptor 3B | HTR3B | rs3758987 | 0.23 | 0.15 | 0.33 | 0.48 | 3.25 | ACAGCCTTTACCTAAGGCAGT[A/G]CTCTTGCTGACATTCAGGAC (SEQ ID NO. 293) | 29.2% |
| intercellular adhesion molecule 1 (CD54), human rhinovirus receptor | ICAM1 | rs5030390 | 0.11 | 0 | 0 | 0 | 3.33 | CCCAAAGCTGAGAAGTGGGAC[A/G]CCCCAGCACACCCTCCCCA (SEQ ID NO. 294) | 8.1% |
| phosphoinositide-3-kinase, class 2, beta polypeptide | PIK3C2B | rs10494852 | 0.72 | 0.71 | 0.72 | 0.11 | 3.16 | AACTGAAAAGCAGTTTAATCTC[A/G]CCAGAGCCACTGAAGGAGTT (SEQ ID NO. 295) | 30.7% |
| angiotensin II receptor, type 1 | AGTR1 | rs12695902 | 0.08 | 0 | 0 | 0.09 | 3.32 | CATCAGGATTATCAGCATTTA[A/G]GCCAGAGTTGCAAATTAAGT (SEQ ID NO. 296) | 9.1% |
| apolipoprotein E | APOE | rs7412 | | | | | 1.21 | CGGCCTGGTACACTGCCAGGC[A/G]CTTCTGCAGGTCATCGGCAT (SEQ ID NO. 297) | 29.4% |
| insulin receptor substrate 1 | IRS1 | rs1801278 | 0.06 | 0.02 | 0.08 | 0.1 | 2.79 | AGACACTGGTTCCACCTCCGC[A/G]TGGCTGTACAGTGCTGCCGA (SEQ ID NO. 298) | 7.8% |
| phosphofructokinase, liver | PFKL | rs2838549 | 0.07 | 0 | 0 | 0.11 | 0.70 | AGCACCTTAACTATATAGATGGT[A/G]TAACCCGAGTGACCAAGGA (SEQ ID NO. 299) | 15.1% |
| kinase insert domain receptor (a type III receptor tyrosine kinase) | KDR | rs2305948 | 0.07 | 0.16 | 0.08 | 0.29 | 3.41 | AGCACCTTAACTATAGATGGT[A/G]TAACCCGAGTGACCAAGGA (SEQ ID NO. 300) | 13.0% |
| tumor necrosis factor, alpha-induced protein 6 | TNFAIP6 | rs3771892 | | | | | 2.00 | CAGGACCTAGCAAAATACCCC[A/G]TGGTATGATGTTCAAAGTAA (SEQ ID NO. 301) | 17.7% |
| apolipoprotein B (including Ag(x) antigen) | APOB | rs1801701 | 0.05 | 0 | 0 | 0 | 3.09 | TCAGATGGAAAAATGAAAGTCC[A/G]GATTCATTCTGGGTCTTTCC (SEQ ID NO. 302) | 7.0% |
| 5-hydroxytryptamine (serotonin) receptor 6 | HTR6 | rs9659997 | 0.69 | 0.19 | 0.1 | 0.43 | 3.66 | ACAAATGCTCTGAGTCACCAC[A/G]CTGCGGCTCAGATGCTATGA (SEQ ID NO. 303) | 39.1% |
| cytochrome P450, family 3, subfamily A, polypeptide 4 | CYP3A4 | rs1851426 | 0.98 | 1 | 1 | | 3.41 | CACACAGCATCAAGGACTCCA[A/G]TAAGATGGTCCAGCCTCTT (SEQ ID NO. 304) | 9.4% |
| cytochrome P450, family 2, subfamily C, polypeptide 19 | CYP2C19 | rs4244285 | 0.15 | 0.26 | 0.28 | 0.17 | 2.83 | CACTATCATTGATTATTTCCC[A/G]GGAACCCATAACAAATTACT (SEQ ID NO. 305) | 15.1% |
| endothelin 1 | EDN1 | rs5369 | 0.91 | 1 | 1 | | 2.87 | CACAAAGGCAACAGACCGTGA[A/G]AATAGATGCCAATGTGCTAG (SEQ ID NO. 306) | 13.0% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| ankyrin repeat domain 1 (cardiac muscle) | ANKRD1 | rs4933200 | 0.13 | 0.21 | 0.3 | 0.44 | 3.30 | CAGTTAGAATTGTCAATCTAG[A/G]TGGGGACAACTCATTATTTT (SEQ ID NO. 307) | 15.1% |
| adrenergic, alpha-2B-, receptor | ADRA2B | rs2229169 | 0.72 | 0.52 | 0.69 | 0.77 | 2.59 | CTTCTTCAGCTACAGCCTGGG[A/C]GCCATCTGCCGAAGCACTG (SEQ ID NO. 308) | 28.1% |
| brain-derived neurotrophic factor | BDNF | rs6265 | 0.18 | 0.63 | 0.34 | 0 | 3.30 | TTGGCTGACACTTTCGAACAC[A/G]TGATAGAAGAGCTGTTGGAT (SEQ ID NO. 309) | 18.0% |
| lipase, gastric | LIPF | rs814628 | 0.14 | 0.23 | 0.38 | 0 | 3.56 | ATCGACTTCATTGTAAAGAAA[A/G]CTGGACAGAAGCAGCTACAC (SEQ ID NO. 310) | 18.5% |
| angiopoietin 1 | ANGPT1 | rs2514869 | 0.87 | 0.71 | 0.68 | 0.82 | 3.40 | GGCAAGTTTCATCTATTAGC[A/G]ATAAAATGTGAATTTTCTGC (SEQ ID NO. 311) | 13.0% |
| hypoxia-inducible factor 1, alpha subunit (basic helix-loop-helix transcription factor) | HIF1A | rs1951795 | 0.85 | 0.73 | 0.75 | 0.07 | 3.38 | ACTTATTTCAGTGGTTCAAAA[A/C]ATTTCTTCAACGCTTAACCA (SEQ ID NO. 312) | 25.8% |
| cytochrome P450, family 2, subfamily D, polypeptide 6 | CYP2D6 | rs11568728 | | | | | 0.90 | ACCCGACATCTCCCACCCCAG[A/G]ACGCCCCTTTCGCCCCAACG (SEQ ID NO. 313) | 12.8% |
| acetyl-Coenzyme A carboxylase beta | ACACB | rs2241220 | 0.88 | 0.73 | 0.73 | 0.76 | 3.17 | ATCGAAGTTACGCATCCGGTT[A/G]AGTTCCAGCTGGAAGGCCAG (SEQ ID NO. 314) | 19.3% |
| adenosine A2b receptor | ADORA2B | rs2015353 | 0.46 | 0.11 | 0.16 | 0 | 2.81 | AAAGTAGAACATACCAGGCCG[A/G]AGAACAACATGTGCTGCTT (SEQ ID NO. 315) | 47.1% |
| brain-derived neurotrophic factor | BDNF | rs2049045 | 0.18 | 0 | 0 | 0 | 3.47 | AAATCTCTCTTCTTCGATAAA[C/G]TTCCCAGGAGGTAACCCAAT (SEQ ID NO. 316) | 17.4% |
| 5-hydroxytryptamine (serotonin) receptor2A | HTR2A | rs6312 | 0.93 | 0.99 | 1 | 0.77 | 3.43 | AACAAATGTATCTCATGTGTG[A/G]ACCCTGAAGACAAATGTAAG (SEQ ID NO. 317) | 6.8% |
| histamine N-methyltransferase | HNMT | rs12691940 | 0.36 | 0.28 | 0.31 | 0.48 | 3.23 | AATCAACCAAGTGAAGAAAAG[A/G]ATATCAGAGTCTGAAGACAA (SEQ ID NO. 318) | 38.3% |
| disrupted in schizophrenia 1 | DISC1 | rs1322783 | 0.88 | 0.88 | 0.85 | 0.81 | 3.43 | ATCACTCCCTCTTCTAGCATCT[A/G]TTACATTTTCTGGCATTTCT (SEQ ID NO. 319) | 15.9% |
| cytochrome P450, family 2, subfamily D, polypeptide 6 | CYP2D6 | rs1058171 | | | | | 2.04 | AACCTGCGCATAGTGGTGGCT[A/G]ACCTGTTCTCTGCCGGGATG (SEQ ID NO. 320) | 0.0% |
| hypothetical protein MGC4093 | MGC4093 | rs1800469 | 0.69 | 0.55 | 0.48 | 0.78 | 2.32 | AGGGGCAACAGGACACCTGA[A/G]GGATGGAAGGGTCAGGAGGC (SEQ ID NO. 321) | 33.6% |
| retinoid X receptor, alpha | RXRA | rs4917348 | 0.11 | | | | 3.02 | GGTGGGGTTAGAGGGGATGGTT[A/G]CCTGGCAGTGTGCAGCAGAC (SEQ ID NO. 322) | 19.0% |
| tumor necrosis factor, alpha-induced protein 6 | TNFAIP6 | rs1046668 | 0.14 | 0.23 | 0.13 | 0.23 | 3.07 | GGGTCTTTACAGATCCAAAGC[A/G]AATTTTAAATCTCCAGGCT (SEQ ID NO. 323) | 17.2% |
| lipase, hepatic | LIPC | rs6083 | 0.42 | 0.72 | 0.94 | 0.64 | 3.57 | GTCTTTCTCCAGATGATGCCA[A/G]TTTTGTGGATGCATTCATA (SEQ ID NO. 324) | 39.6% |
| fms-related tyrosine kinase 1 (vascular endothelial growth factor/vascular permeability factor receptor) | FLT1 | rs748253 | 0.7 | 0.76 | 0.76 | | 3.27 | GCCCTGGTTTCCTCCAGTATG[A/C]CTGCAAAATTTCCTCTCCAT (SEQ ID NO. 325) | 37.8% |
| haptoglobin | HP | rs2070937 | 0.48 | 0.44 | 0.4 | 0.71 | 3.37 | CCAATGTACTTTCCTGAATGC[A/G]GCCAGAAACTGAGCCCACCC (SEQ ID NO. 326) | 43.8% |
| ghrelin precursor | GHRL | rs26312 | 0.23 | | | | 3.20 | GCTGTTGCTGCCTGGCCTCT[A/G]TGAGCCCCGGGAGTCCGCAG (SEQ ID NO. 327) | 14.3% |
| angiotensin I converting enzyme (peptidyl-dipeptidase A) | ACE | rs1800764 | 0.6 | 0.69 | 0.52 | 0.08 | 2.49 | ATTTGCAAAGTATGTACAGCA[A/G]CCCCCCTATCCTCAGTGG (SEQ ID NO. 328) | 47.9% |
| acetyl-Coenzyme A acetyltransferase 2 (acetoacetyl Coenzyme A thiolase) | ACAT2 | rs15982 | 0.67 | 0.56 | 0.58 | 0.48 | 3.54 | CCCTCCTTCAATATTGACCTA[A/G]CGGGGGAGAAAAGATTTAGA (SEQ ID NO. 329) | 30.5% |
| histamine N-methyltransferase | HNMT | rs1801105 | 0.13 | 0.04 | 0.02 | 0 | 3.38 | TTTACGTTCGAGGTTCGATT[A/G]TCTTGGCTACAAGCTCTAAA (SEQ ID NO. 330) | 8.6% |
| lipoprotein lipase | LPL | rs295 | 0.23 | | | | 2.80 | GATGCACCTACTAGACACCTA[A/C]TCTGCGCTAGATGTGGGG (SEQ ID NO. 331) | 26.6% |
| apolipoprotein L, 3 | APOL3 | rs132642 | 0.88 | 0.99 | 0.98 | 1 | 3.10 | GTCAGTGACTGGAGAGCTCCA[A/T]GGAAAGTCTCTCAGTGACCT (SEQ ID NO. 332) | 11.7% |
| adrenergic, beta-3-, receptor | ADRB3 | rs4994 | | | | | 1.60 | TGGTCTGGAGTCTCGGAGTCC[A/G]GGCGATGGCCACGATGACCA (SEQ ID NO. 333) | 8.6% |
| protein kinase, AMP-activated, gamma 2 non-catalytic subunit | PRKAG2 | rs1860743 | 0.85 | | | | 2.57 | AAAAGGCCTCTGGGGCAGGGA[A/G]GAATGTCCTTTAATGGGGAC (SEQ ID NO. 334) | 9.6% |
| nitric oxide synthase 3 (endothelial cell) | NOS3 | rs1800783 | 0.6 | 0.88 | 0.94 | 0.57 | 3.17 | CATGCTGGAGGAGACAACAGA[A/T]CCCAAGTCTGGCTTCCATAT (SEQ ID NO. 335) | 37.5% |
| carnitine palmitoyltransferase II | CPT2 | rs1799821 | 0.56 | 0.74 | 0.77 | 0.2 | 3.11 | GCCAAGGATGGCTCTACTGCC[A/G]TCCACTTTGAGCACTCTTGG (SEQ ID NO. 336) | 46.1% |
| Choline Kinase Beta | CHKB | rs1064344 | | | | | 3.11 | TGTGGTATCTTTACTGGAACC[A/G]ATAAATGCACCCTGGCTCT (SEQ ID NO. 337) | 7.8% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| phosphoinositide-3-kinase, class 3 | PIK3C3 | rs3813065 | 0.15 | 0.3 | 0.35 | 0.4 | 3.06 | CAAAAATTGGAATTTTGCCAG[A/G]TTTAAATTCCAGTGGCCTTC (SEQ ID NO. 338) | 12.8% |
| gamma-aminobutyric acid (GABA) A receptor, alpha 2 | GABRA2 | rs3756007 | 0.08 | 0.26 | 0.11 | 0 | 2.93 | CAGTTTAAAGTCCAGGGTGTT[A/G]TTATTACGTGTGGCAAAAC (SEQ ID NO. 339) | 6.3% |
| tumor necrosis factor receptor superfamily, member 1B | TNFRSF1B | rs1061622 | 0.25 | 0.2 | 0.16 | 0.16 | 3.53 | GTTGGACGTGCAGACTGCATCC[A/C]TGCTTGCATTCCCAGGGATG (SEQ ID NO. 340) | 22.1% |
| fms-related tyrosine kinase 1 (vascular endothelial growth factor/vascular permeability factor receptor) | FLT1 | rs10507383 | 0.07 | 0.01 | 0 | 0.11 | 2.96 | CCCTTTCAGCAACAACAACCAT[C/G]GGTAGAAATATGATGCAGCG (SEQ ID NO. 341) | 8.1% |
| dopamine receptor D2 | DRD2 | rs1799978 | 0.03 | 0.14 | 0.11 | 0.13 | 2.49 | CCCAGCCTGCAATCACAGCTT[A/G]TTACTCTGGGTGTGGGTGGG (SEQ ID NO. 342) | 9.9% |
| cytochrome P450, family 3, subfamily A, polypeptide 5 | CYP3A5 | rs4646458 | 0.02 | 0.31 | 0.25 | 0.53 | 2.01 | ATTTTCCTTTTTTATTCTTTC[A/C]TTTTCCCCCTTTTCTGAAT (SEQ ID NO. 343) | 8.3% |
| 5-hydroxytryptamine (serotonin) receptor 2A | HTR2A | rs659734 | 0.93 | 1 | 1 | 0.83 | 3.07 | CTGGTAGGAAATTGAACTGAA[A/G]TCATAAACGGAAAGCAGCTA (SEQ ID NO. 344) | 7.6% |
| galanin | GAL | rs694066 | 0.06 | 0.01 | 0 | 0.32 | 2.02 | TTCTAAGTCCTCGCCATGCC[A/G]GGAAAGCCTGGGTGCACCCA (SEQ ID NO. 345) | 13.0% |
| resistin | RETN | rs3219177 |  |  |  |  | 2.62 | CCAGGGATCAGTGAGGTCTCT[A/G]AGACCCTTGGGGAGCTTGCC (SEQ ID NO. 346) | 19.5% |
| choline acetyltransferase | CHAT | rs885834 | 0.59 | 0.22 | 0.32 | 0.16 | 2.46 | ACGACGGCCGTGCCGGGAATAG[A/G]GAAGCAGTGTGAGGACCACA (SEQ ID NO. 347) | 40.1% |
| selectin E (endothelial adhesion molecule 1) | SELE | rs5368 | 0.08 | 0.32 | 0.14 | 0.04 | 3.09 | ACTCAAGTTGAGTTGATCCAT[A/G]TAATTCAAATCCCTCCTCAC (SEQ ID NO. 348) | 12.0% |
| protein kinase, AMP-activated, alpha 2 catalytic subunit | PRKAA2 | rs2796516 | 0.17 | 0.34 | 0.4 | 0.27 | 3.03 | GAACTTTTATAGGTTGCTGGA[A/G]GGAAATGTAAATTAGTGCAAA (SEQ ID NO. 349) | 15.6% |
| cholinergic receptor, nicotinic, alpha polypeptide 7 | CHRNA7 | rs1355920 | 0.9 | 0.77 | 0.83 | 0.45 | 3.00 | ATCAACTGAGGAAGATAATAA[A/G]CTATAAAAAGATGAAAAGGA (SEQ ID NO. 350) | 12.8% |
| apolipoprotein A-I | APOA1 | rs5070 |  |  |  |  | 2.93 | GCCACGGGGATTTAGGGAGAA[A/G]GCCCCCGATGGTTGGCTCC (SEQ ID NO. 351) | 35.2% |
| acetyl-Coenzyme A carboxylase beta | ACACB | rs34274 | 0.9 | 0.82 | 0.69 | 0.35 | 3.42 | CTCTATGATTTCACAGTGATG[A/G]GCTCAAGTATGTGTCTGCTT (SEQ ID NO. 352) | 20.3% |
| angiotensinogen (serine (or cysteine) proteinase inhibitor, clade A (alpha-1 antiproteinase, antitrypsin), member 8) | AGT | rs4762 | 0.08 | 0.08 | 0.1 | 0.04 | 2.96 | GCTGTGAACACGCCCACCACC[A/G]TGGACAGCAGCAGCTGGGCC (SEQ ID NO. 353) | 12.5% |
| 5-hydroxytryptamine (serotonin) receptor 1D | HTR1D | rs676643 | 0.16 | 0.31 | 0.19 | 0.22 | 3.25 | AGGTTCATCTTGACGCATCCT[A/G]AGCTACTTAACTTCGGTTCC (SEQ ID NO. 354) | 17.7% |
| glycogen synthase 2 (liver) | GYS2 | rs1478290 |  |  |  |  | 3.01 | AATGTGGCTGAAGCCAAAAGC[A/G]TAATGAATGAGGGAAGCT (SEQ ID NO. 355) | 31.3% |
| acetylcholinesterase (YT blood group) | ACHE | rs3847063 | 0.46 | 0.83 | 0.91 | 0.1 | 3.00 | TCTTCCCTGGTATGACCTGAC[A/G]TTCCATCTGACATGGTCCCTG (SEQ ID NO. 356) | 44.8% |
| phosphoinositide-3-kinase, regulatory subunit 1 (p85 alpha) | PIK3R1 | rs40318 | 0.8 | 0.78 | 0.78 | 1 | 2.90 | AATAGATGACTGTGAACAGTG[A/G]TGGCCAGGGAACTATCTTCA (SEQ ID NO. 357) | 17.2% |
| vascular endothelial growth factor | VEGF | rs833060 | 0.3 | 0.46 | 0.4 | 0.15 | 2.93 | GGGGCTGCAGAGCAGACTGTCT[A/C]CCAAAGAATCCTCCGAAGG (SEQ ID NO. 358) | 29.7% |
| cytochrome P450, family 2, subfamily C, polypeptide 9 | CYP2C9 | rs1057910 | 0.06 |  |  | 0 | 1.30 | GTGCACGAGGTCCAGGATAC[A/C]TTGACCTTCTCCCCACCAGC (SEQ ID NO. 359) | 15.4% |
| glycogen synthase 2 (liver) | GYS2 | rs2306179 | 0.8 | 0.71 | 0.85 | 0.57 | 3.39 | TTTCAGTAGGTTTGCAGGGAA[A/G]CCAACTCAAAGCTATATCTG (SEQ ID NO. 360) | 25.5% |
| acetyl-Coenzyme A carboxylase alpha | ACACA | rs4795180 | 0.12 | 0.5 | 0.31 | 0.03 | 2.97 | TTCCTGGCCACACTGAGAAAC[A/C]CCTCCTTTCCTTCGACACAT (SEQ ID NO. 361) | 12.5% |
| leptin receptor | LEPR | rs7602 |  |  |  |  | 3.15 | CTTGGAGAGGCAGATAACGCT[A/G]AAGCAGGCCTCTCATGACCC (SEQ ID NO. 362) | 22.1% |
| cytochrome P450, family 3, subfamily A, polypeptide 5 | CYP3A5 | rs6976017 | 0.04 | 0.02 | 0.02 | 0.13 | 3.11 | CTGGGACTGTGGATGGATGTA[A/G]TTTCGTTTTTCTAGTCTGT (SEQ ID NO. 363) | 4.4% |
| interleukin 1, alpha | IL1A | rs1800794 | 0.31 | 0.07 | 0.14 | 0 | 2.95 | AAGCATGGATCTGGGAGGAAA[A/G]CAGCTTGTGTGAGTTGGATA (SEQ ID NO. 364) | 24.0% |
| adrenergic, beta-1, receptor | ADRB1 | rs2429511 | 0.4 | 0.58 | 0.67 | 0.27 | 3.24 | TCCTGGCTTCCTTCTGACCC[A/G]CAAGGGGCAGTCTCAAAATA (SEQ ID NO. 365) | 46.6% |
| adenosine A3 receptor | ADORA3 | rs1415793 | 0.81 | 0.77 | 0.81 | 0.76 | 2.85 | ACACACATGTTCAGCCCAACT[A/G]GAGCCTTTTGTCAGTAAGTC (SEQ ID NO. 366) | 22.4% |

TABLE 10-continued

List of the 384 SNPs in the physiogenomics array. CEU, HCB, JPT, and YRI stand for the allele frequencies in the central European, Han Chinese, Tokyo Japanese and Yoruban African populations according to the HapMap database. GenScore lists the 10th percentile GenScores added up for all 5 runs. Good Runs is the number of runs in which the genotype data passed quality control. MAF is the minor allele frequency as observed in our samples.

| Gene | Symbol | SNP | CEU | HCB | JPT | YRI | Gen-Score | Sequence Context | MAF |
|---|---|---|---|---|---|---|---|---|---|
| 5-hydroxytryptamine (serotonin) receptor 7 (adenylate cyclase-coupled) | HTR7 | rs1935349 | 0.12 | 0.21 | 0.31 | 0.5 | 2.76 | TTATAGATTGTCCAGACATGA[A/G]CAGATCTATCACCTGACCAC (SEQ ID NO. 367) | 15.6% |
| lipoprotein lipase | LPL | rs328 | 0.13 | 0.09 | 0.15 | 0.03 | 2.85 | ACAAGTCTCTGAATAAGAAGT[C/G]AGGCTGGTGAGCATTCTGGG (SEQ ID NO. 368) | 10.2% |
| nuclear receptor subfamily 3, group C, member 1 (glucocorticoid receptor) | NR3C1 | rs10515521 | 0.16 | 0 | 0 | 0.11 | 3.03 | CCTAATCTAAAATTTTCTATT[A/G]CTACATCAAGGGAACAATTT (SEQ ID NO. 369) | 16.7% |
| retinoic acid receptor, gamma | RARG | rs10082776 | 0.07 | 0.21 | 0.27 | 0.64 | 3.22 | TCCCAAGGTGAATGATGGTCT[A/G]AGGACTTCTGGTGGAGAGAA (SEQ ID NO. 370) | 13.3% |
| apolipoprotein B (including Ag(x) antigen) | APOB | rs676210 | 0.19 | 0.69 | 0.67 | 0.17 | 2.62 | ATGTGGGAAGCTGGAATTCT[A/G]GTATGTGAAGGTCAGGAACT (SEQ ID NO. 371) | 22.4% |
| carnitine palmitoyltransferase 1A | CPT1A | rs597316 | 0.31 | 0.11 | 0.23 | 0.09 | 2.70 | CGGGGAAGGAGGAGGCCCTAATTGT[C/G]CAATGGGGGCCGCGTAAATG (SEQ ID NO. 372) | 31.3% |
| nuclear receptor subfamily 3, group C, member 1 (glucocorticoid receptor) | NR3C1 | rs6196 | 0.17 | 0.06 | 0.07 | 0.14 | 2.76 | CAGAAGTTTTTGATATTTCC[A/G]TTTGAATATTTTGGTATCTG (SEQ ID NO. 373) | 16.4% |
| adrenergic, alpha-1A-, receptor | ADRA1A | rs2229126 | 0.03 | 0.07 | 0.02 | 0 | 1.92 | CCTCAGTGAGAACGGGGAGGA[A/T]GTCTAGGACAGGAAAGATGC (SEQ ID NO. 374) | 1.6% |
| serine (or cysteine) proteinase inhibitor, clade E (nexin, plasminogen activator inhibitor type 1), member 1 | SERPINE1 | rs6092 | | | | | 3.42 | ACCTGCCAGTCCTGGGCCTG[A/G]CCCTTGTCTTTGGTGAAGGG (SEQ ID NO. 375) | 12.8% |
| cytochrome P450, family 3, subfamily A, polypeptide 4 | CYP3A4 | CYP3A4_5 | | | | | 2.28 | ATACTTATTGAGAGAAAGAAT[C/G]GATCCAAAAAATCAAATCTT (SEQ ID NO. 376) | 0.0% |
| interleukin 6 (interferon, beta 2) | IL6 | rs2069827 | 0.1 | 0 | 0 | 0 | 2.97 | AAGAAGAGAGATCTCTTCAAGAT[A/C]GATAAAACAGTGACCTCTGT (SEQ ID NO. 377) | 8.3% |
| tumor necrosis factor (ligand) superfamily, member 6 | TNFSF6 | rs6700734 | 0.33 | 0.08 | 0.16 | 0.34 | 3.38 | AAATAAACCAGAAATTGGTAA[A/G]TCATCACATGGAAATCAAAT (SEQ ID NO. 378) | 24.2% |
| cholinergic receptor, nicotinic, alpha polypeptide 7 | CHRNA7 | rs2221223 | 0.16 | 0.03 | 0.01 | 0.08 | 2.93 | GAATTGGTCCACCAGCAAAAC[A/C]CATTTGCTCTCCGTGGACT (SEQ ID NO. 379) | 16.4% |
| peptide YY | PYY | rs1058046 | 0.72 | 0.27 | 0.33 | 0.44 | 2.34 | GGAAAAGAGACGGCCCGGACA[C/G]GCTTCTTTCCAAAAGTTCT (SEQ ID NO. 380) | 26.6% |
| brain-derived neurotrophic factor | BDNF | rs908867 | 0.12 | 0.01 | 0.08 | 0.09 | 1.05 | GCACCTACACCAACAATTCAG[A/G]GTATCCCACTGAAGATATA (SEQ ID NO. 381) | 6.8% |
| ATP-binding cassette, sub-family B (MDR/TAP), member 1 | ABCB1 | rs1045642 | | | | | 2.92 | GGCCTCCTTTGCTGCCCTCAC[A/G]ATCTCTTCCTGTGACCAC (SEQ ID NO. 382) | 33.9% |
| retinoid X receptor, gamma | RXRG | rs157864 | 0.17 | 0.12 | 0.32 | 0.24 | 2.89 | ATGTATATTGAATTAAAGGAAAA[A/G]TGAATGGTCTCAGTCAGAGA (SEQ ID NO. 383) | 10.7% |
| cholecystokinin B receptor | CCKBR | rs1805002 | 0.04 | 0.01 | 0.07 | 0.09 | 2.78 | GGCACATTCATCTCTTTGGCACC[A/G]TCATCTGCAAGGCGGTTTCC (SEQ ID NO. 384) | 3.9% |

TABLE 11

Summary of SNP assay results.

| Good runs | Count | Fraction |
|---|---|---|
| 0 | 68 | 18% |
| 1 | 31 | 8% |
| 2 | 55 | 14% |
| 3 | 140 | 36% |
| 4 | 67 | 17% |

TABLE 11-continued

Summary of SNP assay results.

| Good runs | Count | Fraction |
|---|---|---|
| 5 | 23 | 6% |
| Grand Total | 384 | |

What is claimed is:

1. A method of constructing a physiogenomics model suitable for predicting a human individual's response to an environmental stimulus comprising:
   (a) selecting a plurality of genetic markers based on an analysis of a fraction of the human genome;
   (b) exposing each subject of a study human population to the environmental stimulus and recording physiological response phenotypes for the study human population to the environmental stimulus;
   (c) using principal component analysis and identifying significant covariates among demographic data and clinical data for the study human population to the physiological response phenotypes for the study human population from (b);
   (d) performing for a genotype for each subject of the study human population from (b) and the physiological response phenotypes for the study human population from (b) an unadjusted association test, and identifying a subset of selected markers associated with the response to the environmental stimulus from the plurality of genetic markers;
   (e) using permutation testing on the subset of selected markers from (d) to obtain an adjusted probability value and choosing model building markers from the subset of selected markers;
   (f) identifying from the association testing in step (e) one or more markers from the plurality of genetic markers not associated with the study human population's physiological response to the environmental stimulus in order to serve as a physiogenomic control;
   (g) constructing the physiogenomic model from the significant covariates from (c), the model building markers from (e), and the physiogenomic control from (f) by linear regression analysis and model parameterization; and
   (h) presenting a display of the physiogenomic model to a user, wherein the physiogenomics model is suitable for predicting the human individual's response to the environmental stimulus.

2. The method according to claim 1, wherein the step of selecting a plurality of genetic markers comprises DNA screening using a fixed array.

3. The method according to claim 1, wherein the physiological response phenotypes are endophenotypes.

4. The method according to claim 1, wherein said covariates are determined by generating a covariance matrix for the demographic data and the physiological response phenotypes.

5. The method of claim 1, wherein the subset of selected markers associated with the response to the environmental stimulus in (d) include strongly associated markers and neutral markers.

6. The method of claim 5, wherein the strongly associated markers include oppositely associated markers.

7. The method of claim 1, wherein the fraction of the human genome includes SNPs from a known public database.

8. The method of claim 1, wherein the demographic data and physiological response phenotypes includes clinically derived data.

9. The method of claim 8, wherein the clinically derived data includes a serum concentration of a particular substance.

10. The method of claim 9, wherein the particular substance is a serum lipid.

11. The method of claim 9, wherein the clinically derived data includes BMI data.

12. The method of claim 1, wherein the plurality of genetic markers include inflammatory markers.

13. The method of claim 12, wherein the inflammatory markers include markers in genes relevant to energy generation, inflammation, muscle structure, mitochondria, oxygen consumption, blood pressure, lipid metabolism, behavior, or transcription factors.

14. The method of claim 1, wherein the subset of selected markers associated with the response to the environmental stimulus from (d) have a probability value of <0.05 in the unadjusted association test.

15. The method of claim 1, wherein the model building markers from (e) have a non-parametric and marker complexity probability value of $p < 0.05$.

16. The method of claim 1, further comprising producing from the physiogenomic model a physiogenomic array.

17. The method of claim 16, wherein the physiogenomic array comprises at least 10 SNPs.

18. The method of claim 1, further comprising producing a distribution plot of model building marker frequency vs. a level of a physiological response from the physiogenomics model of claim 1 suitable for predicting the human individual's response to the environmental stimulus.

19. The method of claim 18, further comprising ranking a response of the human individual against the distribution plot.

20. The method of claim 19, further comprising using the ranking to design an intervention for the individual.

21. The method of claim 20, wherein the intervention is an exercise, diet or drug regimen.

22. The method of claim 1, wherein the environmental stimulus is exercise.

23. The method of claim 1, further comprising genotyping each subject of the human study population for the plurality of genetic markers to produce genotypes for the human study population.

* * * * *